(12) United States Patent
Fukuda et al.

(10) Patent No.: US 8,222,407 B2
(45) Date of Patent: Jul. 17, 2012

(54) MUTILIN DERIVATIVE HAVING HETEROCYCLIC AROMATIC RING CARBOXYLIC ACID STRUCTURE IN SUBSTITUENT AT 14-POSITION

(75) Inventors: Yasumichi Fukuda, Tochigi (JP); Masanori Takadoi, Tochigi (JP); Yoshikazu Asahina, Tochigi (JP); Taro Sato, Tochigi (JP); Haruaki Kurasaki, Tochigi (JP); Hiroyuki Ebisu, Tochigi (JP); Masaya Takei, Tochigi (JP); Hideyuki Fukuda, Tokyo (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 158 days.

(21) Appl. No.: 12/451,656

(22) PCT Filed: May 23, 2008

(86) PCT No.: PCT/JP2008/059535
§ 371 (c)(1),
(2), (4) Date: Nov. 24, 2009

(87) PCT Pub. No.: WO2008/143343
PCT Pub. Date: Nov. 27, 2008

(65) Prior Publication Data
US 2010/0197909 A1    Aug. 5, 2010

(30) Foreign Application Priority Data

May 24, 2007 (JP) ................ P2007-137473

(51) Int. Cl.
C07D 498/04    (2006.01)
C07D 401/10    (2006.01)
C07D 413/14    (2006.01)
C07D 471/04    (2006.01)

(52) U.S. Cl. ......... 544/101; 544/128; 546/123; 546/156
(58) Field of Classification Search ......................... None
See application file for complete search history.

(56) References Cited

U.S. PATENT DOCUMENTS

| | | |
|---|---|---|
| 4,148,890 A | 4/1979 | Czok et al. |
| 4,292,317 A | 9/1981 | Pesson |
| 4,398,029 A | 8/1983 | Irikura et al. |
| 4,428,953 A | 1/1984 | Berner et al. |
| 4,604,401 A | 8/1986 | Mich et al. |
| 4,638,067 A | 1/1987 | Culbertson et al. |
| 4,665,079 A | 5/1987 | Culbertson et al. |
| 4,738,968 A | 4/1988 | Matsumoto et al. |
| 4,753,953 A | 6/1988 | Masuzawa et al. |
| 4,771,054 A | 9/1988 | Domagala et al. |
| 4,771,055 A | 9/1988 | Domagala et al. |
| 4,777,175 A | 10/1988 | Culbertson et al. |
| 4,822,801 A | 4/1989 | Domagala et al. |
| 4,844,902 A | 7/1989 | Grohe |
| 4,886,810 A | 12/1989 | Matsumoto et al. |
| 4,894,458 A | 1/1990 | Masuzawa et al. |
| 4,920,120 A | 4/1990 | Domagala et al. |
| 4,954,507 A | 9/1990 | Weber et al. |
| 4,965,273 A | 10/1990 | Weber et al. |
| 4,988,709 A | 1/1991 | Ogata et al. |
| 4,997,943 A | 3/1991 | Iwata et al. |
| 5,023,257 A | 6/1991 | Pöllinger et al. |
| 5,097,032 A | 3/1992 | Domagala et al. |
| 5,098,912 A | 3/1992 | Hayakawa et al. |
| 5,137,892 A | 8/1992 | Chu et al. |
| 5,140,033 A | 8/1992 | Schriewer et al. |
| 5,152,986 A | 10/1992 | Lange et al. |
| 5,164,402 A | 11/1992 | Brighty |
| 5,173,484 A | 12/1992 | Petersen et al. |
| 5,229,396 A | 7/1993 | Brighty |

(Continued)

FOREIGN PATENT DOCUMENTS

CA    1288712    9/1991

(Continued)

OTHER PUBLICATIONS

F. Zaragoza Dorwald, Side Reactions in Organic Synthesis; A Guide to Successful Synthesis Design, Wiley-VCH, Weinheim, Preface, p. IX (2005).*

(Continued)

*Primary Examiner* — Janet Andres
*Assistant Examiner* — Timothy R Rozof
(74) *Attorney, Agent, or Firm* — Wenderoth, Lind & Ponack, L.L.P.

(57) ABSTRACT

To provide a novel mutilin derivative having a substitution at the 14-position, which is a novel mutilin analogue exhibiting a potent and broad antimicrobial action against Gram-positive bacteria and Gram-negative bacteria including various drug-resistant bacteria, and which is expected to be useful as an agent for treating infectious diseases. A mutilin derivative represented by the following general formula (1):

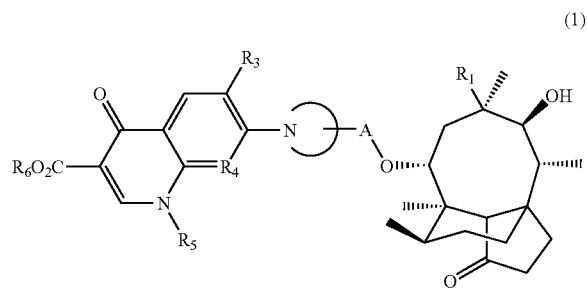

or a pharmaceutically acceptable addition salt thereof.

5 Claims, No Drawings

U.S. PATENT DOCUMENTS

| | | | |
|---|---|---|---|
| 5,252,734 A | 10/1993 | Schriewer et al. |
| 5,262,417 A | 11/1993 | Gammill et al. |
| 5,266,569 A | 11/1993 | Brighty |
| 5,281,612 A | 1/1994 | Domagala et al. |
| 5,284,842 A | 2/1994 | Petersen et al. |
| 5,290,934 A | 3/1994 | Ueda et al. |
| 5,336,768 A | 8/1994 | Albrecht et al. |
| 5,380,874 A | 1/1995 | Hayakawa et al. |
| 5,385,906 A | 1/1995 | Gammill et al. |
| 5,391,763 A | 2/1995 | Brighty |
| 5,409,933 A | 4/1995 | Kim et al. |
| 5,416,222 A | 5/1995 | Hayakawa et al. |
| 5,453,422 A | 9/1995 | Petersen et al. |
| 5,468,742 A | 11/1995 | Petersen et al. |
| 5,476,950 A | 12/1995 | Hayakawa et al. |
| 5,495,020 A | 2/1996 | Ueda et al. |
| 5,563,138 A | 10/1996 | Ueda et al. |
| 5,578,604 A | 11/1996 | Himmler et al. |
| 5,585,491 A | 12/1996 | Domagala et al. |
| 5,591,744 A | 1/1997 | Ueda et al. |
| 5,646,163 A | 7/1997 | Demuth, Jr. et al. |
| 5,659,038 A | 8/1997 | Himmler et al. |
| 5,668,147 A | 9/1997 | Nakano et al. |
| 5,677,316 A | 10/1997 | Ao et al. |
| 5,723,648 A | 3/1998 | Ueda et al. |
| 5,811,576 A | 9/1998 | Ueda et al. |
| 6,020,368 A | 2/2000 | Hinks et al. |
| 6,121,281 A | 9/2000 | Takle et al. |
| 6,194,434 B1 | 2/2001 | Takemura et al. |
| 6,239,175 B1 | 5/2001 | Hinks et al. |
| 6,281,226 B1 | 8/2001 | Berry et al. |
| 6,329,391 B1 | 12/2001 | Ledoussal et al. |
| 6,784,193 B1 | 8/2004 | Ascher et al. |
| 6,967,205 B1 | 11/2005 | Abdul-Rahman |
| 2002/0022629 A1 | 2/2002 | Cagle et al. |
| 2002/0028816 A1 | 3/2002 | Cagle et al. |
| 2002/0049192 A1 | 4/2002 | Ledoussal et al. |
| 2002/0173501 A1 | 11/2002 | Ledoussal et al. |
| 2002/0193370 A1 | 12/2002 | Cagle et al. |
| 2003/0069253 A1 | 4/2003 | Cagle et al. |
| 2003/0114674 A1 | 6/2003 | Brooks et al. |
| 2003/0119848 A1 | 6/2003 | Takemura et al. |
| 2003/0162831 A1 | 8/2003 | Ascher et al. |
| 2003/0207862 A1 | 11/2003 | Ledoussal et al. |
| 2004/0024059 A1 | 2/2004 | Elder et al. |
| 2004/0058937 A1 | 3/2004 | Aitken et al. |
| 2004/0097512 A1 | 5/2004 | Cagle et al. |
| 2004/0102482 A1 | 5/2004 | Ascher et al. |
| 2004/0132993 A1 | 7/2004 | Shetty |
| 2004/0235910 A1 | 11/2004 | Ascher et al. |
| 2005/0096357 A1 | 5/2005 | Elder et al. |
| 2005/0101589 A1 | 5/2005 | Ledoussal et al. |
| 2005/0159377 A1 | 7/2005 | Ferguson et al. |
| 2005/0209210 A1 | 9/2005 | Ding et al. |
| 2005/0215637 A1 | 9/2005 | Ascher et al. |
| 2005/0250811 A1 | 11/2005 | Berner et al. |
| 2006/0100436 A1 | 5/2006 | Ledoussal et al. |
| 2007/0167495 A1 | 7/2007 | Brown et al. |
| 2008/0071086 A1 | 3/2008 | Bradbury et al. |
| 2008/0221330 A1 | 9/2008 | Takadoi et al. |
| 2008/0306072 A1 | 12/2008 | Mang et al. |
| 2009/0306203 A1 | 12/2009 | Mang et al. |

FOREIGN PATENT DOCUMENTS

| | | | |
|---|---|---|---|
| CN | 1583724 | | 2/2005 |
| DE | 3632222 | | 4/1988 |
| EP | 0 106 489 | | 4/1984 |
| EP | 0 153 163 | A2 | 8/1985 |
| EP | 0 169 710 | | 1/1986 |
| EP | 0 172 651 | A1 | 2/1986 |
| EP | 0 274 033 | | 7/1988 |
| EP | 0 280 915 | | 9/1988 |
| EP | 0 284 935 | | 10/1988 |
| EP | 0 295 495 | | 12/1988 |
| EP | 0 326 916 | | 8/1989 |
| EP | 0 337 231 | | 10/1989 |
| EP | 0 343 524 | | 11/1989 |
| EP | 0 391 132 | | 10/1990 |
| EP | 0 523 512 | | 1/1993 |
| EP | 0 574 231 | | 12/1993 |
| EP | 0 671 391 | | 9/1995 |
| EP | 0 900 793 | A1 | 3/1999 |
| ES | 2 065 846 | | 2/1995 |
| JP | 53-86038 | | 7/1978 |
| JP | 55-94359 | | 7/1980 |
| JP | 59-67269 | | 4/1984 |
| JP | 60-214773 | | 10/1985 |
| JP | 61-43186 | | 3/1986 |
| JP | 61-282362 | | 12/1986 |
| JP | 62-4284 | | 1/1987 |
| JP | 62-019583 | | 1/1987 |
| JP | 62-228063 | | 10/1987 |
| JP | 63-166876 | | 7/1988 |
| JP | 63-198664 | | 8/1988 |
| JP | 1-135770 | | 5/1989 |
| JP | 01-230558 | | 9/1989 |
| JP | 3-209367 | | 9/1991 |
| JP | 6-040814 | | 2/1994 |
| JP | 7-300471 | | 11/1995 |
| JP | 09-136886 | | 5/1997 |
| JP | 2000-319261 | | 11/2000 |
| JP | 2003-96075 | | 4/2003 |
| JP | 2006-306727 | | 11/2006 |
| JP | 2008-280297 | | 11/2008 |
| JP | 2009-040709 | | 2/2009 |
| WO | 88/02627 | | 4/1988 |
| WO | 89/06649 | | 7/1989 |
| WO | 90/06307 | | 6/1990 |
| WO | 91/02526 | | 3/1991 |
| WO | 92/10191 | | 6/1992 |
| WO | 93/03026 | | 2/1993 |
| WO | 94/10163 | | 5/1994 |
| WO | 95/11902 | | 5/1995 |
| WO | 96/33992 | | 10/1996 |
| WO | 97/40037 | A1 | 10/1997 |
| WO | 99/14214 | | 3/1999 |
| WO | 99/21855 | | 5/1999 |
| WO | 99/51219 | | 10/1999 |
| WO | 00/07974 | | 2/2000 |
| WO | 00/18386 | | 4/2000 |
| WO | 00/18388 | | 4/2000 |
| WO | 00/27790 | | 5/2000 |
| WO | 00/37074 | | 6/2000 |
| WO | 00/71560 | | 11/2000 |
| WO | 00/73287 | | 12/2000 |
| WO | 01/09095 | | 2/2001 |
| WO | 01/14310 | | 3/2001 |
| WO | 01/36408 | | 5/2001 |
| WO | 01/58876 | | 8/2001 |
| WO | 01/89496 | | 11/2001 |
| WO | 02/04414 | | 1/2002 |
| WO | 02/17916 | | 3/2002 |
| WO | 02/22580 | | 3/2002 |
| WO | 03/078439 | | 9/2003 |
| WO | 2004/089886 | | 10/2004 |
| WO | 2005/049602 | | 6/2005 |
| WO | 2005/070941 | | 8/2005 |
| WO | 2006/070671 | | 7/2006 |
| WO | 2006/119694 | | 11/2006 |
| WO | 2007/000001 | | 1/2007 |
| WO | 2007/000004 | | 1/2007 |
| WO | 2007/014409 | | 2/2007 |
| WO | 2007/037518 | | 4/2007 |
| WO | 2008/021491 | | 2/2008 |

OTHER PUBLICATIONS

Definition for "Infectious Disease" [retrieved May 15, 2011]. Retrieved from the Internet: http://www.merriam-webster.com/medical/infectious+disease?show=0&t=1305401385.*

Frederick Kavanagh et al., "Antibiotic Substances from Basidiomycetes. VIII. Pleurotus Multilus (Fr.) SACC. and Pleurotus Passeckerianus Pilat", Proc. Natl. Acad. Sci., vol. 37, pp. 570-574, 1951.

F. Knauseder et al., "Pleuromutilins Fermentation, Structure and Biosynthesis", The Journal of Antibiotics, vol. 29, No. 2, pp. 125-131, 1976.

H. Berner et al., "Chemie Der Pleuromutiline—II Synthese Des 12-Desvinylpleuromutilins", Tetrahedron, vol. 37, pp. 915-919, 1981.

Heinz Berner et al., "Chemie Der Pleuromutiline—V Photoisomerisierung AB-Trans-Anellierter 11-Oxo-Multilane", Tetrahedron, vol. 39, No. 10, pp. 1745-1748, 1983.

Heinz Berner et al., "Chemie der Pleuromutiline, 11. Mitt.[1]: Konfigurationsumkehr der Vinylgruppe am Kohlenstoff 12 durch reversible Retro-En-Spaltung", Monatshefte für Chemie, vol. 117, pp. 1073-1080, 1986.

A.J. Birch et al., "The Structure and Some Aspects of the Biosynthesis of Pleuromutilin", Tetrahedron, Suppl. 8, Part II, pp. 359-387, 1966.

Gerald Brooks et al., "Pleuromutilins. Part 1: The Identification of Novel Mutilin 14-Carbamates", Bioorganic & Medicinal Chemistry, vol. 9, pp. 1221-1231, 2001.

G. Schultz et al., "Chemie der Pleuromutiline—VI Vergleichende Untersuchung Der $^{13}$C-NMR Spektren Des Tricyclischen Diterpens Mutilin Und Einer Reihe Von Multilinderivaten", Tetrahedron, vol. 40, No. 5, pp. 905-917, 1984.

Eric Bacque et al., "A flexible strategy for the divergent modification of pleuromutilin" Chemical Communication, vol. 20, pp. 2312-2313, 2002.

European Search Report dated Sep. 19, 2008, issued in European Application No. 04787732.

K. Tomita et al., "Synthesis and Structure—Activity Relationships of Novel 7-Substituted 1,4-Dihydro-4-oxo-1-(2-thiazolyl)-1,8-naphthyridine-3-carboxylic Acids as Antitumor Agents, Part 1", J. Med. Chem., 45, pp. 5564-5575, 2002.

D. Bouzard et al. "Fluoronaphthyridines and Quinolones as Antibacterial Agents. 2. Synthesis and Structure-Activity Relationships of New 1-*tert*-Butyl 7-Substituted Derivatives", J. Med. Chem., vol. 33, pp. 1344-1352, 1990.

Patani et al., "Bioisosterism: A Rational Approach in Drug Design", Chem. Rev., 96 (8), pp. 3147-3176, 1996.

G. S. Banker et al., "Modern Pharmaceutics, 3$^{rd}$ ed.", Marcel Dekker, New York, pp. 451 and 596, 1996.

Manfred E. Wolff, "Burger's Medicinal Chemistry, 5$^{th}$ ed., Part I", John Wiley & Sons, pp. 975-977, 1995.

International Search Report mailed Oct. 19, 2004, issued in International Application No. PCT/JP2004/013049.

H. Berner et al., "Synthese AB-*TRANS*-Anellierter Derivate Des Tricyclischen Diterpens Pleuromutilin Durch Intramolekulare 1,5-Hydrid-Verschiebung", Tetrahedron, vol. 36, pp. 1807-1811, 1980.

B. Orlek et al., "Comparison of Azabicyclic Esters and Oxidiazoles as Ligands for the Muscarinic Receptor", J. Med. Chem., vol. 34, pp. 2726-2735, 1991.

B. Orlek et al., "Diastereoselective Routes to endo and exo Ethyl 1-azabicyclo[2.2.1] hept-3-YL carboxylates", Tetrahedron Lett., vol. 32, pp. 1241-1244, 1991.

G. Showell et al., "Synthesis and in Vitro Biological Profile of All Four Isomers of the Potent Muscarinic Agonist 3-(3-Methyl-1,2,4-oxadiazol-5yl)-1-azabicyclo[2.2.1]heptane", J. Med. Chem., vol. 35, pp. 911-916, 1992.

I. Cottrell et al., "A Synthesis of 1-Azabicyclo[2.2.1]heptane-3-carboxylic Acid Esters in Enantiomerically Pure Form", J. Chem. Soc. Perkin Trans., vol. I, pp. 1091-1097, 1991.

K. Murdock et al., "Alternative Approaches to 1-Substituted Thymines", J. Org. Chem., vol. 27, pp. 3317-3319, 1962.

B. Akteries et al., "Carbonyl Diisocyanate: A New Preparation and Some Reactions", Chem. Ber., vol. 119, pp. 83-95, 1986.

V. Sheludyakov et al., "Synthesis and Properties of Organic and Organosilicon Acyl Isocyanates", J. Gen. Chem. USSR, pp. 2061-2067, 1977.

C. H. DePuy et al., "A One-Step Synthesis of 1-Substituted Cyclopropanols", J. Org. Chem., Communications to the Editor, vol. 27, pp. 3742, 1962.

Speziale et al., "A New and Convenient Synthesis of Acyl Isocyanates"., J. Org. Chem., Communications to the Editor, vol. 27, pp. 3742-3743, 1962.

J. Carey, "Asymmetric 1,3-Dipolar Cycloaddition of a (Z)-Alkene Dipolarophile, Synthesis of (3S,4R) Ethyl 1-Azabicyclo[2.2.1]heptanes-3-carboxylate", J. Org. Chem., vol. 66, pp. 2526-2529, 2001.

Supplementary European Search Report issued Aug. 3, 2010 in corresponding European Application No. 08 76 4581, in the English language.

Hunt E., "Pleuromutilin Antibiotics", Drugs of the Future, vol. 25., No. 11, pp. 1163-1168 (2000).

International Search Report issued Jun. 24, 2008 in International (PCT) Application No. PCT/JP2008/059535.

* cited by examiner

MUTILIN DERIVATIVE HAVING HETEROCYCLIC AROMATIC RING CARBOXYLIC ACID STRUCTURE IN SUBSTITUENT AT 14-POSITION

TECHNICAL FIELD

The present invention relates to a mutilin derivative having a heterocyclic aromatic ring carboxylic acid structure in a substituent at the 14-position, which is a novel mutilin analogue exhibiting a potent antimicrobial action against Gram-positive bacteria and Gram-negative bacteria including various resistant bacteria, and being expected to be useful as an agent for treating infectious diseases.

BACKGROUND ART

Pleuromutilin is a diterpene compound which has been isolated/identified in terms of its structure from *Pleurotus mutilus* Sacc. in 1951 and from *Pleurotus passeckerianus* Pil. in 1976, and the aglycone part thereof is referred to as mutilin (Non-Patent Documents 1 and 2). Its structural features include a three-ring structure consisting of a highly functionalized eight-membered ring fused with a hydroindanone structure and containing nine asymmetric carbon atoms.

[Chem. 1]

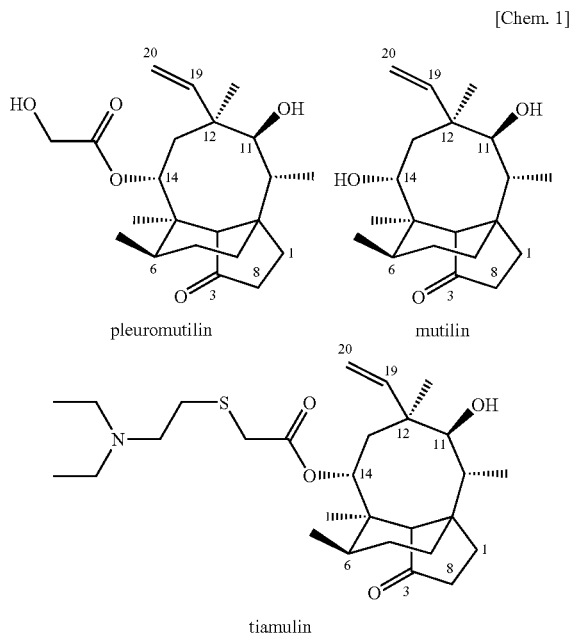

Recently, the spread of intractable infectious diseases caused by various resistant bacteria has become a worldwide concern. It is obvious that pleuromutilin exhibits an antimicrobial activity by inhibiting the protein synthesis by acting on ribosomes in bacteria. Thus, pleuromutilin is useful as a new lead compound in the search for an agent for treating intractable infectious diseases. Among these, Tiamulin, as a pleuromutilin derivative, has long been used as an agent for treating infectious diseases in livestock; however, there are no reports of pleuromutilin or mutilin derivatives ever being applied to the treatment of infectious diseases in humans.

As such, the mutilin compound is a compound that has attracted worldwide attention in terms of two points, that is, its potent microbial activity and unique chemical structure. In recent years, several groups have reported novel mutilin derivatives. That is, for example, there have been reported a mutilincarbamoyloxy derivative (Patent Document 1), a pleuromutilin derivative (Patent Document 2), a pleuromutilin derivative (Patent Document 3), a 2-fluoromutilin derivative (Patent Document 4), a mutilin compound (Patent Document 5), a mutilin-14-ester derivative (Patent Document 6), an isoxazoline carboxylic acid derivative (Patent Document 7), a mutilin derivative (Patent Document 8), pleuromutilinbeta-ketoesters (Patent Document 9), a 2-hydroxymutilincarbamate derivative (Patent Document 10), a pleuromutilin derivative (Patent Document 11), a heterocyclic ester derivative (Patent Document 12), antimicrobially active mutilins (Patent Document 13), a novel pleuromutilin derivative (Patent Document 14), a pleuromutilin derivative (Patent Document 15), an organic compound (Patent Document 16), a pleuromutilin derivative having a hydroxyamino or acylaminocycloalkyl group (Patent Document 17), and a pleuromutilin derivative (Patent Document 18). All of these are patents claiming a pleuromutilin-derived vinyl group in which a substituent at the 12-position is naturally occurring, or an ethyl group resulting from the reduction of the vinyl group, but there have been no reports of a mutilin derivative having a structural feature in which a 1,4-dihydro-4-oxo-3-quinolonecarboxylic acid structure, a 1,4-dihydro-4-oxo-3-naphthylidinecarboxylic acid structure, or a pyridobenzoxazine structure, which is a heterocyclic aromatic ring carboxylic acid structure, is bonded via an acylcarbamoyl bond and a piperidine ring in a substituent at the 14-position. Thus, their antimicrobial activity is not known yet. In addition, as a mutilin derivative having a structural feature in which the substituents at the 12-position are various substituents other than a vinyl group or an ethyl group as shown in the present invention, there have been reported, for example, a mutilin derivative having a substituent at the 12-position (Patent Document 19), a mutilin derivative having a substituent at the 12-position having a pyridine ring in a substituent at the 14-position (Patent Document 20), and the like. All of these are characterized in that they have a 1-azabicyclo[2.2.1]heptane structure or a pyridine structure via an acylcarbamoyl bond in a substituent at the 14-position, and there have been no reports of a mutilin derivative having a structural feature in which a 1,4-dihydro-4-oxo-3-quinolonecarboxylic acid structure, a 1,4-dihydro-4-oxo-3-naphthylidinecarboxylic acid structure, or a pyridobenzoxazine structure, which is a heterocyclic aromatic ring carboxylic acid structure, is bonded via an acylcarbamoyl bond and a piperidine ring in a substituent at the 14-position.

As a mutilin derivative having a substituent at the 12-position and a 4-epimutilin derivative having a substituent at the 12-position, the following compounds are known. That is, a 4-epimutilin derivative having desethenyl at the 12-position (Non-Patent Document 3), a 4-epimutilin derivative having dimethyl substituted at the 12-position (Non-Patent Document 4), and a pleuromutilin derivative in which the stereochemistry of the substituent at the 12-position is opposite to that of a natural form and a pleuromutilin derivative having cyclopropyl substituted at the 12-position (Non-Patent Document 5) are known. All of these are the compounds in which the substituent at the 12-position as described in the present Patent Document is neither a naturally occurring vinyl group nor an ethyl group resulting from the reduction of the vinyl group, and there have been no reports of a mutilin derivative having a structural feature in which a 1,4-dihydro-4-oxo-3-quinolonecarboxylic acid structure, a 1,4-dihydro-4-oxo-3-naphthylidinecarboxylic acid structure, or a pyridobenzoxazine structure, which is a heterocyclic aromatic ring carboxylic acid structure, is bonded via an acylcarbamoyl bond and a piperidine ring in a substituent at the 14-position as shown in the present Patent Document.

Moreover, as for the mutilin derivative in which a hydroxyl group at the 11-position is protected, the following compounds are known. That is, a mutilin derivative (Non-Patent Document 6) is known, and in the present article, a mutilin form having acetoxy, dichloroacetoxy, and trifluoroacetoxy at the 11-position has been reported, and their compounds have become well-known. However, these compounds are not claimed in the present Patent Document, and the substituents at the 12-position as described in the present Patent Document are various substituents other than a vinyl group or an ethyl group. Further, there has been not reported a mutilin derivative having a structural feature in which a 1,4-dihydro-4-oxo-3-quinolonecarboxylic acid structure, a 1,4-dihydro-4-oxo-3-naphthylidinecarboxylic acid structure, or a pyridobenzoxazine structure, which is a heterocyclic aromatic ring carboxylic acid structure, is bonded via an acylcarbamoyl bond and a piperidine ring in a substituent at the 14-position as shown in the present Patent Document.

On the other hand, the production of the following mutilin derivatives for attaining an antimicrobial activity has been reported. Specifically, a mutilin 14-carbamate derivative (Non-Patent Document 7) has been known, and a compound having a naturally occurring vinyl group or an ethyl group resulting from the reduction of the vinyl group at the 12-position and a carbamoyl derivative at the 14-position, as described in the Non-Patent documents, is known. However, there have been no reports of a mutilin derivative having a structural feature in which a 1,4-dihydro-4-oxo-3-quinolonecarboxylic acid structure, a 1,4-dihydro-4-oxo-3-naphthylidinecarboxylic acid structure, or a pyridobenzoxazine structure, which is a heterocyclic aromatic ring carboxylic acid structure, is bonded via an acylcarbamoyl bond and a piperidine ring in a substituent at the 14-position as described in the present Patent Document.

Patent Document 1: Pamphlet of WO 1997025309, WO 1998005659
Patent Document 2: Pamphlet of WO 1999021855
Patent Document 3: Pamphlet of WO 1999051219
Patent Document 4: Pamphlet of WO 2000007974
Patent Document 5: Pamphlet of WO 2000027790
Patent Document 6: Pamphlet of WO 2000037074
Patent Document 7: Pamphlet of WO 2000073287
Patent Document 8: Pamphlet of WO 2001009095
Patent Document 9: Pamphlet of WO 2001014310
Patent Document 10: Pamphlet of WO 2001074788
Patent Document 11: Pamphlet of WO 2002004414
Patent Document 12: Pamphlet of WO 2002012199
Patent Document 13: Pamphlet of WO 2002022580
Patent Document 14: Pamphlet of WO 2002030929
Patent Document 15: Pamphlet of WO 2004089886
Patent Document 16: Pamphlet of WO 2007000001
Patent Document 17: Pamphlet of WO 2007000004
Patent Document 18: Pamphlet of WO 2007014409
Patent Document 19: Pamphlet of WO 2006070671
Patent Document 20: JP-A-2006-306727
Non-Patent Document 1: Kavanagh, F. et al., Proc. Natl. Acad. Sci. USA 1951, 37, 570-574.
Non-Patent Document 2: Knauseder, F. et al., J. Antibiot. 1976, 29, 125-131.
Non-Patent Document 3: Berner, H. et al., Tetrahedron 1981, 37, 915-919.
Non-Patent Document 4: Berner, H. et al., Tetrahedron 1983, 39, 1745-1748.
Non-Patent Document 5: Berner, H. et al., Monatsch. Chem. 1986, 117, 1073-1080.
Non-Patent Document 6: Birch, A. J. et al., Tetrahedron 1966, Suppl. 8, Part II, 359-387.
Non-Patent Document 7: Brooks, G. et al., Bioorg. Med. Chem. 2001, 9, 1221-1231.
Non-Patent Document 8: Green, T. W.; Wuts, P. G. M. "Protective Groups in Organic Synthesis", 2nd Ed., Wiley Interscience Publication, John-Weiley & Sons, New York, 1991.
Non-Patent Document 9: Berner, H. et al., Tetrahedron 1980, 36, 1807-1811.
Non-Patent Document 10: J. Med. Chem. 1991, 34, 2726-2735.
Non-Patent Document 11: Tetrahedron Lett. 1991, 32, 1241-1244.
Non-Patent Document 12: J. Med. Chem. 1992, 35, 911.
Non-Patent Document 13: J. Chem. Soc. Perkin I. 1991, 1091-1097.
Non-Patent Document 14: J. Org. Chem. 2001, 66, 2526-2529.
Non-Patent Document 15: J. Org. Chem. 1962, 27, 3317.
Non-Patent Document 16: Chem. Ber. 1986, 119, 83.
Non-Patent Document 17: J. Gen. Chem. USSR, 1977, 2061-2067.
Non-Patent Document 18: J. Org. Chem. 1962, 27, 3742.

DISCLOSURE OF THE INVENTION

Problem to be Solved by the Invention

It is an object of the present invention to provide a mutilin derivative having a heterocyclic aromatic ring carboxylic acid structure in a substituent at the 14-position, which is a novel mutilin analogue exhibiting a potent and broad antimicrobial action against Gram-positive or Gram-negative bacteria including various resistant bacteria, and which is expected to be useful as an agent for treating infectious diseases as well as an intermediate for the production of the same.

Means for Solving the Problem

Taking into consideration the above-described problems, the present inventors have made extensive studies, and as a result, they have found that the following compound of the present invention has a potent antimicrobial action with few side-effects, and is useful, and therefore, they have completed the present invention.

Namely, the invention relates to a mutilin derivative represented by the following general formula (1):

[Chem. 2]

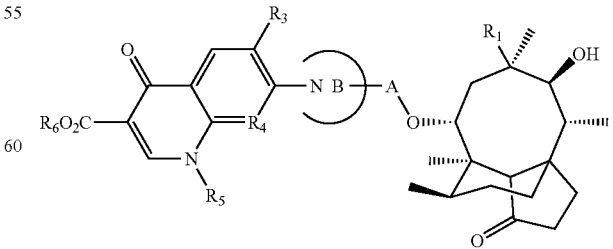

(1)

[wherein $R_1$ represents a hydrogen atom, a formyl group, a lower alkyl group which may be substituted, a lower alkenyl group which may be substituted, a lower alkynyl group which may be substituted, an aralkyl group whose aromatic ring may be substituted, a heteroaralkyl group whose aromatic ring may be substituted, a lower alkyloxycarbonyl group, a hydroxyl group which may be substituted, a thiol group which may be substituted, or an amino group which may be substituted, A represents the following chemical formula:

[Chem. 3]

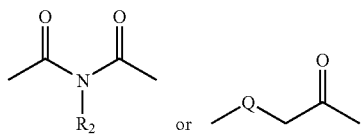

(wherein $R_2$ represents a hydrogen atom or a lower alkyl group which may be substituted, Q represents a nitrogen atom which may be substituted, an oxygen atom, or a sulfur atom), the ring B containing a nitrogen atom represents the following chemical formula:

[Chem. 4]

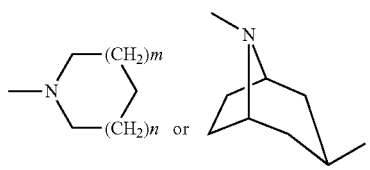

(wherein m and n represent 0 or 1, respectively), $R_3$ represents a hydrogen atom or a fluorine atom, $R_4$ represents CH, N, or the formula:

C—X or COR$_7$ (wherein X represents a halogen atom, and $R_7$ represents a hydrogen atom or a lower alkyl group which may be substituted), $R_5$ represents a lower alkyl group which may be substituted, a lower alkenyl group which may be substituted, an aralkyl group whose aromatic ring may be substituted, a heteroaralkyl group whose aromatic ring may be substituted, an aromatic ring which may be substituted, or an aromatic heterocyclic ring which may be substituted, or $R_5$ and $R_7$ may be combined to form a ring, and in this case, a lower alkyl group which may be substituted may be substituted at an arbitrary carbon atom, and $R_6$ represents a hydrogen atom, a lower alkyl group which may be substituted, or boric acid group which may be substituted], or a pharmaceutically acceptable addition salt thereof, or an agent for treating infectious diseases, comprising, as an active ingredient, the mutilin derivative or pharmaceutically acceptable addition salt thereof.

Advantage of the Invention

The compound according to the present invention is a novel mutilin derivative having an excellent antimicrobial action, and is effective against infectious diseases involving Gram-positive bacteria and Gram-negative bacteria including various drug-resistant bacteria.

BEST MODE FOR CARRYING OUT THE INVENTION

In the present invention, the "lower alkyl group" of "lower alkyl group which may be substituted" means a linear or branched alkyl group having 1 to 8 carbon atoms or a cyclic alkyl group having 3 to 8 carbon atoms, and in particular, a linear or branched alkyl group having 1 to 6 carbon atoms or a cyclic alkyl group having 3 to 6 carbon atoms. Examples of the substituent of the "lower alkyl group which may be substituted" include a lower alkoxy group, a lower alkoxy-lower alkoxy group, a lower cycloalkyl group, an aralkyloxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, a 5- to 14-membered aliphatic heterocyclic ring that may have at least one substituent and that may contain at least one hetero atom selected from the group consisting of an oxygen atom, a nitrogen atom, and a sulfur atom, a 5- to 14-membered aromatic heterocyclic ring that may have at least one substituent and that may contain at least one hetero atom selected from the group consisting of an oxygen atom, a nitrogen atom, and a sulfur atom, and the like. The "amino group" in this case may be substituted with acyl, for example, acetyl or the like or may be substituted with one or two lower alkyl groups.

The lower acyl group means a linear or branched acyl group having 1 to 6 carbon atoms, and examples thereof include a formyl group, an acetyl group, a propylcarbonyl group, and the like.

The lower alkylcarbonyl group means a linear or branched alkylcarbonyl group having 2 to 7 carbon atoms or a cyclic alkylcarbonyl group having 4 to 7 carbon atoms, and examples thereof include an acetyl group, an ethylcarbonyl group, a propylcarbonyl group, a butylcarbonyl group, an isobutylcarbonyl group, a cyclobutylcarbonyl group, and the like.

The "lower alkenyl group" of "lower alkenyl group which may be substituted" means a linear or branched alkenyl group having 2 to 6 carbon atoms, and examples thereof include ethenyl, propenyl, 2-propenyl, butenyl, 2-butenyl, and the like. Examples of the "substituent" of the "lower alkenyl group which may be substituted" include a lower alkoxy group, an aralkyloxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, a 5- to 14-membered aliphatic heterocyclic ring that may have at least one substituent and that may contain at least one hetero atom selected from the group consisting of an oxygen atom, a nitrogen atom, and a sulfur atom, a 5- to 14-membered aromatic heterocyclic ring that may have at least one substituent and that may contain at least one hetero atom selected from the group consisting of an oxygen atom, a nitrogen atom, and a sulfur atom, and the like. The "amino group" in this case may be substituted with acyl, for example, acetyl or the like or may be substituted with one or two lower alkyl groups.

The "lower alkynyl group" of the "lower alkynyl group which may be substituted" means a linear or branched alkynyl group having 2 to 6 carbon atoms, and examples thereof include ethynyl, propynyl, 2-propynyl, butynyl, 2-butynyl, and the like. Examples of the "substituent" of the "lower alkynyl group which may be substituted" include a lower alkoxy group, an aralkyloxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, a 5- to 14-membered aliphatic heterocyclic ring that may have at least one substituent and that may contain at least one hetero atom selected from the group consisting of an oxygen atom, a nitrogen atom, and a sulfur atom, a 5- to 14-membered aromatic heterocyclic ring that may have at least one substituent and that may contain at least one hetero atom selected from the group consisting of an oxygen atom, a nitrogen atom, and a sulfur atom, and the like. The "amino group" in this case may be substituted with acyl, for example, acetyl or the like or may be substituted with one or two lower alkyl groups.

The "aralkyl group" of the "aralkyl group whose aromatic ring may be substituted" means, for example, a benzyl group, a 1-phenylethyl group, and the like, and examples of the substituent include a lower alkyl group, a lower alkoxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, and the like. The "amino group" in this case may be substituted with acyl, for example, acetyl or the like or may be substituted with one or two lower alkyl groups.

The "heteroaralkyl group" of the "heteroaralkyl group whose aromatic ring may be substituted" means a lower alkyl group bonded to a 5- to 14-membered aromatic heterocyclic ring containing at least one hetero atom selected from the group consisting of an oxygen atom, a nitrogen atom, and a sulfur atom, and the aromatic heterocyclic ring may form a condensed ring with benzene or a 5- or 6-membered aromatic heterocyclic ring. Examples thereof include thiazolylmethyl, pyrazolylmethyl, pyridinylmethyl, pyrazinylmethyl, pyrimidinylmethyl, pyridazinylmethyl, oxazolylmethyl, imidazolylmethyl, triazinylmethyl, benzothiazolylmethyl, benzoxazolylmethyl, benzoimidazolylmethyl, pyridothiazolylmethyl, quinolinylmethyl, and the like. Examples of the "substituent" of the "heteroaralkyl group whose aromatic ring may be substituted" include a lower alkyl group, a lower alkoxy group, an aralkyloxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, a 5- to 14-membered aliphatic heterocyclic ring that may have at least one substituent and that may contain at least one hetero atom selected from the group consisting of an oxygen atom, a nitrogen atom, and a sulfur atom, a 5- to 14-membered aromatic heterocyclic ring that may have at least one substituent and that may contain at least one hetero atom selected from the group consisting of an oxygen atom, a nitrogen atom, and a sulfur atom, and the like. The "amino group" in this case may be substituted with acyl, for example, acetyl or the like or may be substituted with one or two lower alkyl groups.

The "lower alkyloxycarbonyl group" means a linear or branched alkoxycarbonyl group having 1 to 6 carbon atoms or a cyclic alkoxycarbonyl group having 3 to 6 carbon atoms, and examples thereof include a methoxycarbonyl group, ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a cyclopropoxycarbonyl group, a cyclobutoxycarbonyl group, and the like. Examples of the substituent of the "lower alkoxycarbonyl group" include a lower alkoxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, and the like. The "amino group" in this case may be substituted with acyl, for example, acetyl or the like or may be substituted with one or two lower alkyl groups.

The "hydroxyl group which may be substituted" means a hydroxyl group, a lower alkoxy group, a lower acyloxy group, a hydroxyl group having a protective group, an arylacyloxy group, a hydroxyl group to be a leaving group including the oxygen atom, or the like.

The "lower alkoxy group" means a linear or branched alkoxy group having 1 to 6 carbon atoms, and examples thereof include a methoxy group, an ethoxy group, a 1-methylethoxy group, a 11-dimethylethoxy group, a propoxy group, a 2-methylpropoxy group, and the like. Examples of the substituent include a lower alkyl group, a lower alkoxy group, an aralkyloxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, a 5- to 14-membered aliphatic heterocyclic ring that may have at least one substituent and that may contain at least one hetero atom selected from the group consisting of an oxygen atom, a nitrogen atom, and a sulfur atom, a 5- to 14-membered aromatic heterocyclic ring that may have at least one substituent and that may contain at least one hetero atom selected from the group consisting of an oxygen atom, a nitrogen atom, and a sulfur atom, and the like. The "amino group" in this case may be substituted with acyl, for example, acetyl or the like or may be substituted with one or two lower alkyl groups.

The "lower acyloxy group" means an acyloxy group having 1 to 5 carbon atoms, and examples thereof include a formyloxy group, an acetoxy group, a propionyloxy group, a 2,2-dimethylpropionyloxy group, and the like.

The "arylacyl group" means an aryl-(acyl group having 1 to 5 carbon atoms), and examples thereof include a benzoyl group, and the like. As its substituent, it may have lower alkyl group(s), lower alkoxy group(s), halogen atom(s), cyano group(s), nitro group(s), or the like.

Examples of the protective group for a hydroxyl group include a trialkylsilyl group such as a trimethylsilyl group, a t-butyldimethylsilyl group, and the like, an arylmethyl group such as a benzyl group, a diphenylmethyl group, and the like, an acyl group such as an acetyl group, a propionyl group, and the like, a lower alkoxymethyl group such as a methoxymethyl group, an ethoxymethyl group, and the like, an aralkyloxymethyl group such as a benzyloxymethyl group, and the like, a tetrahydropyranyl group, and the like. The introduction and removal of the group can be carried out by employing an appropriate method as described in the literature (Green, T. W.; Wuts, P. G. M. "Protective Groups in Organic Synthesis", $2^{nd}$ Ed., Wiley Interscience Publication, John-Weiley & Sons, New York, 1991. Hereinafter, this literature is simply referred to as "Green, et al.").

Examples of the "leaving group including the oxygen atom" include a lower alkylsulfonyloxy group, an arylsulfonyloxy group, and the like.

The "lower alkylsulfonyloxy group" means a linear or branched alkylsulfonyloxy group having 1 to 6 carbon atoms, and examples thereof include a methylsulfonyloxy group, an ethylsulfonyloxy group, and the like.

The "arylsulfonyloxy group" means a monocyclic or polycyclic aromatic ring sulfonyloxy group such as benzene and naphthalene, and examples thereof include a phenylsulfonyloxy group, a p-toluenesulfonyloxy group, and the like.

The "thiol group which may be substituted" means a thiol group, a lower alkylthio group which may be substituted, an aralkylthio group whose aromatic ring may be substituted, an arylthio group whose aromatic ring may be substituted, a heteroarylthio group whose aromatic ring may be substituted, a lower acylthio group, an arylacylthio group, a thiol group having a protective group, or the like, and its sulfur atom may be oxidized with one or two oxygen atoms.

The "lower alkylthio group" means a linear or branched alkylthio group having 1 to 6 carbon atoms or a cyclic alkylthio group having 3 to 6 carbon atoms, and examples thereof include a methylthio group, an ethylthio group, a propylthio group, an isopropylthio group, a butylthio group, an isobutylthio group, a sec-butylthio group, a tert-butylthio group, a cyclopropylthio group, a cyclobutylthio group, and the like.

Examples of the substituent of the "lower alkylthio group which may be substituted" include a lower alkoxy group, a halogen atom, a cyano group, an amino group, a hydroxyl group, a thiol group, a lower acyloxy group which may be substituted, a lower alkyloxycarbonyl group which may be substituted, a lower alkylcarbonyl group which may be substituted, a lower alkylcarboxamide group which may be substituted, a nitro group, and the like. The "amino group" in this case may be substituted with acyl, for example, acetyl or the like or may be substituted with one or two lower alkyl groups.

The "aralkylthio group" of the "aralkylthio group whose aromatic ring may be substituted" includes a benzylthio group, a 1-phenylethylthio group, and the like, and examples of its substituent include a lower alkyl group, a lower alkoxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, and the like. The "amino group" in this case may be substituted with acyl, for example, acetyl or the like or may be substituted with one or two lower alkyl groups.

Examples of the substituent of the "arylthio group whose aromatic ring may be substituted" include a lower alkyl group, a lower alkoxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, and the like. The "amino group" in this case may be substituted with acyl, for example, acetyl or the like or may be substituted with one or two lower alkyl groups.

The "heteroaryl" of the "heteroarylthio group whose aromatic ring may be substituted" refers to a 5- to 14-membered aromatic heterocyclic ring containing at least one hetero atom selected from the group consisting of an oxygen atom, a nitrogen atom, and a sulfur atom, and the aromatic heterocyclic ring may form a condensed ring with benzene or a 5- or 6-membered aromatic heterocyclic ring. Examples thereof include thiazolyl, pyrazolyl, pyridinyl, pyrazinyl, pyrimidinyl, pyridazinyl, oxazolyl, imidazolyl, triazinyl, benzothiazolyl, benzoxazolyl, benzoimidazolyl, pyridothiazolyl, quinolinyl, and the like. Examples of the substituent of the "heteroarylthio group whose aromatic ring may be substituted" include a lower alkyl group, a lower alkoxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, and the like. The "amino group" in this case may be substituted with acyl, for example, acetyl or the like or may be substituted with one or two lower alkyl groups.

Examples of the "lower acylthio group" include those having 1 to 5 carbon atoms such as an acetylcithio group, a propionylthio group, a 2,2-dimethylpropionylthio group, and the like.

The "arylacyl" of the "arylacylthio group whose aromatic ring may be substituted" means an aryl-(acyl group having 1 to 5 carbon atoms), and examples thereof include a benzoyl group, and the like. Examples of its substituent include lower alkyl group(s), lower alkoxy group(s), halogen atom(s), cyano group(s), nitro group(s), or the like.

Examples of the protective group for a thiol group include a trialkylsilyl group such as a trimethylsilyl group, a t-butyldimethylsilyl group, and the like, an arylmethyl group such as a benzyl group, a diphenylmethyl group, and the like, an acyl group such as an acetyl group, a propionyl group, and the like, a lower alkoxymethyl group such as a methoxymethyl group, an ethoxymethyl group, and the like, an aralkyloxymethyl group such as a benzyloxymethyl group, and the like, a tetrahydropyranyl group, and the like. The introduction and removal of the group can be carried out by employing an appropriate method as described in the literature (Green, et al.).

The expression "the sulfur atom may be oxidized with one or two oxygen atoms" refers to a lower alkylsulfinyl group, an aralkylsulfinyl group which may be substituted, an arylsulfinyl group whose aromatic ring may be substituted, a heteroarylsulfinyl group which may be substituted, a lower alkyl sulfonyl group, an aralkylsulfonyl group which may be substituted, an arylsulfonyl group whose aromatic ring may be substituted, or a heteroarylsulfonyl group which may be substituted, and examples thereof include, in case of the sulfinyl group, a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a cyclopropylsulfinyl group, a cyclobutylsulfinyl group, a benzylsulfinyl group, a 1-phenylethylsulfinyl group, a phenylsulfinyl group, a thiazolylsulfinyl group, a pyrazolylsulfinyl group, a pyridinylsulfinyl group, a pyrazinylsulfinyl group, a pyrimidinylsulfinyl group, a pyridazinylsulfinyl group, an oxazolylsulfinyl group, an imidazolylsulfinyl group, a triazinylsulfinyl group, a benzothiazolylsulfinyl group, a benzoxazolylsulfinyl group, a benzoimidazolylsulfinyl group, a pyridothiazolylsulfinyl group, and a quinolinylsulfinyl group, and in the case of the sulfonyl group, a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a cyclopropylsulfonyl group, a cyclobutylsulfonyl group, a benzylsulfonyl group, a 1-phenylethylsulfonyl group, a phenylsulfonyl group, a thiazolylsulfonyl group, a pyrazolylsulfonyl group, a pyridinylsulfonyl group, a pyrazinyl sulfonyl group, a pyrimidinylsulfonyl group, a pyridazinyl sulfonyl group, an oxazolylsulfonyl group, an imidazolylsulforiyl group, a triazinylsulfonyl group, a benzothiazolylsulfonyl group, a benzoxazolylsulfonyl group, a benzoimidazolylsulfonyl group, a pyridothiazolylsulfonyl group, a quinolinylsulfonyl group, and the like.

The "amino group which may be substituted" means an amino group, a lower alkyl amino group, a lower acylamino group, an amino group having protective group(s), an arylacylamino group, or the like.

Examples of the "protective group for an amino group" include a lower acyl group such as acetyl, propionyl, and the like, a lower alkoxycarbonyl group such as ethoxycarbonyl, t-butoxycarbonyl, and the like, a benzyl group, and the like. The introduction and removal of the group can be carried out by employing an appropriate method as described in the literature (Green, et al.).

The "arylacyl group" means an aryl-(acyl group having 1 to 5 carbon atoms), and examples thereof include a benzoyl group, and the like. It may have lower alkyl group(s), lower alkoxy group(s), halogen atom(s), cyano group(s), nitro group(s), or the like as its substituent.

Examples of the "substituent" of the "nitrogen atom which may be substituted" include a lower alkyl group, a lower alkoxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, and the like. The "amino group" in this case may be substituted with acyl, for example, acetyl or the like or may be substituted with one or two lower alkyl groups.

The "halogen atom" means a fluorine atom, a chlorine atom, a bromine atom, or an iodine atom.

The "aromatic ring" of the "aromatic ring which may be substituted" means a monocyclic or polycyclic aromatic ring such as benzene and naphthalene, and examples of the "substituent" of the "aromatic ring which may be substituted" include a lower alkyl group, a lower alkoxy group, an aralkyloxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, a 5- to 14-membered aliphatic heterocyclic ring that may have at least one substituent and that may contain at least one hetero atom selected from the group consisting of an oxygen atom, a nitrogen atom, and a sulfur atom, a 5- to 14-membered aromatic heterocyclic ring that may have at least one substituent and that may contain at least one hetero atom selected from the group consisting of an oxygen atom, a nitrogen atom, and a sulfur atom, and the like. The "amino group" in this case may be substituted with acyl, for example, acetyl or the like or may be substituted with one or two lower alkyl groups.

The "aromatic heterocyclic ring" of the "aromatic heterocyclic ring which may be substituted" means a 5- to 14-membered aromatic heterocyclic ring containing at least one hetero atom selected from the group consisting of an oxygen atom, a nitrogen atom, and a sulfur atom, and the aromatic heterocyclic ring may form a condensed ring with benzene or a 5- or 6-membered aromatic heterocyclic ring. Examples thereof include thiazolyl, pyrazolyl, pyridinyl, pyrazinyl, pyrimidinyl, pyridazinyl, oxazolyl, imidazolyl, triazinyl, benzothiazolyl, benzoxazolyl, benzoimidazolyl, pyridothiazolyl, quinolinyl, and the like.

Examples of the "substituent" of the "aromatic heterocyclic ring which may be substituted" include a lower alkyl group, a lower alkoxy group, an aralkyloxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, a 5- to 14-membered aliphatic heterocyclic ring that may have at least one substituent and that may contain at least one hetero atom selected from the group consisting of an oxygen atom, a nitrogen atom, and a sulfur atom, a 5- to 14-membered aromatic heterocyclic ring that may have at least one substituent and that may contain at least one hetero atom selected from the group consisting of an oxygen atom, a nitrogen atom, and a sulfur atom, and the like. The "amino group" in this case may be substituted with acyl, for example, acetyl or the like or may be substituted with one or two lower alkyl groups. The "aliphatic heterocyclic ring" of the aliphatic heterocyclic ring which may be substituted means a 5- to 14-membered aliphatic heterocyclic ring containing at least one hetero atom selected from the group consisting of an oxygen atom, a nitrogen atom, and a sulfur atom, and examples thereof include tetrahydrofuranyl, tetrahydropyranyl, pyrrolidinyl, piperidinyl, piperazinyl, tetrahydrothiophenyl, tetrahydrothiopyranyl, morpholinyl, and the like. Examples of the "substituent" of the aliphatic heterocyclic ring which may be substituted include a lower alkyl group, a lower alkoxy group, an aralkyloxy group, a halogen atom, a cyano group, an amino group, a hydroxyl group, a thiol group, a lower acyloxy group, a lower alkyloxycarbonyl group, a lower alkylcarbonyl group, a lower alkylcarboxamide group, a nitro group, a 5- to 14-membered aliphatic heterocyclic ring that may have at least one substituent and that may contain at least one hetero atom selected from the group consisting of an oxygen atom, a nitrogen atom, and a sulfur atom, a 5- to 14-membered aromatic heterocyclic ring that may have at least one substituent and that may contain at least one hetero atom selected from the group consisting of an oxygen atom, a nitrogen atom, and a sulfur atom, and the like. The "amino group" in this case may be substituted with acyl, for example, acetyl or the like or may be substituted with one or two lower alkyl groups.

The ring formed by the combination of $R_5$ and $R_7$ means a 5- to 14-membered hetero ring formed by the combination of a carbon atom and a nitrogen atom which are adjacent to each other, and preferably $R_5$-$R_7$ represents —CH($R_{5A}$)CH$_2$O— or —CH($R_{5A}$)CH$_2$CH$_2$— (wherein $R_{5A}$ represents a hydrogen atom or a lower alkyl group which may be substituted). Examples thereof include pyrido[1,2,3-de][1,4]benzoxazine having substituent(s) at a 2 position, and the like.

Examples of the "lower alkyl group which may be substituted" that is the substituent of the ring formed by the combination of $R_5$ and $R_7$ include, a lower alkyl group substituted with lower alkoxy group(s), halogen atom(s), cyano group(s), amino group(s), hydroxyl group(s), thiol group(s), lower acyloxy group(s), lower alkyloxycarbonyl group(s), lower alkylcarbonyl group(s), lower alkylcarboxamide group(s), phosphoric acid group(s) which may be substituted with lower alkyl group(s), nitro group(s) or the like, and others, in addition to a lower alkyl group.

Examples of the "boric acid group which may be substituted" include boric acid group whose hydroxyl group is substituted with lower acyl group(s) such as acetyl group(s) and propionyl group(s).

Examples of the preferable compound in the present invention include:

14-[1-(3-carboxy-1-cyclopropyl-1,4-dihydro-6-fluoro-4-oxoquinolin-7-yl)piperidine-4-carbonyl]carbamoylmutilin, 14-[1-(3-carboxy-1-cyclopropyl-1,4-dihydro-6-fluoro-4-oxoquinolin-7-yl)piperidine-4-carbonyl]carbamoyl-12-desethenyl-12-methylthiomutilin, 14-(1-{3-[2-(4-morpholyl)ethoxycarbonyl]-1-cyclopropyl-1,4-dihydro-6-fluoro-4-oxoquinolin-7-yl}piperidine-4-carbonyl)carbamoyl-12-desethenyl-12-methylthiomutilin hydrochloride, 14-(1-{3-[2-(Dimethylamino)ethoxycarbonyl]-1-cyclopropyl-1,4-dihydro-6-fluoro-4-oxoquinolin-7-yl}piperidine-4-carbonyl)carbamoyl-12-desethenyl-12-methylthiomutilin hydrochloride, 14-[1-(3-carboxy-1,4-dihydro-1-ethyl-6-fluoro-4-oxoquinolin-7-yl)piperidine-4-carbonyl]carbamoylmutilin, 14-[1-(3-carboxy-6,8-difluoro-1-ethyl-1,4-dihydro-6-fluoro-4-oxoquinolin-7-yl)piperidine-4-carbonyl]carbamoylmutilin, 14-[1-(3-carboxy-6,8-difluoro-1,4-dihydro-1-(2-fluoroethyl)-4-oxoquinolin-7-yl)piperidine-4-carbonyl]carbamoylmutilin, 14-{1-[3-carboxy-1,4-dihydro-6-fluoro-1-(2-fluoroethyl)-4-oxoquinolin-7-yl]piperidine-4-carbonyl}carbamoylmutilin, 14-{1-[3-carboxy-1,4-dihydro-6-fluoro-1-(2-fluoroethyl)-8-methoxy-4-oxoquinolin-7-yl]piperidine-4-carbonyl}carbamoylmutilin, 14-[1-(6-carboxy-2,3-dihydro-9-fluoro-7-oxo-7H-pyrido[1,2,3-de][1,4]benzoxazin-10-yl)piperidine-4-carbonyl]carbamoylmutilin, 14-{1-[3-carboxy-1-(2,4-difluorophenyl)-1,4-dihydro-6-fluoro-4-oxoquinolin-7-yl]piperidine-4-carbonylcarbamoyl}mutilin,
14-[1-(3-carboxy-1-cyclopropyl-6,8-difluoro-1,4-dihydro-4-oxoquinolin-7-yl)piperidine-4-carbonyl]carbamoylmutilin,
14-[1-(3-carboxy-8-chloro-1-cyclopropyl-1,4-dihydro-6-fluoro-4-oxoquinolin-7-yl)piperidine-4-carbonyl]carbamoylmutilin,
14-[1-(3-carboxy-1-cyclopropyl-1,4-dihydro-6-fluoro-4-oxo-1,8-naphthylidin-7-yl)piperidine-4-carbonyl]carbamoylmutilin,
14-(1-{3-carboxy-1,4-dihydro-6-fluoro-1-[(1R,2 S)-2-fluorocyclopropan-1-yl]-4-oxoquinolin-7-yl}piperidine-4-carbonyl)carbamoylmutilin,
14-(1-{3-carboxy-1,4-dihydro-6-fluoro-1-[(1R,2S)-2-fluorocyclopropan-1-yl]-4-oxo-1,8-naphthylidin-7-yl}piperidine-4-carbonyl)carbamoylmutilin,
14-(1-{3-carboxy-6,8-difluoro-1,4-dihydro-1-[(1R,2 S)-2-fluorocyclopropan-1-yl]-4-oxoquinolin-7-yl}piperidine-4-carbonyl)carbamoylmutilin,
14-(1-{3-carboxy-1,4-dihydro-6-fluoro-1-[(1R,2S)-2-fluorocyclopropan-1-yl]-8-methoxy-4-oxoquinolin-7-yl}piperidine-4-carbonyl)carbamoylmutilin,
14-(1-{3-carboxy-1-cyclopropyl-1,4-dihydro-8-difluoromethoxy-6-fluoro-1-[(1R,2S)-2-fluorocyclopropan-1-yl]-4-oxoquinolin-7-yl}piperidine-4-carbonyl)carbamoylmutilin,
14-(1-{3-carboxy-1,4-dihydro-1-[(1R,2S)-2-fluorocyclopropan-1-yl]-8-methoxy-4-oxoquinolin-7-yl}piperidine-4-carbonyl)carbamoylmutilin,
14-{1-[3-carboxy-1,4-dihydro-1-(1,1-dimethylethyl)-6-fluoro-4-oxo-1,8-naphthylidin-7-yl]piperidine-4-carbonyl}carbamoylmutilin,
14-[1-(3-carboxy-1-cyclopropyl-1,4-dihydro-8-fluoro-4-oxoquinolin-7-yl)piperidine-4-carbonyl]carbamoylmutilin,
14-{1-[(3S)-6-carboxy-2,3-dihydro-9-fluoro-3-methyl-7-oxo-7H-pyrido[1,2,3-de][1,4]benzoxazin-10-yl]piperidine-4-carbonyl}carbamoylmutilin,
14-{1-[(3R)-6-carboxy-2,3-dihydro-9-fluoro-3-fluoromethyl-7-oxo-7H-pyrido[1,2,3-de][1,4]benzoxazin-10-yl]piperidine-4-carbonyl}carbamoylmutilin,
14-{1-[(3S)-6-carboxy-2,3-dihydro-3-methyl-7-oxo-7H-pyrido[1,2,3-de][1,4]benzoxazin-10-yl]piperidine-4-carbonyl}carbamoylmutilin,
14-{1-[(3R)-6-carboxy-2,3-dihydro-3-fluoromethyl-7-oxo-7H-pyrido[1,2,3-de][1,4]benzoxazin-10-yl]piperidine-4-carbonyl}carbamoylmutilin,
14-[1-(3-carboxy-1-cyclopropyl-1,4-dihydro-6-fluoro-8-methoxy-4-oxoquinolin-7-yl)piperidine-4-carbonyl]carbamoylmutilin,
14-{exo-8'-(1-cyclopropyl-1,4-dihydro-6-fluoro-4-oxoquinolin-7-yl)-8'-azabicyclo[3.2.1]octan-3-ylsulfanyl}acetoxymutilin,
14-[1-(3-carboxy-1,4-dihydro-1-ethyl-6-fluoro-4-oxoquinolin-7-yl)piperidine-4-carbonyl]carbamoyl-12-desethenyl-12-methylthiomutilin,
14-[1-(3-carboxy-6,8-difluoro-1,4-dihydro-1-ethyl-4-oxoquinolin-7-yl)piperidine-4-carbonyl]carbamoyl-12-desethenyl-12-methylthiomutilin,
14-[1-(3-carboxy-6,8-difluoro-1,4-dihydro-1-(2-fluoroethyl)-4-oxoquinolin-7-yl)piperidine-4-carbonyl]carbamoyl-12-desethenyl-12-methylthiomutilin,
14-{1-[3-carboxy-1,4-dihydro-6-fluoro-1-(2-fluoroethyl)-4-oxoquinolin-7-yl]piperidine-4-carbonyl}carbamoyl-12-desethenyl-12-methylthiomutilin,
14-{1-[3-carboxy-1,4-dihydro-6-fluoro-1-(2-fluoroethyl)-8-methoxy-4-oxoquinolin-7-yl]piperidine-4-carbonyl}carbamoyl-12-desethenyl-12-methylthiomutilin,
14-[1-(6-carboxy-2,3-dihydro-9-fluoro-7-oxo-7H-pyrido[1,2,3-de][1,4]benzoxazin-10-yl)piperidine-4-carbonyl]carbamoyl-12-desethenyl-12-methylthiomutilin,
14-{1-[3-carboxy-1-(2,4-difluorophenyl)-1,4-dihydro-6-fluoro-4-oxoquinolin-7-yl]piperidine-4-carbonyl}carbamoyl-12-desethenyl-12-methylthiomutilin,
14-[1-(3-carboxy-1-cyclopropyl-6,8-difluoro-1,4-dihydro-4-oxoquinolin-7-yl)piperidine-4-carbonyl]carbamoyl-12-desethenyl-12-methylthiomutilin,
14-[1-(3-carboxy-8-chloro-1-cyclopropyl-1,4-dihydro-6-fluoro-4-oxoquinolin-7-yl)piperidine-4-carbonyl]carbamoyl-12-desethenyl-12-methylthiomutilin,
14-[1-(3-carboxy-1-cyclopropyl-1,4-dihydro-6-fluoro-4-oxo-1,8-naphthylidin-7-yl)piperidine-4-carbonyl]carbamoyl-12-desethenyl-12-methylthiomutilin,
14-(1-{3-carboxy-1,4-dihydro-6-fluoro-1-[(1R,2S)-2-fluorocyclopropan-1-yl]-4-oxoquinolin-7-yl}piperidine-4-carbonyl)carbamoyl-12-desethenyl-12-methylthiomutilin,
14-(1-{3-carboxy-1,4-dihydro-6-fluoro-1-[(1R,2 S)-2-fluorocyclopropan-1-yl]-4-oxo-1,8-naphthylidin-7-yl}piperidine-4-carbonyl)carbamoyl-12-desethenyl-12-methylthiomutilin,
14-(1-{3-carboxy-6,8-difluoro-1,4-dihydro-1-[(1R,2S)-2-fluorocyclopropan-1-yl]-4-oxoquinolin-7-yl}piperidine-4-carbonyl)carbamoyl-12-desethenyl-12-methylthiomutilin,
14-(1-{3-carboxy-8-chloro-1,4-dihydro-6-fluoro-1-[(1R,2 S)-2-fluorocyclopropan-1-yl]-4-oxoquinolin-7-yl}piperidine-4-carbonyl)carbamoyl-12-desethenyl-12-methylthiomutilin,
14-(1-{3-carboxy-1,4-dihydro-6-fluoro-1-[(1R,2S)-2-fluorocyclopropan-1-yl]-8-methoxy-4-oxoquinolin-7-yl}piperidine-4-carbonyl)carbamoyl-12-desethenyl-12-methylthiomutilin,
14-(1-{3-carboxy-1-cyclopropyl-1,4-dihydro-8-difluoromethoxy-6-fluoro-1-[(1R,2 S)-2-fluorocyclopropan-1-yl]-4-oxoquinolin-7-yl}piperidine-4-carbonyl)carbamoyl-12-desethenyl-12-methylthiomutilin,
14-(1-{3-carboxy-1,4-dihydro-1-[(1R,2S)-2-fluorocyclopropan-1-yl]-8-methoxy-4-oxoquinolin-7-yl}piperidine-4-carbonyl)carbamoyl-12-desethenyl-12-methylthiomutilin,
14-{1-[3-carboxy-1,4-dihydro-1-(1,1-dimethylethyl)-6-fluoro-4-oxo-1,8-naphthylidin-7-yl]piperidine-4-carbonyl}carbamoyl-12-desethenyl-12-methylthiomutilin,
14-[1-(3-carboxy-1-cyclopropyl-1,4-dihydro-8-fluoro-4-oxoquinolin-7-yl)piperidine-4-carbonyl]carbamoyl-12-desethenyl-12-methylthiomutilin,
14-{1-[(3S)-6-carboxy-2,3-dihydro-9-fluoro-3-methyl-7-oxo-7H-pyrido[1,2,3-de][1,4]benzoxazin-10-yl]piperidine-4-carbonyl}carbamoyl-12-desethenyl-12-methylthiomutilin,
14-{1-[(3R)-6-carboxy-2,3-dihydro-9-fluoro-3-fluoromethyl-7-oxo-7,1-pyrido[1,2,3-de][1,4]benzoxazin-10-yl]piperidine-4-carbonyl}carbamoyl-12-desethenyl-12-methylthiomutilin,
14-{1-[(3S)-6-carboxy-2,3-dihydro-3-methyl-7-oxo-7H-pyrido[1,2,3-de][1,4]benzoxazin-10-yl]piperidine-4-carbonyl}carbamoyl-12-desethenyl-12-methylthiomutilin, 14-{1-[(3R)-6-carboxy-2,3-dihydro-3-fluoromethyl-7-oxo-7H-pyrido[1,2,3-de][1,4]benzoxazin-10-yl]piperidine-4-carbonyl}carbamoyl-12-desethenyl-12-methylthiomutilin, 14-[1-(3-carboxy-1-cyclopropyl-1,4-dihydro-6-fluoro-8-methoxy-4-oxoquinolin-7-yl)piperidine-4-carbonyl]carbamoyl-12-desethenyl-12-methylthiomutilin, and the like.

Moreover, in the present patent application, the numbering of positions in the compound is based on the mutilin chemistry as shown below, rather than the IUPAC nomenclature. That is, according to Non-Patent Document 3, mutilin is named "(1S,2R,3S,4S,6R,7R,8R,14R)-3,6-dihydroxy-2,4,7,14-tetramethyl-4-vinyl-tricyclo[5.4.3.0$^{1,8}$]tetradecan-9-one" according to the IUPAC nomenclature.

[Chem. 5]

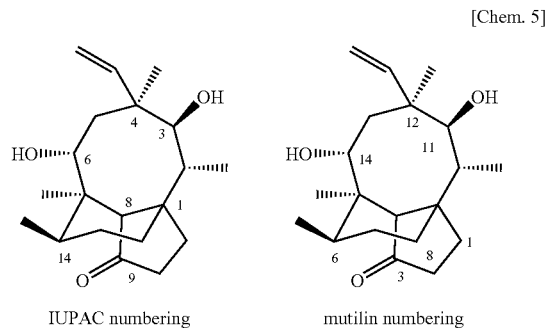

IUPAC numbering      mutilin numbering

On the other hand, the compound of the following general formula (7) is named "(1R,2R,4S,6R,7R,8S,9R,14R)-6-hydroxy-9-methoxy-2,4,7,14-tetramethyl-4-vinyl-1-tricyclo[5.4.3.0$^{1,8}$]tetradecan-3-one" according to the IUPAC nomenclature, but is named "(3R)-3-deoxo-11-deoxy-3-methoxy-11-oxo-4-epimutilin" according to mutilin chemistry.

[Chem. 6]

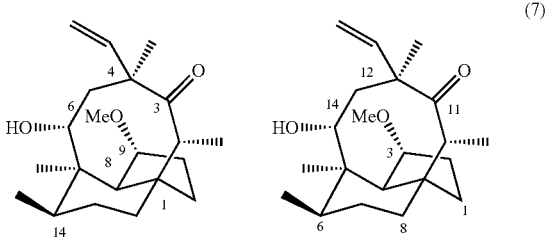

(7)

In the case where the compound of the present invention forms a pharmaceutically acceptable salt, the salts may be exemplified by addition salts with inorganic acids such as hydrochloric acid, hydrobromic acid, sulfuric acid, nitric acid, phosphoric acid, and the like, or organic acids such as acetic acid, maleic acid, fumaric acid, succinic acid, lactic acid, malic acid, tartaric acid, citric acid, methanesulfonic acid, p-toluenesulfonic acid, benzenesulfonic acid, salicylic acid, stearic acid, palmitic acid, trifluoroacetic acid, and the like.

The compounds of the present invention have a plurality of asymmetric carbon atoms, and may thus exist as a corresponding number of optical isomers. These optical isomers as well as mixtures comprising these isomers at any ratio are also encompassed by the present invention.

The compound of the present invention represented by the general formula (1) or a salt thereof include any intramolecular salts, adducts, solvates or hydrates thereof.

The compound represented by the general formula (1) of the present invention or a salt thereof can be used as a pharmaceutical composition either alone or in combination with one or more pharmaceutically acceptable adjuvants. Specifically, the compounds may be mixed with pharmaceutically acceptable carriers, excipients, lubricants, binders, disintegrating agents, diluents, or the like, and may be formulated as tablets, capsules, granules, powders, fine powders, ointments, ampoules, injections, or the like for oral or parenteral administration by a conventional method. While the dose may vary depending on the type of the compound represented by the general formula (1) of the present invention or a salt thereof, and the method of administration, as well as the age, weight or symptom of patients, the compound of the present invention represented by the general formula (1) or a salt thereof is typically administered to a mammal including humans, at a dose of 0.0001 to 1000 mg/kg/day. The administration is conducted, for example, in single or multiple doses per day.

The compound represented by the general formula (1) of the present invention can be prepared by the following process, for example, using a compound represented by the general formula (8) as a key intermediate, in accordance with Production Process A below. As mentioned herein, the compound represented by the following general formula (8), a compound represented by the following general formula (10), and a compound represented by the following general formula (10-1) are known compounds, and can be prepared, for example, with reference to the methods described in Patent Documents 19 and 20.

(Production Process A)

[Chem. 7]

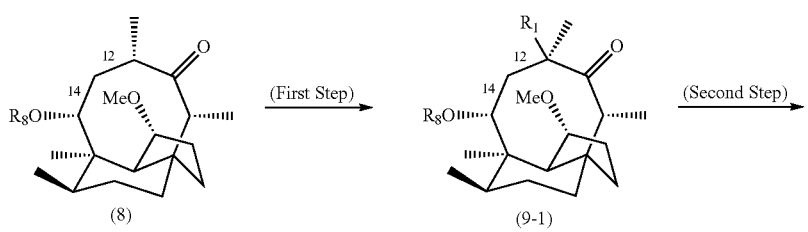

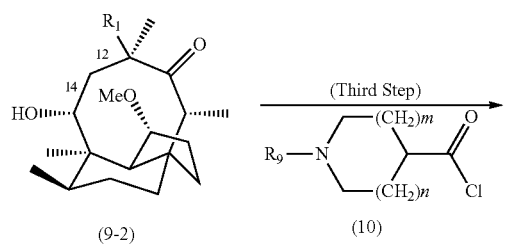

(9-2)

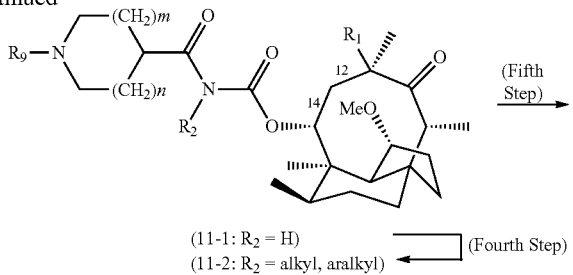

(Third Step)

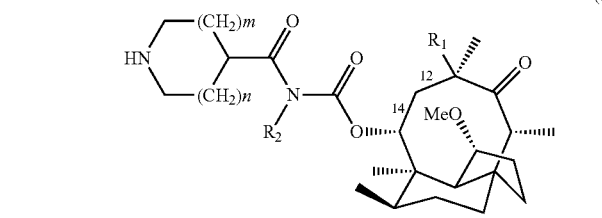

(10)

(11-1: R₂ = H)
(11-2: R₂ = alkyl, aralkyl)

(Fifth Step)

(Fourth Step)

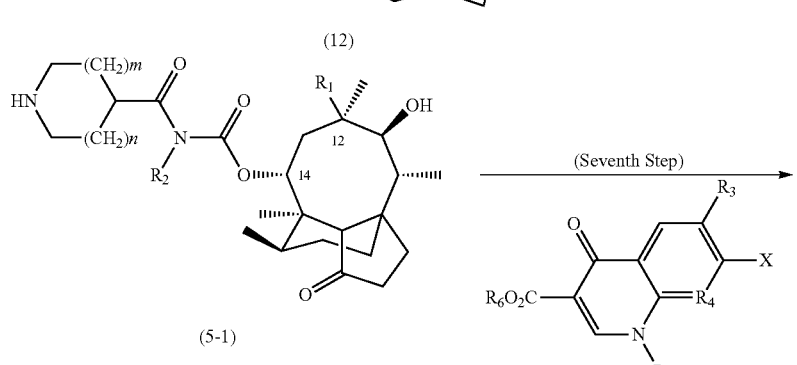

(12)

(Sixth Step)

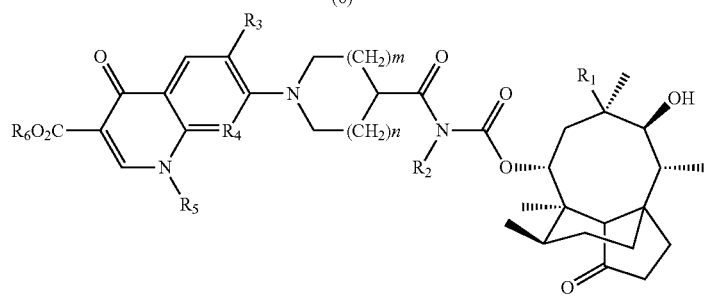

(5-1)

(6)

(Seventh Step)

(1)

(wherein $R_1$ represents a lower alkyl group which may be substituted, a lower alkenyl group which may be substituted, a lower alkynyl group which may be substituted, an aralkyl group whose aromatic ring may be substituted, a heteroaralkyl group whose aromatic ring may be substituted, a hydroxyl group which may be substituted, or a thiol group which may be substituted, X represents a halogen atom, $R_2$, $R_3$, $R_4$, $R_5$, $R_6$, m, and n are as defined above, $R_8$ represents a protective group for a hydroxyl group, and $R_9$ represents a protective group for a nitrogen atom).

(First Step)

This step aims to prepare a 4-epimutilin derivative having $R_1$ substituted at the 12-position represented by the general formula (9-1) by reacting an equal or excess amount of an appropriate electrophile, for example, lower halogenated alkyl, lower halogenated alkenyl, lower halogenated alkynyl, an oxidizing agent representatively exemplified by a Davis reagent, substituted alkyl, substituted aryl, substituted heteroaryl thiolsulfonate, or the like with the position 12 of the 4-epimutilin derivative having desethenyl at the 12-position represented by the general formula (8) in the presence of a base.

As the Davis reagent, 3-phenyl-2-phenylsulfonyloxaziridines which can be prepared by the method described in the literature (J. Org. Chem. 1982, 47, 1774), or the like, or optical active forms thereof, or optical active forms of (10-camphorsulfonyl)oxaziridine may be suitably used. Further, as the alkyl, aryl or heteroaryl thiolsulfonates, S-methyl p-toluenethiosulfonate, S-propyl p-toluenethiosulfonate, S-butyl p-toluenethiosulfonate, S-pentane p-toluenethiosulfonate, S-(2-fluoro)ethane p-toluenethiosulfonate, S-(2-t-butyldimethylsilyloxy)ethane p-toluenethiosulfonate, S-(2-propene) p-toluenethiosulfonate, 5-(1-methyl)ethane p-toluenethiosulfonate, S-benzene p-toluenethiosulfonate, S-(4-chloro)benzene p-toluenethiosulfonate, S-(2-pyridine) p-toluenethiosulfonate, or the like that can be prepared by the method described in the literature (Synthesis 2002, 343), and the like may be suitably used.

This reaction can be carried out in the presence of an appropriate reactive agent, for example, alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, or an inorganic base such as potassium carbonate, sodium hydrogen carbonate, and the like. Further, when necessary, the reaction can be carried out in the presence of a Lewis acid such as zinc chloride, zinc bromide, zinc iodide, boron trifluoride, aluminum chloride, tin tetrachloride, a boron trifluoride-diethyl ether complex, lithium perchlorate, and the like. As the solvent, any solvent that is not involved in the reaction may be used, and for example, hydrocarbon solvents, such as pentane, hexane, cyclohexane, benzene, toluene and xylene, halogenated hydrocarbon solvents, such as dichloromethane, 1,2-dichloroethane, chloroform, and carbon tetrachloride, ether solvents, such as diethyl ether, tetrahydrofuran, 1,4-dioxane and dimethoxyethane, or aprotic polar solvents such as acetonitrile, N,N-dimethylformamide, N,N-dimethylacetamide, dimethylsulfoxide, and the like may be suitably used. The reaction proceeds smoothly at −110° C. to 100° C.

A 4-epimutilin derivative having desethenyl at the 12-position represented by the following general formula (9-6) in which $R_1$ is a mercapto group can also be prepared from a 4-epimutilin derivative having desethenyl at the 12-position represented by the general formula (9-1) in which $R_1$ is a methylthio group by the Production Process B below.

[Chem. 8]

(Production Process B)

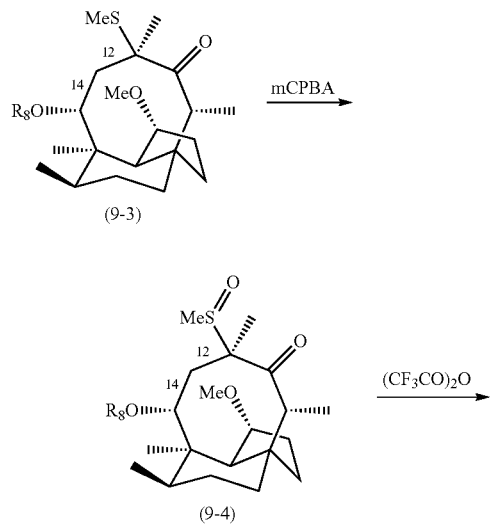

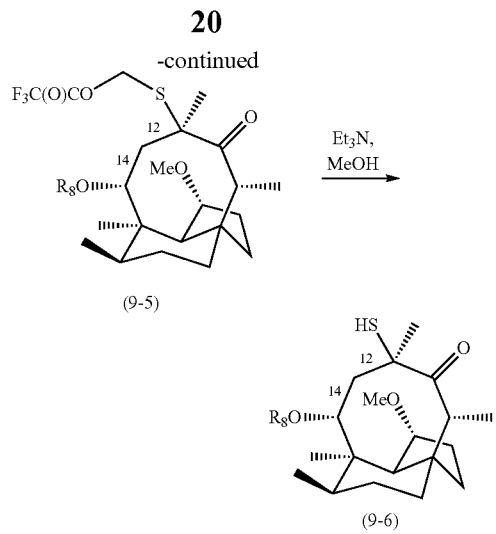

(wherein $R_8$ represents a protective group for a hydroxyl group)

That is, a 4-epimutilin derivative having desethenyl at the 12-position represented by the general formula (9-3) in which $R_1$ is a methylthio group is made into a sulfoxide form (9-4) through an oxidation reaction, then made into a sulfide derivative (9-5) using a trifluoroacetic anhydride, and the like through a Pummerer rearrangement reaction, and further subjected to a reaction under an alkaline condition to prepare a 4-epimutilin derivative having desethenyl at the 12-position represented by the general formula (9-6) in which $R_1$ is a mercapto group by the method described in the literature (Tetrahedron Lett. 1984, 25, 1753). For the oxidation reaction of sulfide, a general oxidation condition can be used, and for example, peroxides such as peracetic acid, benzoylperacetic acid, aqueous hydrogen peroxide, and the like, oxidants such as m-chloroperbenzoic acid, and the like, a Davis reagent, or the like can be used. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or aprotic polar solvents such as N,N-dimethylformamide, N,N-dimethylacetamide, dimethylsulfoxide, and the like, or a mixed solvent thereof with water may be suitably used. The reaction proceeds smoothly at −110° C. to 100° C. The subsequent Pummerer rearrangement reaction can be carried out in accordance with the method described in the literature (Ber. 1910, 43, 1401; Org. React. 1991, 40, 157). The reaction for producing a mercapto group under an alkaline condition is carried out in the presence of a common base, for example, alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo [4.3.0]nona-5-ene, 1,8-diazabicyclo[5.4.0]unde-7-cene, and the like, inorganic bases such as potassium carbonate, sodium hydrogen carbonate, and the like, and others. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, or ether-based solvents such as diethyl ether, tetrahydrofuran, 1,4-dioxane, dimethoxyethane, and the like are used. The reaction proceeds smoothly at −100° C. to 100° C.

In the case of the 4-epimutilin derivative having desethenyl at the 12-position represented by the general formula (9-1) in which $R_1$ is a hydroxyl group or a thiol group, the 4-epimutilin derivative having desethenyl at the 12-position represented by the general formula (9-1) in which $R_1$ is a lower alkoxy group or a lower alkylthio group can be prepared by a common etherification reaction. In this case, the reaction can be usually carried out using an equal or excess amount of an appropriate electrophile, for example, halogenated lower alkyl representatively exemplified by methyl iodide and the like, in the presence of an appropriate reagent, for example, alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, and inorganic bases such as potassium carbonate, sodium hydrogen carbonate, and the like. Further, the reaction can be carried out, when necessary, in the presence of Lewis acids such as zinc chloride, zinc bromide, zinc iodide, boron trifluoride, aluminum chloride, tin tetrachloride, a boron trifluoride-diethyl ether complex, lithium perchlorate, and the like. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or aprotic polar solvents such as acetonitrile, N,N-dimethylformamide, N,N-dimethylacetamide, dimethylsulfoxide, and the like may be suitably used. The reaction proceeds smoothly at −110° C. to 100° C.

(Second Step)

This step aims to prepare a 4-epimutilin derivative having hydroxyl at the 14-position represented by the general formula (9-2) by removing the protective group for a hydroxyl group at the 14-position from the 4-epimutilin derivative having $R_1$ substituted at the 12-position represented by the general formula (9-1). The method for removing the protective group for a hydroxyl group can be carried out by suitably employing a method described in the literature (Green, et al.). For example, in the case where a methoxy methyl group is selected as the protective group, pyridinium p-toluenesulfonate or the like may be suitably used. As the solvent, any solvent that is not involved in the reaction can be used, and examples thereof include a hydrocarbon solvent such as pentane, hexane, cyclohexane, benzene, toluene, xylene, and the like, a halogenated hydrocarbon solvent such as dichloromethane, 1,2-dichloroethane, chloroform, carbon tetrachloride, and the like, an ether solvent such as diethyl ether, tetrahydrofuran, 1,4-dioxane, dimethoxyethane, and the like, or an alcohol solvent such as methanol, ethanol, 1-propanol, 2-propanol, 1-butanol, 2-butanol, 2-methyl-1-propanol, 2-methyl-2-propanol, and the like may be suitably used. The reaction proceeds smoothly at −110° C. to 100° C.

(Third Step)

This step aims to prepare a 4-epimutilin derivative which is acylcarbamoylated at the 14-position, represented by the general formula (11-1), by reacting the hydroxyl group at the 14-position in the 4-epimutilin derivative having hydroxyl at the 14-position represented by the general formula (9-2) with the cyclic amine carboxylic acid halide derivative represented by the general formula (10) or the like to carry out the acylcarbamoylation under an appropriate reaction condition.

This step can be usually carried out with reference to the method described in the literature. That is, (A) a method of reacting the cyclic amine carboxylic acid halide derivative represented by the general formula (10) and silver cyanate with the 4-epimutilin derivative having hydroxyl at the 14-position represented by the general formula (9-2) in the presence of an appropriate base (J. Org. Chem. 1962, 27, 3317) or a method of using tributyltin isocyanate (Chem. Ber. 1986, 119, 83), (B) a method of carrying out a carbamoylation reaction on the hydroxyl group at the 14-position of the 4-epimutilin derivative having hydroxyl at the 14-position represented by the general formula (9-2) under a normal reaction condition, and then coupling the cyclic amine carboxylic acid halide derivative represented by the general formula (10) in the presence of an appropriate base, (C) a method of reacting the 4-epimutilin derivative having hydroxyl at the 14-position represented by the general formula (9-2) with trimethylsilyl isocyanate and the cyclic amine carboxylic acid chloride derivative represented by the general formula (10) in the presence of an appropriate base (J. Gen. Chem. USSR, 1977, 2061-2067), or (D) a method of acid-amidating the carboxylic acid form which is a source compound of the cyclic amine carboxylic acid halide represented by the general formula (10) in the presence of an appropriate base under a normal reaction condition, and then reacting the 4-epimutilin derivative having hydroxyl at the 14-position represented by the general formula (9-2) with a carbonyl source, for example, a reagent such as oxalyl chloride, phosgene, CDI, and the like in the presence of an appropriate base such as a bis(trimethylsilyl)amide salt and the like (J. Org. Chem. 1962, 27, 3742), or other methods can be employed. The reaction is usually carried out in the presence of an appropriate base, for example, alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, inorganic bases such as potassium carbonate, sodium hydrogen carbonate, and the like, and others. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, or ether-based solvents such as diethyl ether, tetrahydrofuran, 1,4-dioxane, dimethoxyethane, and the like are used. The reaction proceeds smoothly at −110° C. to 100° C.

(Fourth Step)

This step aims to prepare a 4-epimutilin derivative which is acylcarbamoylated at the 14-position, represented by the general formula (11-2), by introducing a substituent represented by $R_2$ (except a hydrogen atom) into the nitrogen atom present at the spacer site at the 14-position of the 4-epimutilin derivative which is acylcarbamoylated at the 14-position, represented by the general formula (11-1). The reaction can be carried out, for example, in the presence of alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, inorganic bases such as potassium carbonate, sodium hydrogen carbonate, and the like, or others as the base used. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, alcohol-based solvents such as methanol, ethanol, 1-propanol, 2-propanol, 1-butanol, 2-butanol, 2-methyl-1-propanol, 2-methyl-2-propanol, and the like, or aprotic polar solvents such as N,N-dimethylformamide, N,N-dimethylacetamide, dimethylsulfoxide, and the like may be suitably used. The reaction proceeds smoothly at −110° C. to 100° C.

(Fifth Step)

This step aims to prepare a 4-epimutilin derivative which is acylcarbamoylated at the 14-position, represented by the general formula (12), by removing the protective group at the 1-position at a cyclic amine site in the 4-epimutilin derivative which is acylcarbamoylated at the 14-position, represented by the general formula (11-1 or 11-2), obtained in Fourth Step above. The removal of the protective group can be carried out by suitably employing a method described in the literature (Green, et al.). For example, in the case of selecting and using a t-butoxycarbonyl group as the protective group, a trifluoroacetic acid is used as a reagent or heating is conducted around 180° C., thereby carrying out deprotection. As the reaction solvent, any solvent that is not involved in the reaction may be used, and the reaction is carried out, for example, in the presence or absence of hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, aprotic polar solvents, such as acetonitrile, propionitrile, nitromethane, nitroethane, N,N-dimethylformamide, N,N-dimethylacetamide, dimethylsulfoxide, and the like, or a mixed solvent thereof with acetic acid or water. Usually, the reaction proceeds smoothly at −20° C. to 200° C.

(Sixth Step)

This step aims to prepare a mutilin derivative which is acylcarbamoylated at the 14-position, represented by the general formula (5-1), by removing the protective group at the 3-position in the 4-epimutilin derivative which is acylcarbamoylated at the 14-position, represented by the general formula (12). The removal of the protective group can be carried out by suitably employing a method described in the literature (Green, et al.). In the case where the protective group at the 3-position is a methyl group, hydrochloric acid or zinc chloride-hydrochloric acid (Lucas reagent) may be suitably used. As the reaction solvent, any solvent that is not involved in the reaction may be used, and the reaction is carried out, for example, in the presence or absence of hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, aprotic polar solvents, such as acetonitrile, propionitrile, nitromethane, nitroethane, N,N-dimethylformamide, N,N-dimethylacetamide, dimethylsulfoxide, and the like, or a mixed solvent thereof with water. Usually, the reaction proceeds smoothly at −20° C. to 200° C.

(Seventh Step)

This step aims to prepare a mutilin derivative which is acylcarbamoylated at the 14-position, represented by the general formula (1), by reacting the mutilin derivative which is acylcarbamoylated at the 14-position, represented by the general formula (5-1) with the heterocyclic aromatic ring carboxylic acid derivative represented by the general formula (6) in the presence of an appropriate base. The reaction can be prepared in the presence of, for example, alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, inorganic bases such as potassium carbonate, sodium hydrogen carbonate, and the like, or others as the base used. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, alcohol-based solvents such as methanol, ethanol, 1-propanol, 2-propanol, 1-butanol, 2-butanol, 2-methyl-1-propanol, 2-methyl-2-propanol, and the like, or aprotic polar solvents such as N,N-dimethylformamide, N,N-dimethylacetamide, dimethylsulfoxide, and the like may be suitably used. The reaction proceeds smoothly at −110° C. to 200° C.

Alternatively, the compound group represented by the general formula (5-2) of the present invention can also be prepared using pleuromutilin as a starting material, for example, according to Production Process C below. The compound represented by the following general formula (13) as mentioned herein is a known compound, and its preparation can be carried out, for example, with reference to the method described in Patent Documents 19 and 20.

[Chem. 9]

(Production Process C)

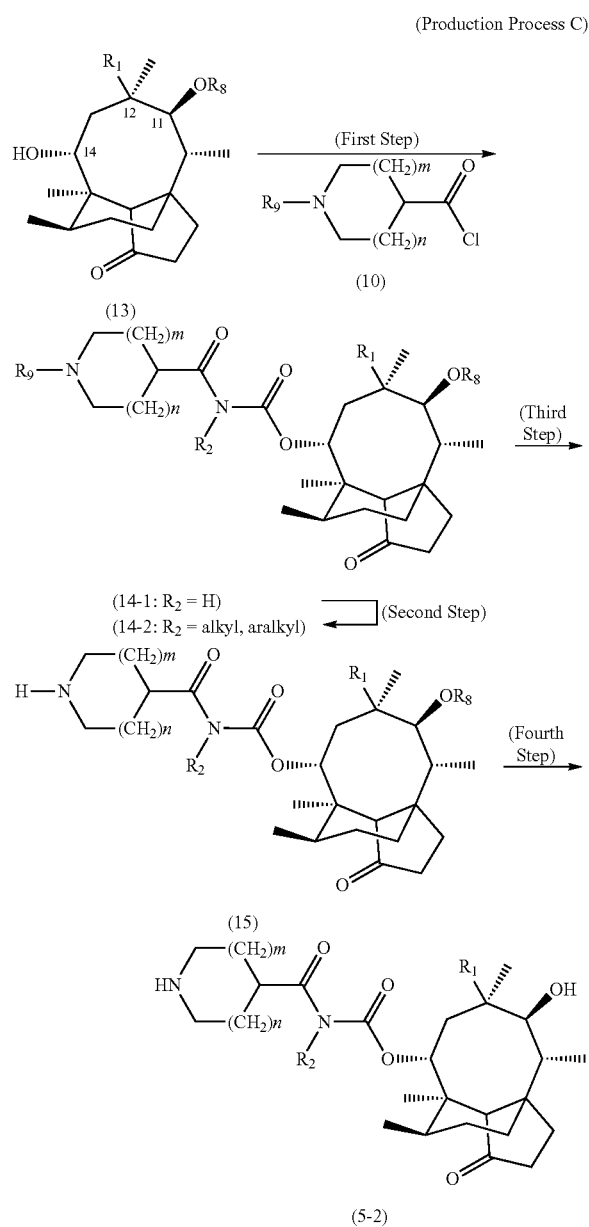

(wherein $R_1$ represents a formyl group, a lower alkyloxycarbonyl group, or an amino group which may be substituted, $R_2$ is as defined above, $R_8$ represents a protective group for a hydroxyl group, $R_9$ represents a protective group for a nitrogen atom, and m and n are as defined above).

(First Step)

This step aims to prepare a mutilin derivative which is acylcarbamoylated at the 14-position, in which the hydroxyl group at the 11-position is protected, represented by the general formula (14-1), by reacting the hydroxyl group at the 14-position in the mutilin derivative having $R_1$ substituted at the 12-position, in which the hydroxyl group at the 11-position is protected, represented by the general formula (13), with the cyclic amine carboxylic acid halide derivative represented by the general formula (10) to carry out the acylcarbamoylation reaction under an appropriate reaction condition.

This step can be usually carried out with reference to a method described in the literature. That is, (A) a method of reacting the cyclic amine carboxylic acid halide derivative represented by the general formula (10) and silver cyanate with the mutilin derivative having hydroxyl at the 14-position represented by the general formula (13), in which the hydroxyl group at the 11-position is protected, in the presence of an appropriate base (J. Org. Chem. 1962, 27, 3317) or a method of using tributyltin isocyanate (Chem. Ber. 1986, 119, 83), (B) a method of carrying out a carbamoylation reaction on the hydroxyl group at the 14-position of the mutilin derivative having hydroxyl at the 14-position, in which the hydroxyl group at the 11-position is protected, represented by the general formula (13) under a normal reaction condition, and then coupling the cyclic amine carboxylic acid chloride derivative represented by the general formula (10) in the presence of an appropriate base, (C) a method of reacting the mutilin derivative having hydroxyl at the 14-position, in which the hydroxyl group at the 11-position is protected, represented by the general formula (13), with trimethylsilyl isocyanate and the cyclic amine carboxylic acid halide derivative represented by the general formula (10) in the presence of an appropriate base (J. Gen. Chem. USSR, 1977, 2061-2067), or (D) a method of acid-amidating the carboxylic acid form which is a source compound of the cyclic amine carboxylic acid halide derivative represented by the general formula (10) in the presence of an appropriate base under a normal reaction condition, and then reacting the mutilin derivative having hydroxyl at the 14-position, in which the hydroxyl group at the 11-position is protected, represented by the general formula (13), with a carbonyl source, for example, a reagent such as oxalyl chloride, phosgene, CDI, and the like in the presence of an appropriate base such as a bis(trimethylsilyl)amide salt and the like (J. Org. Chem. 1962, 27, 3742), and other methods can be employed. The reaction is usually carried out in the presence of an appropriate base, for example, alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, inorganic bases such as potassium carbonate, sodium hydrogen carbonate, and the like, and others. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, or ether-based solvents such as diethyl ether, tetrahydrofuran, 1,4-dioxane, dimethoxyethane, and the like are used. The reaction proceeds smoothly at −110° C. to 100° C.

In the case where $R_1$ at the 12-position of the mutilin derivative which is acylcarbamoylated at the 14-position, in which the hydroxyl group at the 11-position is protected, represented by the general formula (14-1), is a nitrogen atom having a protective group, it can be deprotected under an appropriate reaction condition. The method for removing the protective group for a nitrogen atom can be carried out by suitably employing a method described in the literature (Green, et al.). For example, in the case of selecting and using a t-butoxycarbonyl group as the protective group for a nitrogen atom, a trifluoroacetic acid is used as a reagent or heating is conducted around 180° C., thereby carrying out deprotection. As the reaction solvent, any solvent that is not involved in the reaction may be used, and the reaction is carried out, for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, and the like, and aprotic polar solvents such as acetonitrile, propionitrile, nitromethane, nitroethane, N,N-dimethylformamide or dimethylsulfoxide, and the like may be suitably used. Usually, the reaction proceeds smoothly at −20° C. to 200° C.

Further, it is possible to introduce a new substituent after removing the protective group for a nitrogen atom. In the case, the mutilin derivative which is acylcarbamoylated at the 14-position, in which the hydroxyl group at the 11-position is protected, represented by the general formula (14-1), is prepared by a common reductive alkylation reaction, or by the reaction of an appropriate electrophile, for example, halogenated lower alkyl representatively exemplified by methyl iodide and the like, in the presence of a base. The reductive alkylation reaction can be carried out by the reaction of a reducing agent such as sodium cyanoborohydride, sodium borohydride, and the like in the presence of an aldehyde such as formaldehyde, acetaldehyde, and the like. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, alcohol-based solvents such as methanol, ethanol, 1-propanol, 2-propanol, 1-butanol, 2-butanol, 2-methyl-1-propanol, 2-methyl-2-propanol, and the like, or a mixed solvent thereof with water may be suitably used. Usually, the reaction proceeds smoothly at −110° C. to 200° C.

In the case of reacting an appropriate electrophile, for example, halogenated lower alkyl representatively exemplified by methyl iodide and the like, in the presence of a base, the reaction can be usually carried out using an equal or excess amount of an appropriate electrophile, in the presence of an appropriate reagent, for example, alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, and inorganic bases such as potassium carbonate, sodium hydrogen carbonate, and the like. Further, when necessary, the reaction can be carried out in the presence of Lewis acids such as zinc chloride, zinc bromide, zinc iodide, boron trifluoride, aluminum chloride, tin tetrachloride, a boron trifluoride-diethyl ether complex, lithium perchlorate, and the like. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or aprotic polar solvents such as N,N-dimethylformamide, N,N-dimethylacetamide, dimethylsulfoxide, and the like may be suitably used. The reaction proceeds smoothly at −110° C. to 200° C. Alternatively, it is possible to introduce a substituent using an appropriate catalyst in this step. In this case, for example, a method of using phenyl boric acid (Tetrahedron Lett. 2001, 42, 3415) and the like can be employed for N-phenylation.

(Second Step)

This step aims to prepare a mutilin derivative which is acylcarbamoylated at the 14-position, in which the hydroxyl group at the 11-position is protected, represented by the general formula (14-2) by introducing a substituent represented by $R_2$ (except a hydrogen atom) into the nitrogen atom present at the spacer site at the 14-position of the mutilin derivative which is acylcarbamoylated at the 14-position, in which the hydroxyl group at the 11-position is protected, represented by the general formula (14-1). The reaction can be carried out, for example, in the presence of alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, and inorganic bases such as potassium carbonate, sodium hydrogen carbonate, and the like as the base used. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, and the like, alcohol-based solvents such as methanol, ethanol, 1-propanol, 2-propanol, 1-butanol, 2-butanol, 2-methyl-1-propanol, 2-methyl-2-propanol, and the like, or aprotic polar solvents such as N,N-dimethylformamide, N,N-dimethylacetamide, dimethylsulfoxide, and the like may be suitably used. The reaction proceeds smoothly at −110° C. to 200° C.

(Third Step)

This step aims to prepare a mutilin derivative which is acylcarbamoylated at the 14-position, in which the hydroxyl group at the 11-position is protected, represented by the general formula (15), by removing the protective group at the 1-position at a cyclic amine site in the mutilin derivative which is acylcarbamoylated at the 14-position, in which the hydroxyl group at the 11-position is protected, represented by the general formula (14-1 or 14-2), obtained in Second Step above. The removal of the protective group can be carried out by suitably employing a method described in the literature (Green, et al.). For example, in the case of selecting and using a t-butoxycarbonyl group as the protective group for a nitrogen atom, a trifluoroacetic acid is used as a reagent or heating is conducted around 180° C., thereby carrying out deprotection. As the reaction solvent, any solvent that is not involved in the reaction may be used, and the reaction is carried out, for example, in the presence or absence of hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, aprotic polar solvents, such as acetonitrile, propionitrile, nitromethane, nitroethane, N,N- dimethylformamide, N,N-dimethylacetamide, dimethylsulfoxide, and the like or a mixed solvent thereof with acetic acid or water. Usually, the reaction proceeds smoothly at −20° C. to 200° C.

(Fourth Step)

This step aims to prepare a mutilin derivative which is acylcarbamoylated at the 14-position, represented by the general formula (5-2), by removing the protective group at the 11-position in the mutilin derivative which is acylcarbamoylated at the 14-position, in which the hydroxyl group at the 11-position is protected, represented by the general formula (15). The removal of the protective group can be carried out by suitably employing a method described in the literature (Green, et al.). As the reaction solvent, any solvent that is not involved in the reaction may be used, and the reaction is carried out, for example, in the presence or absence of hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, aprotic polar solvents, such as acetonitrile, propionitrile, nitromethane, nitroethane, N,N-dimethylformamide, N,N-dimethylacetamide, dimethylsulfoxide, and the like or a mixed solvent thereof with water. Usually, the reaction proceeds smoothly at −20° C. to 200° C.

Furthermore, the compound group represented by the general formula (5-3) of the present invention can be prepared using a compound represented by the chemical formula (9-2) as a key intermediate, for example, according to Production Process D below.

[Chem. 10]

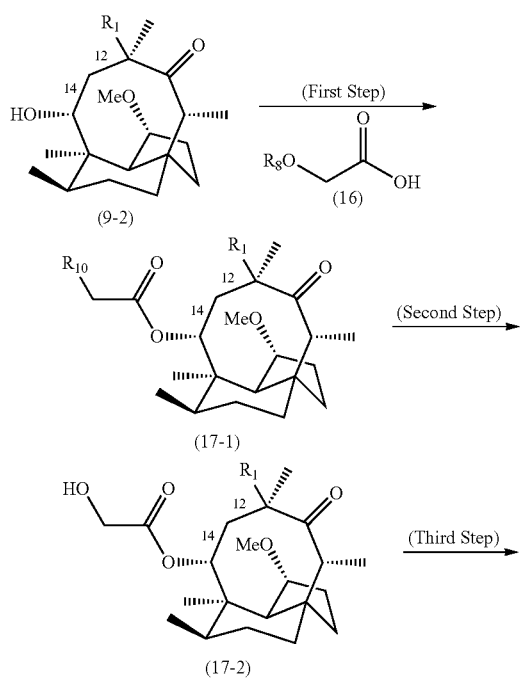

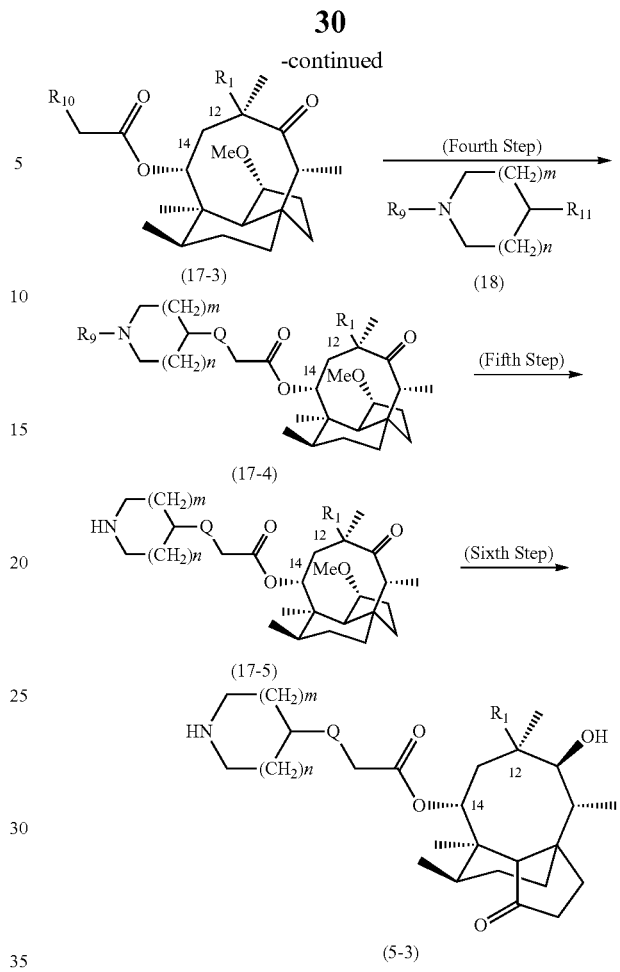

(wherein $R_1$ represents a lower alkyl group which may be substituted, a lower alkenyl group which may be substituted, a lower alkynyl group which may be substituted, an aralkyl group whose aromatic ring may be substituted, a heteroaralkyl group whose aromatic ring may be substituted, a hydroxyl group which may be substituted, or a thiol group which may be substituted, $R_8$ represents a protective group for a hydroxyl group, $R_9$ represents a protective group for a nitrogen atom, $R_{10}$ represents a leaving group, as combined with a hydroxyl group, or a halogen atom, $R_{11}$ represents a hydroxyl group, a thiol group, a primary amino group, or an amino group which may have a substituent other than a hydrogen atom, and Q, m and n are as defined above).

(First Step)

This step aims to prepare a 4-epimutilin derivative, in which the hydroxyl group at the 14-position is acylated, represented by the general formula (17-1), by reacting the 4-epimutilin derivative having hydroxyl at the 14-position represented by the general formula (9-2) with an acetic acid derivative (16) in the presence of an appropriate reagent.

This reaction can be carried out by suitably employing an appropriate condensing agent or an active esterification method, a mixed anhydride method, an acid chloride method, a carbodiimide method, or the like. Examples of the reagent used in the case of such a reaction include thionyl chloride, oxalyl chloride, N,N-dicyclohexylcarbodiimide, 1-methyl-2-bromopyridinium iodide, N,N'-carbonyldiimidazole, diphenylphosphoric chloride, diphenylphosphoric azide, N,N-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazo-1-yl-oxy-tris(dimethylamino)phosphonium hexafluorophosphate, and the like. In this step, a base or a condensing adjuvant may be used in combination with the above-described reagent. Any base that is not involved in the reaction may be used as the base used in this case, and the reaction can be carried out, for example, in the presence of alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, and inorganic bases such as potassium carbonate, sodium hydrogen carbonate, and the like. Further, as the condensing adjuvant, for example, N-hydroxybenzotriazole hydrate, N-hydroxysuccinimide, N-hydroxy 5-norbornene-2,3-dicarboxylmide, 3-hydroxy-3,4-dihydro-4-oxo-1,2,3-benzotriazole, and the like can be used. As the reaction solvent, any solvent that is not involved in the reaction may be used, for example hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, and the like, or aprotic polar solvents such as acetonitrile, propionitrile, nitromethane, nitroethane, N,N-dimethylformamide, N,N-dimethylacetamide, dimethylsulfoxide, and the like may be suitably used. Usually, the reaction proceeds smoothly at −20° C. to 200° C.

(Second Step)

This step aims to prepare a glycolic ester derivative represented by the general formula (17-2) by removing the protective group for a hydroxyl group in the 14-acylated-4-epimutilin derivative having a hydroxyl group protected, represented by the general formula (17-1).

The method for removing the protective group for a hydroxyl group can be carried out by suitably employing a method described in the literature (Green, et al.). For example, in the case of selecting and using an acetyl group as the protective group, sodium hydroxide, potassium hydroxide, sodium carbonate, potassium carbonate, or the like may be suitably used. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or alcohol-based solvents such as methanol, ethanol, 1-propanol, 2-propanol, 1-butanol, 2-butanol, 2-methyl-1-propanol, 2-methyl-2-propanol, and the like may be suitably used. The reaction proceeds smoothly at −110° C. to 100° C.

(Third Step)

This step aims to prepare a 4-epimutilin derivative, which is acylated at the 14-position, represented by the general formula (17-3), by converting a hydroxyl group of the glycolic ester derivative represented by the general formula (17-2) into $R_{10}$.

This reaction can be usually carried out in the presence of an appropriate reagent, for example, in the presence of halogenated lower alkyl sulfonyl or halogenated aryl sulfonyl, and in the presence of an appropriate base, for example alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, and inorganic bases such as potassium carbonate, sodium hydrogen carbonate, and the like. Further, when necessary, the reaction can be carried out in the presence of Lewis acids such as zinc chloride, zinc bromide, zinc iodide, boron trifluoride, aluminum chloride, tin tetrachloride, a boron trifluoride-diethyl ether complex, lithium perchlorate, and the like. In addition, in this step, subsequently, a 4-epimutilin derivative, in which $R_{10}$ is halogenated and has acylation at the 14-position, represented by the general formula (17-3) may also be prepared by the reaction of alkali metal halides such as sodium iodide, potassium iodide, and the like. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or aprotic polar solvents such as acetonitrile, propionitrile, nitromethane, nitroethane, N,N-dimethylformamide, N,N-dimethylacetamide, dimethylsulfoxide, and the like may be suitably used. The reaction proceeds smoothly at −110° C. to 100° C.

(Fourth Step)

This step aims to prepare a mutilin derivative, which is acylated at the 14-position, represented by the general formula (17-4), by reacting the 4-epimutilin derivative, which is acylated at the 14-position, represented by the general formula (17-3), with the cyclic amine derivative represented by the general formula (18).

This reaction can be carried out in the presence of an appropriate base, for example alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, and inorganic bases such as potassium carbonate, sodium hydrogen carbonate, and the like. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or aprotic polar solvents such as acetonitrile, propionitrile, nitromethane, nitroethane, N,N-dimethylformamide, N,N-dimethylacetamide, dimethylsulfoxide, and the like may be suitably used. The reaction proceeds smoothly at −110° C. to 100° C.

Furthermore, in this step, a mutilin derivative, which is acylated at the 14-position, represented by the general formula (17-4), can also be prepared by reacting the 4-epimutilin derivative, which is acylated at the 14-position represented by the general formula (17-2) with the cyclic amine derivative represented by the general formula (18) under the Mitsunobu reaction condition.

This reaction can be usually carried out in the presence of an appropriate reagent, for example, triphenylphosphine or tributylphosphine, using alkyl azodicarboxylate ester as a reagent. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or aprotic polar solvents such as acetonitrile, propionitrile, nitromethane, nitroethane, N,N-dimethylformamide, N,N-dimethylacetamide, dimethylsulfoxide, and the like may be suitably used. The reaction proceeds smoothly at −110° C. to 100° C.

(Fifth Step)

This step aims to prepare a 4-epimutilin derivative, which is acylated at the 14-position, represented by the general formula (17-5), by removing the protective group at the 1-position at a cyclic amine site in the 4-epimutilin derivative, which is acylated at the 14-position, represented by the general formula (17-4). The removal of the protective group can be carried out by suitably employing a method described in the literature (Green, et al.). For example, in the case of selecting and using a t-butoxycarbonyl group as the protective group for a nitrogen atom, a trifluoroacetic acid is used as a reagent or heating is conducted around 180° C., thereby carrying out deprotection. As the reaction solvent, any solvent that is not involved in the reaction may be used, and the reaction is carried out, for example, in the presence or absence of hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, aprotic polar solvents, such as acetonitrile, propionitrile, nitromethane, nitroethane, N,N-dimethylformamide, N,N-dimethylacetamide, dimethylsulfoxide, and the like, or a mixed solvent thereof with acetic acid or water. The reaction proceeds smoothly at −20° C. to 200° C.

(Sixth Step)

This step aims to prepare a mutilin derivative, which is acylated at the 14-position, represented by the general formula (5-3), by removing the protective group at the 3-position in the 4-epimutilin derivative, which is acylated at the 14-position represented by the general formula (17-5). The removal of the protective group can be carried out by suitably employing a method described in the literature (Green, et al.), and hydrochloric acid or zinc chloride-hydrochloric acid (Lucas reagent) may be suitably used. As the reaction solvent, any solvent that is not involved in the reaction may be used, and the reaction is carried out in the presence or absence of, for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, aprotic polar solvents, such as acetonitrile, propionitrile, nitromethane, nitroethane, N,N-dimethylformamide, N,N-dimethylacetamide, dimethylsulfoxide, and the like, or a mixed solvent thereof with water. Usually, the reaction proceeds smoothly at −20° C. to 200° C.

Alternatively, the compound group represented by the general formula (5-4) of the present invention can also be prepared using the compound of the general formula (13) as a starting material, for example, according to Production Process E below.

[Chem. 11]

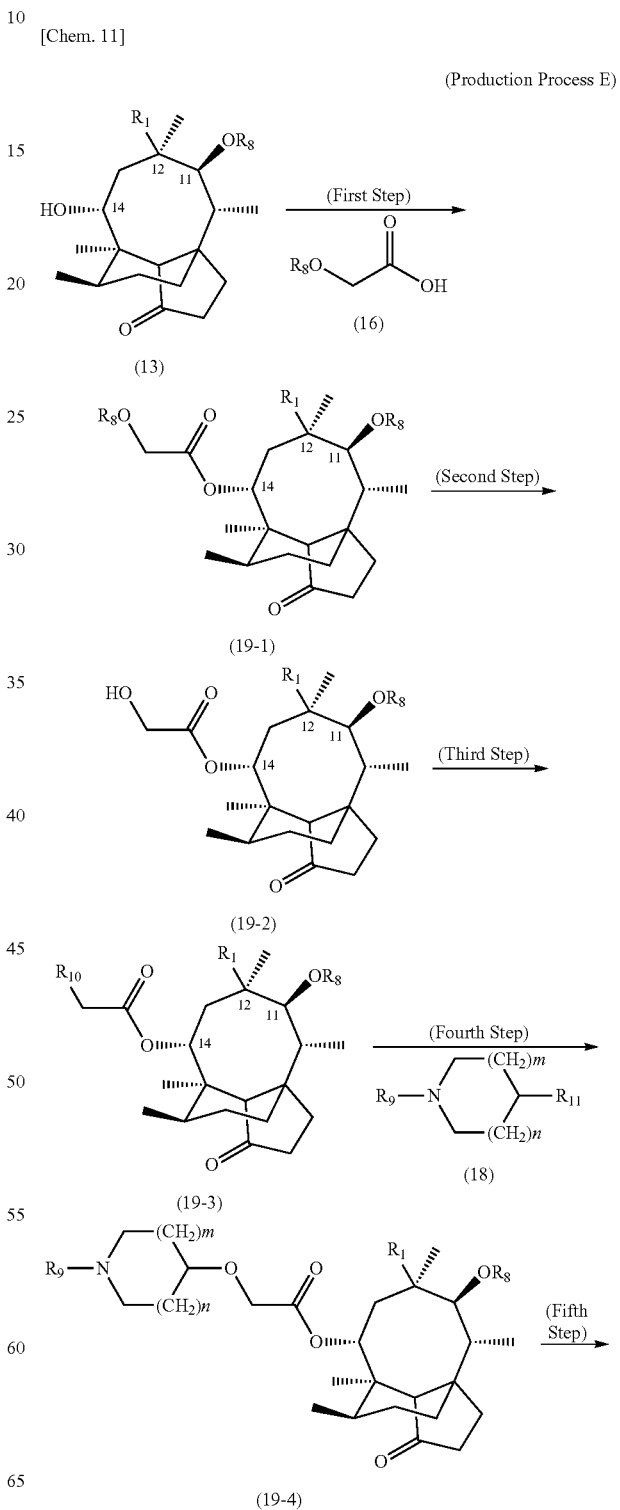

(Production Process E)

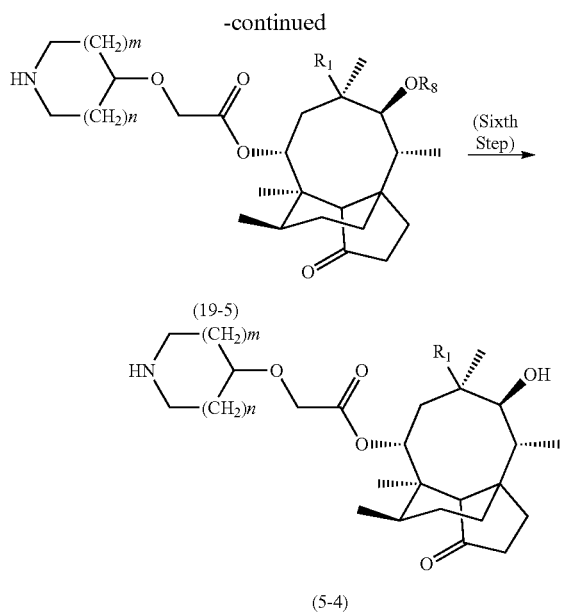

(wherein $R_1$ represents a formyl group, a lower alkyloxycarbonyl group, or an amino group which may be substituted, $R_8$ represents a protective group for a hydroxyl group, $R_9$ represents a protective group for a nitrogen atom, $R_{10}$ represents a leaving group, as combined with a hydroxyl group, or a halogen atom, $R_{11}$ represents a hydroxyl group, a thiol group, a primary amino group, or an amino group which may have a substituent other than a hydrogen atom, and Q, m and n are as defined above).

(First Step)

This step aims to prepare a mutilin derivative, in which the hydroxyl group at the 11-position is protected and the hydroxyl group at the 14-position is acylated, represented by the general formula (19-1), by reacting the mutilin derivative having hydroxyl at the 14-position, in which the hydroxyl group at the 11-position is protected, represented by the general formula (13), with an acetic acid derivative (16) in the presence of an appropriate reagent.

This reaction can be carried out by suitably employing an appropriate condensing agent or an active esterification method, a mixed anhydride method, an acid chloride method, a carbodiimide method, or the like. Examples of the reagent used in the case of such a reaction include thionyl chloride, oxalyl chloride, N,N-dicyclohexylcarbodiimide, 1-methyl-2-bromopyridinium iodide, N,N'-carbonyldiimidazole, diphenylphosphoric chloride, diphenylphosphoric azide, N,N-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazo-1-yl-oxy-tris(dimethylamino)phosphonium hexafluorophosphate, and the like. In this step, a base or a condensing adjuvant may be used in combination with the above-described reagent. In this case, any base that is not involved in the reaction may be used as the base, and the reaction can be carried out, for example, in the presence of alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, and inorganic bases such as potassium carbonate, sodium hydrogen carbonate, and the like. Further, as the condensing adjuvant, for example, N-hydroxybenzotriazole hydrate, N-hydroxysuccinimide, N-hydroxy 5-norbornene-2,3-dicarboxylmide, 3-hydroxy-3,4-dihydro-4-oxo-1,2,3-benzotriazole, and the like can be used. As the reaction solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, and the like, or aprotic polar solvents such as acetonitrile, propionitrile, nitromethane, nitroethane, N,N-dimethylformamide, N,N-dimethylacetamide, dimethylsulfoxide, and the like may be suitably used. Usually, the reaction proceeds smoothly at $-20°$ C. to $200°$ C.

(Second Step)

This step aims to prepare a glycolic ester derivative represented by the general formula (19-2) by selectively removing the protective group for a hydroxyl group involved in the glycolic ester site in the 14-acylated-mutilin derivative, in which the hydroxyl group at the 11-position is protected, represented by the general formula (19-1).

The method for removing the protective group for a hydroxyl group can be carried out by suitably employing a method described in the literature (Green, et al.). For example, in the case of selecting and using an acetyl group as the protective group for a hydroxyl group involved in a glycolic ester site, sodium hydroxide, potassium hydroxide, sodium carbonate, potassium carbonate, or the like may be suitably used. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or alcohol-based solvents such as methanol, ethanol, 1-propanol, 2-propanol, 1-butanol, 2-butanol, 2-methyl-1-propanol, 2-methyl-2-propanol, and the like may be suitably used. The reaction proceeds smoothly at $-110°$ C. to $100°$ C.

(Third Step)

This step aims to prepare a mutilin derivative, which is acylated at the 14-position, represented by the general formula (19-3), by selectively converting a hydroxyl group of the glycolic ester derivative represented by the general formula (19-2) into $R_{10}$.

This reaction can be usually carried out in the presence of an appropriate reagent, for example, halogenated lower alkyl sulfonyl, halogenated aryl sulfonyl, and in the presence of an appropriate base, for example alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, and inorganic bases such as potassium carbonate, sodium hydrogen carbonate, and the like. Further, when necessary, the reaction can be carried out in the presence of a Lewis acid such as zinc chloride, zinc bromide, zinc iodide, boron trifluoride, aluminum chloride, tin tetrachloride, a boron trifluoride-diethyl ether complex, lithium perchlorate, and the like. In addition, in this step, subsequently, a mutilin derivative, in which $R_{10}$ is halogenated and has acylation at the 14-position, represented by the general formula (19-3) may also be prepared by the reaction of alkali metal halides such as sodium iodide, potassium iodide, and the like. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or aprotic polar solvents such as acetonitrile, propionitrile, nitromethane, nitroethane, N,N-dimethylformamide, N,N-dimethylacetamide, dimethylsulfoxide, and the like may be suitably used. The reaction proceeds smoothly at −110° C. to 100° C.

(Fourth Step)

This step aims to prepare a mutilin derivative, which is acylated at the 14-position, represented by the general formula (19-4), by reacting $R_{10}$ of the mutilin derivative, which is acylated at the 14-position, represented by the general formula (19-3), with the cyclic amine derivative represented by the general formula (18).

This reaction can be carried out in the presence of an appropriate base, for example, alkali metal alkoxides such as sodium methoxide and sodium ethoxide, alkali metal hydrides such as sodium hydride and potassium hydride, alkali metal organic bases such as n-butyllithium, lithium diisopropylamide, lithium bis(trimethylsilyl)amide, sodium bis(trimethylsilyl)amide, and potassium bis(trimethylsilyl)amide, tertiary organic bases such as triethylamine, diisopropylethylamine, pyridine, N-methylmorpholine, imidazole, pyrrolidine, piperidine, 1,5-diazabicyclo[4.3.0]nona-5-ene, 1,8-diazabicyclo[5.4.0]unde-7-cene, and the like, and inorganic bases such as potassium carbonate, sodium hydrogen carbonate, and the like. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or aprotic polar solvents such as acetonitrile, propionitrile, nitromethane, nitroethane, N,N-dimethylformamide, N,N-dimethylacetamide, dimethylsulfoxide, and the like may be suitably used. The reaction proceeds smoothly at −110° C. to 100° C.

Furthermore, in this step, a mutilin derivative, which is acylated at the 14-position, represented by the general formula (19-4), can also be prepared by reacting the mutilin derivative, which is acylated at the 14-position, represented by the general formula (19-2) with the cyclic amine derivative represented by the general formula (18) under the Mitsunobu reaction condition.

This reaction can be usually carried out in the presence of an appropriate reagent, for example, triphenylphosphine or tributylphosphine, using alkyl azodicarboxylate ester as a reagent. As the solvent, any solvent that is not involved in the reaction may be used, and for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, or aprotic polar solvents such as acetonitrile, propionitrile, nitromethane, nitroethane, N,N-dimethylformamide, N,N-dimethylacetamide, dimethylsulfoxide, and the like may be suitably used. The reaction proceeds smoothly at −110° C. to 100° C.

(Fifth Step)

This step aims to prepare a mutilin derivative, which is acylated at the 14-position, represented by the general formula (19-5), by removing the protective group at the 1-position at a cyclic amine site in the mutilin derivative, which is acylated at the 14-position, represented by the general formula (19-4). The removal of the protective group can be carried out by suitably employing a method described in the literature (Green, et al.). For example, in the case of selecting and using a t-butoxycarbonyl group as the protective group for a nitrogen atom, a trifluoroacetic acid is used as a reagent or heating is conducted around 180° C., thereby carrying out deprotection. As the reaction solvent, any solvent that is not involved in the reaction may be used, and the reaction is carried out, for example, in the presence or absence of hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, aprotic polar solvents, such as acetonitrile, propionitrile, nitromethane, nitroethane, N,N-dimethylformamide, N,N-dimethylacetamide, dimethylsulfoxide, and the like or a mixed solvent thereof with acetic acid or water. The reaction proceeds smoothly at −20° C. to 200° C.

(Sixth Step)

This step aims to prepare a mutilin derivative, which is acylated at the 14-position, represented by the general formula (5-4), by removing the protective group for a hydroxyl group at the 11-position in a mutilin derivative having a hydroxyl group protected at the 11-position, which is acylated at the 14-position, represented by the general formula (19-5). The removal of the protective group can be carried out by suitably employing a method described in the literature (Green, et al.). As the reaction solvent, any solvent that is not involved in the reaction may be used, and the reaction is carried out in the presence or absence of, for example, hydrocarbon-based solvents such as pentane, hexane, cyclohexane, benzene, toluene, xylene, and the like, halogenated hydrocarbon-based solvents such as dichloromethane, 1,2-dichloroethane, chloroform, carbon tetrachloride, and the like, ether-based solvents such as diethyl ether, tetrahydrofuran, 1,4-dioxane, dimethoxyethane, and the like, aprotic polar solvents, such as acetonitrile, propionitrile, nitromethane, nitroethane, N,N-dimethylformamide, N,N-dimethylaceta-

EXAMPLES

Hereinbelow, the present invention will be described with reference to Examples and Reference Examples in detail, which are not intended to limit the scope of the present invention.

Reference Example 1

1-(2,2,2-Trichloroethoxycarbonyl)piperidine-4-carboxylic acid

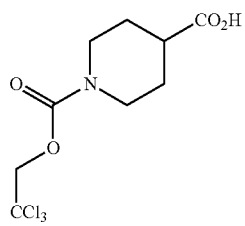

[Chem. 12]

To a solution (1000 mL) of ethyl isonipecotinate (100 g, 0.64 mol) and triethylamine (266 mL, 1.91 mol) in methylene chloride was added dropwise 2,2,2-trichloroethyl chloroformate (131 mL, 0.95 mol) while stirring under ice-cooling, followed by stirring for about 24 hours while naturally warming. To the reaction mixture was added N,N-dimethylaminopropanediamine (79.3 mL, 0.64 mol), followed by stirring for 30 minutes, and the solvent was evaporated under reduced pressure. To the residue was added a 10% aqueous citric acid solution, followed by extraction with ethyl acetate (1000 mL×3), and the combined organic layer was washed with saturated brine (1000 mL). The resultant was dried over anhydrous sodium sulfate and then filtered, and the solvent was evaporated. The residue was purified by silica gel column chromatography (hexane:ethyl acetate=10:1) to obtain 158 g of pale yellow oily ethyl 1-(2,2,2-trichloroethoxycarbonyl)piperidine-4-carboxylate (yield 74%).

MS (CI) (m/z): 332 (MH+).
HRMS (CI) (m/z): Calcd. for $C_{11}H_{17}Cl_3NO_4$ (MH+): 332.0223. Found, 332.0190.

Ethyl 1-(2,2,2-trichloroethoxycarbonyl)piperidine-4-carboxylate (158 g, 0.48 mol) was dissolved in a 2 N potassium hydroxide-ethanol solution (500 mL) and water (500 mL), followed by heating under reflux for about 1 hour. After cooling, to the reaction mixture was added water (300 mL), followed by extraction with ethyl acetate (300 mL×3). The aqueous layer was added a 10% aqueous citric acid solution, followed by extraction with ethyl acetate (500 mL×3), and the acidic fraction extracted was washed with saturated brine (300 mL). The resultant was dried over anhydrous sodium sulfate and then filtered, and the solvent was evaporated. The residue was washed with hexane to obtain 62.9 g of 1-(2,2,2-trichloroethoxycarbonyl)piperidine-4-carboxylic acid as a colorless crystal (yield 43%).

MS (CI) (m/z): 304 (MH+).
HRMS (CI) (m/z): Calcd. for $C_9H_{13}Cl_3NO_4$ (MH+): 303.9910. Found, 303.9937.

Reference Example 2

First Step (3R)-14-[1-(2,2,2-Trichloroethoxycarbonyl)piperidine-4-carbonyl]carbamoyl-3-deoxo-11-deoxy-3-methoxy-11-oxo-4-epimutilin

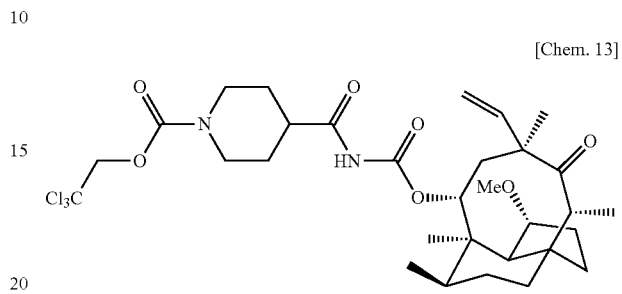

[Chem. 13]

To a solution (30 mL) of 4-epimutilin (1.00 g, 2.99 mmol) in methylene chloride was added silver cyanate (1.12 g, 7.48 mmol), and the acid chloride prepared from carboxylic acid (1.37 g, 4.49 mmol) of Reference Example 1 and oxalyl chloride, and triethylamine (0.63 mL, 4.49 mmol) were added thereto at −65° C. under an argon atmosphere, followed by stirring for about 4 hours while gradually warming. To the reaction mixture was added ethyl acetate (30 mL), followed by stirring and filtering over Celite. The filtrate was concentrated, and to the residue was added water (20 mL), followed by extraction with ethyl acetate (20 mL×3). The combined organic layer was washed with saturated brine (20 mL), dried over anhydrous sodium sulfate, and filtered, and the solvent was evaporated. The obtained residue was purified by silica gel column chromatography (hexane:ethyl acetate=3:1) to obtain 1.67 g of the heading compound as a colorless powdery crystal (yield 84%).

MS (ESI) (m/z): 661.2 (MH−).
HRMS (ESI) (m/z): Calcd. for $C_{31}H_{44}Cl_3N_2O_7$(MH−): 661.22141. Found, 661.21932.

Second Step (3R)-14-(1-Piperidine-4-carbonyl)carbamoyl-3-deoxo-11-deoxy-3-methoxy-11-oxo-4-epimutilin

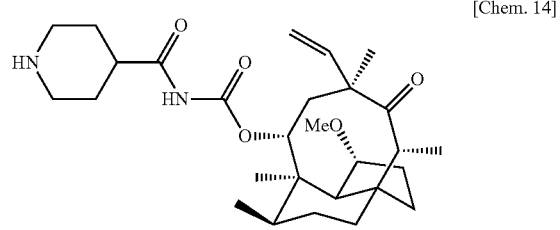

[Chem. 14]

To a solution (6 mL) of the compound of First Step (1.60 g, 2.41 mmol) in acetic acid was added zinc powder (791 mg, 12.1 mmol) under ice-cooling, followed by stirring at room temperature for about 24 hours. The reaction mixture was filtered over Celite, and the residue was washed with water and ethyl acetate. The combined filtrate was extracted with ethyl acetate (10 mL×3), and the combined organic layer was extracted with a 10% aqueous citric acid solution (15 mL×3). The aqueous layer was combined, alkalified with a saturated aqueous sodium hydrogen carbonate solution, and extracted with ethyl acetate (100 mL×3). The organic layer was washed with saturated brine (100 mL), dried over anhydrous sodium sulfate, and filtered, and the solvent was evaporated to obtain 995 mg of the heading compound as a pale yellow powdery crystal (yield 84%).

MS (ESI) (m/z): 489.3 (MH$^+$).

HRMS (ESI) (m/z): Calcd. for $C_{28}H_{45}N_2O_5$(MH$^+$): 489.33285. Found, 489.33387.

Third Step 14-(1-piperidine-4-carbonyl)carbamoylmutilin

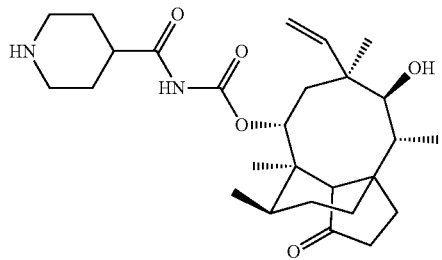

[Chem. 15]

To a solution (9.80 mL) of the compound of Second Step (980 mg, 2.01 mmol) in dioxane was added concentrated hydrochloric acid (9.80 mL) while stirring under ice-cooling, followed by stirring for about 4 hours while naturally warming. The mixed reaction liquid was alkalified with the addition of a saturated aqueous sodium hydrogen carbonate solution, and the aqueous layer was extracted with ethyl acetate (50 mL×6). The combined organic layer was washed with saturated brine (50 mL), dried over anhydrous sodium sulfate, and filtered, and the solvent was evaporated. The obtained residue was purified by silica gel column chromatography (NH, ethyl acetate, and then ethyl acetate:methanol=20:1) to obtain 518 mg of the heading compound as a colorless powdery crystal (yield 54%).

MS (ESI) (m/z): 475.3 (MH$^+$).

HRMS (ESI) (m/z): Calcd. for $C_{27}H_{43}N_2O_5$ (MH$^+$): 475.31720. Found, 475.31631.

Example 1

14-[1-(3-Carboxy-1-cyclopropyl-1,4-dihydro-6-fluoro-4-oxoquinolin-7-yl)piperidine-4-carbonyl]carbamoylmutilin

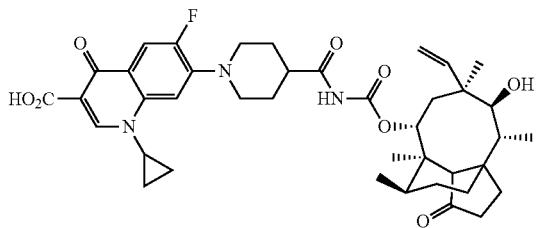

[Chem. 16]

A solution (4 mL) of the compound of Third Step in Reference Example 2 (200 mg, 0.42 mmol), 1-cyclopropyl-6,7-difluoro-1,4-dihydro-4-oxo-3-quinolinecarboxylic acid (101 mg, 0.38 mmol), and 1,8-diazabicyclo[5.4.0]unde-7-ene (62.6 μL, 0.42 mmol) in acetonitrile was heated under stirring at 80° C. for about 6 hours. After cooling, to the reaction mixture was added water (10 mL), followed by extraction with methylene chloride (10 mL×3), and the combined organic layer was washed with saturated brine (10 mL). The resultant was dried over anhydrous sodium sulfate and then filtered, and the solvent was evaporated. The residue was purified by silica gel column chromatography (ethyl acetate, ethyl acetate:methanol=10:1 and then methylene chloride:methanol:aqueous ammonia=50:10:1) to obtain 100 mg of the heading compound as a pale yellow powdery crystal (yield 37%).

$^1$H NMR (400 MHz, CDCl$_3$) δ 0.77 (d, J=7.3 Hz, 3H), 0.91 (d, J=7.3 Hz, 3H), 1.13-1.86 (m, 12H), 1.21 (s, 3H), 1.44 (s, 3H), 1.91-2.40 (m, 9H), 2.97-3.15 (m, 2H), 3.32-3.62 (m, 4H), 3.70-3.86 (m, 2H), 5.25 (d, J=17.1 Hz, 1H), 5.37 (d, J=11.6 Hz, 1H), 5.72 (d, J=8.0 Hz, 1H), 6.50 (dd, J=17.1, 11.3 Hz, 1H), 7.37 (d, J=6.7 Hz, 1H), 7.47 (br, 1H), 8.02 (d, J=12.8 Hz, 1H), 8.77 (s, 1H), 15.0 (s, 1H).

MS (ESI) (m/z): 720.4 (MH$^+$).

Example 2

First Step (3R)-3-Deoxo-11-deoxy-12-desethenyl-3-methoxy-14-methoxymethoxy-12-methylthio-11-oxo-4-epimutilin

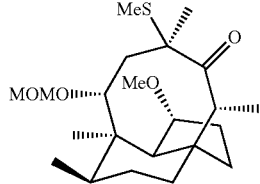

[Chem. 17]

To a solution (1000 mL) of (3R)-3-deoxo-11-deoxy-12-desethenyl-3-methoxy-14-methoxymethoxy-11-oxo-4-epimutilin (61.0 g, 0.17 mol) in anhydrous tetrahydrofuran was added dropwise potassium bis(trimethylsilyl)amide (0.5 M toluene solution) (416 mL, 0.21 mol) at −69° C. under an argon atmosphere, followed by stirring for 30 minutes. At the same temperature, a solution of S-methyl p-toluenethiosulfonate (Synthesis 2002, 343-348) (61.0 g, 0.17 mol) in anhydrous tetrahydrofuran (150 mL) was added dropwise thereto, followed by stirring for about 1.5 hours while naturally warming. To the reaction mixture was added a 10% aqueous citric acid solution (500 mL), followed by evaporation under reduced pressure. The residue was extracted with ethyl acetate (500 mL×3), and the combined organic layer was washed with saturated brine (500 mL). The resultant was dried over anhydrous sodium sulfate and then filtered, and the solvent was evaporated. The residue was purified by silica gel column chromatography (hexane:ethyl acetate=8:1) to obtain 67.7 g of the pale yellow oily heading compound (yield 98%).

MS (FAB) (m/z): 399 (MH$^+$).

HRMS (FAB) (m/z): Calcd. for $C_{22}H_{39}O_4S$ (MH$^+$): 399.2569. Found, 399.2608.

Second Step (3R)-3-Deoxo-11-deoxy-12-desethenyl-3-methoxy-12-methylthio-11-oxo-4-epimutilin

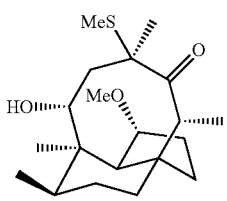

[Chem. 18]

To a solution (1000 mL) of the compound of First Step (67.6 g, 0.17 mol) in methanol was added p-toluene sulfonic acid (48.5 g, 0.26 mol) while stirring under ice-cooling, followed by stirring for about 60 hours while naturally warming. To the reaction mixture was added a saturated aqueous sodium hydrogen carbonate solution, followed by concentration, the residue was extracted with ethyl acetate (600 mL×3), and the combined organic layer was washed with saturated brine (500 mL). The resultant was dried over anhydrous sodium sulfate and then filtered, and the solvent was evaporated. The residue was purified by silica gel column chromatography (hexane:ethyl acetate=4:1) to obtain 57.4 g of the heading compound as a colorless crystal (yield 95%).

MS (FAB) (m/z): 355 (MH$^+$).

HRMS (FAB) (m/z): Calcd. for $C_{20}H_{35}O_3S$ (MH$^+$): 355.2307. Found, 355.2305.

Third Step (3R)-3-Deoxo-11-deoxy-12-desethenyl-3-methoxy-12-methylthio-11-oxo-14-[1-(2,2,2-trichloroethoxycarbonyl)piperidine-4-carbonyl]carbamoyl-4-epimutilin

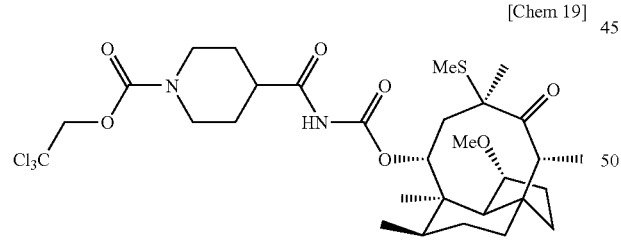

[Chem 19]

The reaction was carried out using 300 mg (0.85 mmol) of the compound of Second Step, 317 mg (2.12 mmol) of silver cyanate, the acid chloride prepared from 387 mg (1.27 mmol) of the carboxylic acid of Reference Example 1 and oxalyl chloride, and triethylamine 0.18 mL (1.27 mmol) in accordance with the method of First Step of Reference Example 2, and the residue was purified by silica gel column chromatography (hexane:ethyl acetate=2:1 and then hexane:ethyl acetate=1:1) to obtain 465 mg of the heading compound as a colorless powdery substance (yield 80%).

MS (FAB) (m/z): 683.5 (MH$^+$).

HRMS (FAB) (m/z): Calcd. for $C_{30}H_{46}Cl_3N_2O_7S$(MH$^+$): 683.2091. Found, 683.2077.

Fourth Step (3R)-3-oxo-11-deoxy-12-desethenyl-3-methoxy-12-methylthio-11-oxo-14-[(1-piperidine-4-carbonyl)carbamoyl-4-epimutilin

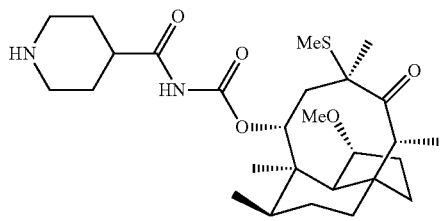

[Chem. 20]

To a solution (6 mL) of the compound of Third Step (1.74 g, 2.54 mmol) in acetic acid was added zinc powder (830 mg, 12.7 mmol) under ice-cooling, followed by stirring at room temperature. After 24 hours, zinc powder (830 mg, 12.7 mmol) was added thereto, followed by further stirring at room temperature for 3 hours. The reaction liquid was filtered over Celite, and the residue was washed with water and ethyl acetate. The combined filtrate was extracted with ethyl acetate (20 mL×3), and the combined organic layer was extracted with a 10% aqueous citric acid solution (5 mL×5). The aqueous layer was combined, alkalified with a saturated aqueous sodium hydrogen carbonate solution, and extracted with ethyl acetate (100 mL×5). The organic layer was washed with saturated brine (100 mL), dried over anhydrous magnesium sulfate, and filtered, and the solvent was evaporated. The obtained residue was purified by silica gel column chromatography (NH, ethyl acetate:methanol=10:1 and then ethyl acetate:methanol=5:1) to obtain 808 mg of the heading compound as a colorless powdery crystal (yield 62%).

MS (FAB) (m/z): 509 (MH$^+$).

HRMS (FAB) (m/z): Calcd. for $C_{27}H_{45}N_2O_5S$(MH$^+$): 509.3049. Found, 509.3044.

Fifth Step

12-Desethenyl-12-methylthio-14-(1-piperidine-4-carbonyl)carbamoylmutilin

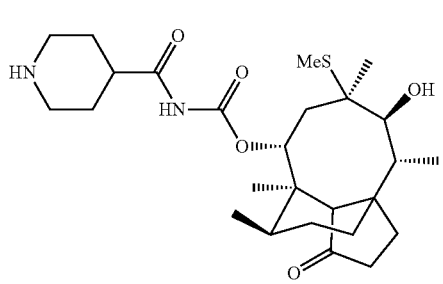

[Chem. 21]

The reaction was carried out using the compound of Fourth Step (370 mg, 0.73 mmol) in accordance with the method of Third Step of Reference Example 2, and the residue was purified by silica gel column chromatography (NH, hexane:

ethyl acetate=1:1, ethyl acetate:methanol=10:1, 5:1 and then 2:1) to obtain 156 mg of the heading compound as a colorless powdery crystal (yield 43%).

MS (FAB) (m/z): 495 (MH$^+$).

HRMS (FAB) (m/z): Calcd. for C$_{26}$H$_{43}$N$_2$O$_5$S(MH$^+$): 495.2893. Found, 495.2897.

Sixth Step

14-[1-(3-Carboxy-1-cyclopropyl-1,4-dihydro-6-fluoro-4-oxoquinolin-7-yl)piperidine-4-carbonyl]carbamoyl-12-desethenyl-12-methylthiomutilin

[Chem. 22]

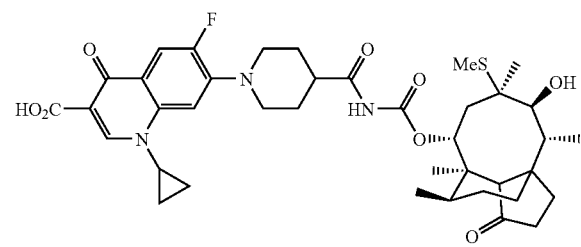

The reaction was carried out using a solution of the compound of Fifth Step (3.00 g, 6.06 mmol), 1-cyclopropyl-6,7-difluoro-1,4-dihydro-4-oxo-3-quinoline carboxylic acid (1.46 g, 5.51 mmol), 1,8-diazabicyclo[5.4.0]unde-7-cene (0.90 mL, 6.06 mmol) in acetonitrile (60 mL) in accordance with the method of Example 1, and the residue was purified by silica gel column chromatography (ethyl acetate, ethyl acetate:methanol=20:1), further dissolved in methanol (30 mL), and crystallized using water (100 mL) to obtain 2.04 g of the heading compound as a pale yellow powdery crystal (yield 50%).

$^1$H NMR (400 MHz, CDCl$_3$) δ 0.78 (d, J=6.7 Hz, 3H), 0.95 (d, J=6.7 Hz, 3H), 1.04-1.85 (m, 11H), 1.45 (s, 3H), 1.46 (s, 3H), 1.92-2.33 (m, 9H), 2.02 (s, 3H), 2.51-2.61 (m, 1H), 2.97-3.11 (m, 2H), 3.42-3.55 (m, 4H), 3.62-3.84 (m, 2H), 5.77 (d, J=8.0 Hz, 1H), 7.37 (d, J=7.3 Hz, 1H), 7.38 (br, 1H), 8.03 (d, J=12.8 Hz, 1H), 8.78 (s, 1H), 15.0 (s, 1H).

MS (ESI) (m/z): 770.3 (MH$^+$).

Example 3

First Step

1-Cyclopropyl-6,7-difluoro-1,4-dihydro-4-oxo-3-quinolinecarboxylic acid 2-(4-morpholyl)ethyl

[Chem. 23]

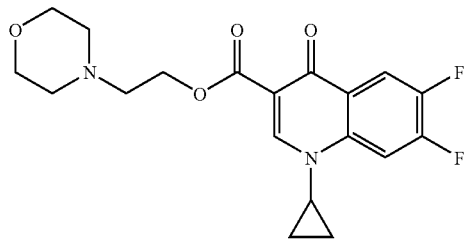

To a solution (10 mL) of 1-cyclopropyl-6,7-difluoro-1,4-dihydro-4-oxo-3-quinolinecarboxylic acid (300 mg, 1.13 mmol) in N,N-dimethylformamide were added 4-(2-chloroethyl)morpholine (253 mg, 1.36 mmol) and cesium carbonate (1.11 g, 3.39 mmol) under stirring at room temperature, followed by heating under stirring at an internal temperature of 60° C. for 4 hours. After cooling, to the mixed reaction liquid was added water (5 mL), followed by extraction with methylene chloride (10 mL). The organic layer was washed with saturated brine (10 mL), dried over anhydrous sodium sulfate, and filtered, and the solvent was evaporated. The obtained residue was washed with diisopropyl ether to obtain 326 mg of the heading compound as a colorless powdery crystal (yield 76%).

MS (ESI) (m/z): 379.2 (MH$^+$).

HRMS (ESI) (m/z): Calcd. for C$_{19}$H$_{21}$F$_2$N$_2$O$_4$ (MH$^+$): 379.14694. Found, 379.14771.

Second Step 14-(1-{3-[2-(4-Morpholyl)ethoxycarbonyl]-1-cyclopropyl-1,4-dihydro-6-fluoro-4-oxo-3-quinolin-7-yl}piperidine-4-carbonyl)carbamoyl-12-desethenyl-12-methylthiomutilin

[Chem. 24]

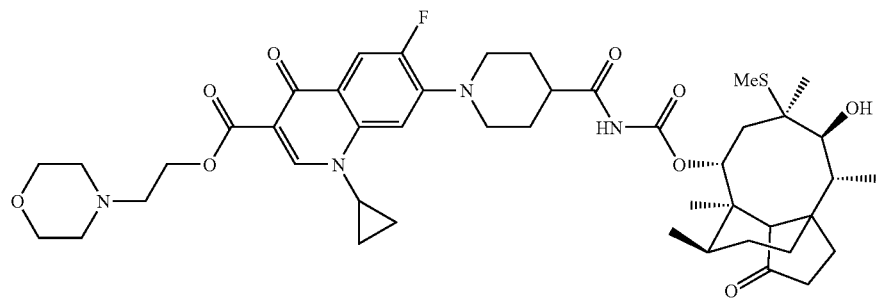

A solution (8 mL) of the compound of First Step (300 mg, 0.79 mmol), the compound of Fifth Step of Example 2 (588 mg, 1.19 mmol) and triethylamine (0.17 mL, 1.19 mmol) in acetonitrile was stirred under heating at 80° C. for about 17 hours in accordance with the method of Example 1. After cooling, the reaction mixture was concentrated under reduced pressure, and water (10 mL) was added thereto, followed by extraction with methylene chloride (10 mL×3). The combined organic layer was washed with saturated brine (10 mL). The resultant was dried over anhydrous sodium sulfate and then filtered, and the solvent was evaporated. The residue was purified by silica gel column chromatography (methylene chloride:methanol=20:1 and then methylene chloride:methanol:aqueous ammonia=10:1:0.1) to obtain 82.4 mg of the heading compound as a pale yellow powdery crystal (yield 12%).

MS (ESI) (m/z): 853.5 (MH$^+$).

HRMS (ESI) (m/z): Calcd. for $C_{45}H_{62}FN_4O_9S$ (MH$^+$): 853.42215. Found, 853.42141.

Third Step 14-(1-{3-[2-(4-Morpholyl)ethoxycarbonyl]-1-cyclopropyl-1,4-dihydro-6-fluoro-4-oxoquinolin-7-yl}piperidine-4-carbonyl)carbamoyl-12-desethenyl-12-methylthiomutilin hydrochloride HRMS (ESI) (m/z): Calcd. for $C_{45}H_{62}FN_4O_9S$ (MH$^+$): 853.42215. Found, 853.42219.

Example 4

First Step 2-(Dimethylamino)ethyl 1-cyclopropyl-6,7-difluoro-1,4-dihydro-4-oxo-3-quinolinecarboxylate

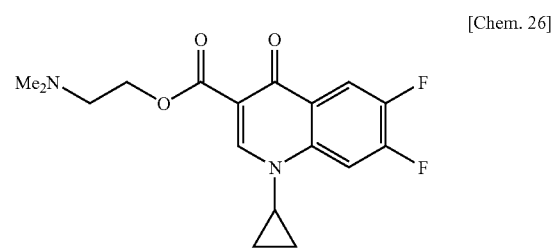

[Chem. 26]

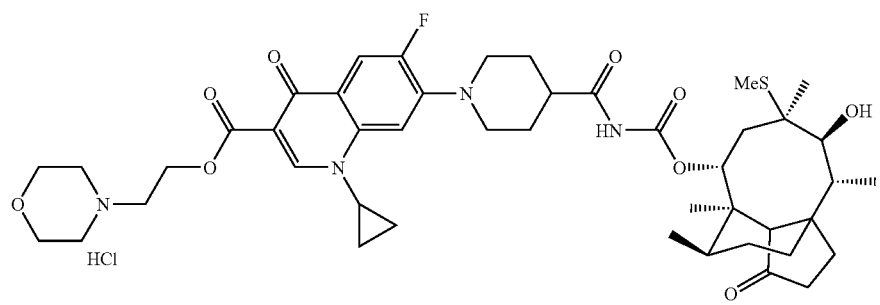

[Chem. 25]

To a solution (4 mL) of the compound of Second Step (80.0 mg, 93.8 μmol) in methylene chloride was added 3.91 M hydrogen chloride-dioxane (24.0 mL) at 4° C. After stirring at room temperature for 30 minutes, the solvent was evaporated under reduced pressure. The residue was washed with diisopropyl ether to obtain 75.9 mg of the heading compound as a yellow powdery crystal (yield 91%).

MS (ESI) (m/z): 853.5 (of a free form MH$^+$).

1-Cyclopropyl-6,7-difluoro-1,4-dihydro-4-oxo-3-quinolinecarboxylic acid (300 mg, 1.13 mmol), 2-chloro-N,N-dimethylethylamine hydrochloride (196 mg, 1.36 mmol), and cesium carbonate (1.11 g, 3.39 mmol) were reacted in accordance with the method of First Step of Example 3 to obtain 282 mg of the heading compound as a colorless powdery crystal (yield 74%).

MS (ESI) (m/z): 337.2 (MH$^+$).

HRMS (ESI) (m/z): Calcd. for $C_{17}H_{19}F_2N_2O_3$ (MH$^+$): 337.13637. Found, 337.14031.

Second Step 14-(1-{3-[2-(Dimethylamino)ethoxycarbonyl]-1-cyclopropyl-1,4-dihydro-6-fluoro-4-oxoquinolin-7-yl}piperidine-4-carbonyl)carbamoyl-12-desethenyl-12-methylthiomutilin

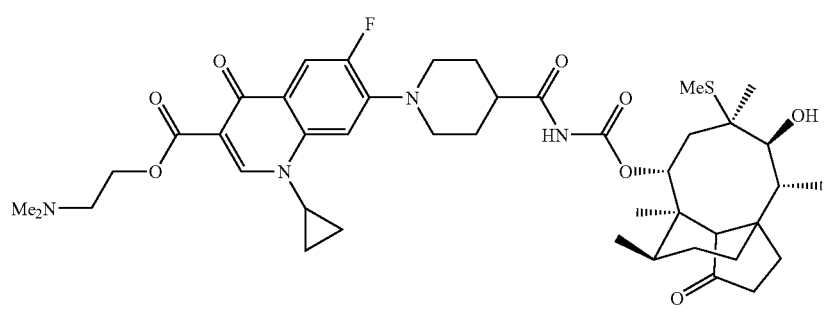

[Chem. 27]

The compound of First Step (280 mg, 0.83 mmol), the compound of Fifth Step of Example 2 (618 mg, 1.25 mmol), and triethylamine (0.41 mL, 2.91 mmol) were reacted in accordance with the method of Example 1, and the residue was purified by silica gel column chromatography (ethyl acetate:methanol=20:1 and then ethyl acetate:methanol=10:1 and then chloroform:methanol=10:1) to obtain 177 mg of the heading compound as a colorless powdery crystal (yield 26%).

MS (ESI) (m/z): 811.4 (MH$^+$).

HRMS (ESI) (m/z): Calcd. for $C_{43}H_{60}FN_4O_8S$ (MH$^+$): 811.41159. Found, 811.40816.

Third Step 14-(1-{3-[2-(Dimethylamino)ethoxycarbonyl]-1-cyclopropyl-1,4-dihydro-6-fluoro-4-oxoquinolin-7-yl}piperidine-4-carbonyl)carbamoyl-12-desethenyl-12-methylthiomutilin hydrochloride

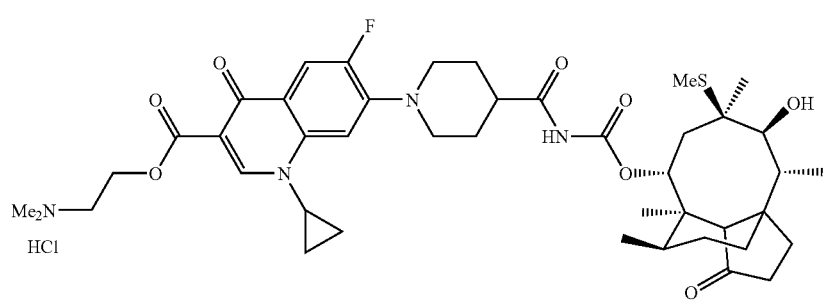

[Chem. 28]

In accordance with the method of Third Step of Example 3, the compound of Second Step (150 mg, 0.19 mmol) was made into its hydrochloride salt, and the residue was washed with diisopropyl ether to obtain 140 mg of the heading compound as a yellow powdery crystal (yield 89%).

MS (ESI) (m/z): 811.4 (MH$^+$ of a free form).

HRMS (ESI) (m/z): Calcd. for $C_{43}H_{60}FN_4O_8S$ (MH$^+$ of a free form): 811.41159. Found, 811.40887.

Example 5

The inventive compounds 5 to 27 were prepared using the same procedure as in Example 1.

TABLE 1

| No. | R | MS (m/z) | HRMS (m/z) |
|---|---|---|---|
| 5 | HO₂C-[1-ethyl-6-fluoro-7-methyl-4-oxo-quinoline-3-carboxylic acid] | (ESI) 706.4 (MH−) | (ESI): C39H49FN3O8 (MH−): Calcd, 706.35037. Found, 706.35030. |
| 6 | HO₂C-[1-ethyl-6,8-difluoro-7-methyl-4-oxo-quinoline-3-carboxylic acid] | (FAB) 726.5 (MH+) | (FAB): C39H50F2N3O8 (MH+): Calcd, 726.3566. Found, 726.3588. |
| 7 | HO₂C-[1-(2-fluoroethyl)-6,8-difluoro-7-methyl-4-oxo-quinoline-3-carboxylic acid] | (FAB) 744.6 (MH+) | (FAB): C39H49F3N3O8 (MH+): Calcd, 744.3472. Found, 744.3498. |
| 8 | HO₂C-[1-(2-fluoroethyl)-6-fluoro-7-methyl-4-oxo-quinoline-3-carboxylic acid] | (ESI) 724.4 (MH−) | (ESI): C39H48F2N3O8 (MH−): Calcd, 724.34095. Found, 724.34000. |
| 9 | HO₂C-[1-(2-fluoroethyl)-6-fluoro-7-methyl-8-methoxy-4-oxo-quinoline-3-carboxylic acid] | (ESI) 754.3 (MH−) | (ESI): C40N50F2N3O9 (MH−): Calcd, 754.35151. Found 754.35202. |

TABLE 1-continued

| No. | R | MS (m/z) | HRMS (m/z) |
|---|---|---|---|
| 10 | | (ESI) 720.3 (MH−) | (ESI): C39H47FN3O9 (MH−): Calcd, 720.32963. Found, 720.32928. |
| 11 | | (FAB) 792 (MH+) | (FAB): C43N49F3N3O8 (MH+): Calcd, 792.3472. Found, 792.3442. |
| 12 | | (ESI) 736.4 (MH−) | (ESI): C40H48F2N3O8 (MH−): Calcd, 736.34095. Found, 736.34029. |
| 13 | | (ESI) 752.4 (MH−) | (ESI): C40H48ClFN3O8 (MH−): Calcd, 752.31139. Found, 752.31099. |
| 14 | | (FAB) 721.5 (MH+) | (FAB): C39H50FN4O8 (MH+): Calcd, 721.3613. Found, 721.3655. |

TABLE 1-continued

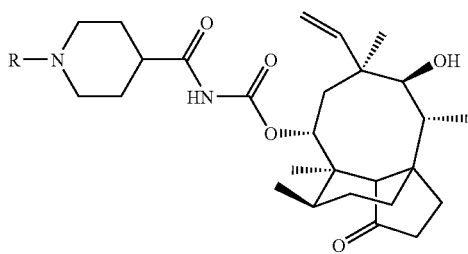

| No. | R | MS (m/z) | HRMS (m/z) |
|---|---|---|---|
| 15 | (quinolone with HO2C, F, Me, N-cyclopropyl-F substituents) | (ESI) 736.3 (MH−) | (ESI): C40H48F2N3O8 (MH−): Calcd, 736.34095. Found, 736.34464. |

TABLE 2

| No. | R | MS (m/z) | HRMS (m/z) |
|---|---|---|---|
| 16 | (naphthyridinone with HO2C, F, Me, N-cyclopropyl-F) | (ESI) 739.3 (MH+) | (ESI): C39H49F2N4O8 (MH+): Calcd, 739.35184. Found 139.35536. |
| 17 | (quinolone with HO2C, F, Me, F, N-cyclopropyl-F) | (ESI) 754.3 (MH−) | (ESI): C40H47F3N3O8 (MH−): Calcd, 754.33152. Found, 754.33050. |
| 18 | (quinolone with HO2C, F, Me, OMe, N-cyclopropyl-F) | (ESI) 766.4 (MH−) | (ESI): C41H50F2N3O9 (MH−): Calcd, 766.35151. Found, 766.35171. |
| 19 | (quinolone with HO2C, F, Me, OCHF2, N-cyclopropyl-F) | (ESI) 802.4 (MH−) | (ESI): C41H48F4N3O9 (MH−): Calcd, 802.33267. Found, 802.33302. |

TABLE 2-continued

| | Structure | MS | HRMS |
|---|---|---|---|
| 20 | (quinolone with 8-OMe, 7-Me, N-fluorocyclopropyl) | (ESI) 748.4 (MH−) | (ESI) C41H51FN3O9 (MH−): Calcd, 748.36093. Found, 748.36055. |
| 21 | (naphthyridone with 7-F, 6-Me, N-tert-butyl) | (ESI) 735.4 (MH−) | (ESI) C40H52FN4O8 (MH−): Calcd, 735.37692. Found, 735.38025. |
| 22 | (quinolone with 8-F, 7-Me, N-cyclopropyl) | (ESI) 718.4 (MH−) | (ESI) C40H49FN3O8 (MH−): Calcd, 718.35037. Found, 718.35083. |
| 23 | (tricyclic oxazine quinolone with F, Me, methyl) | (ESI) 734.4 (MH−) | (ESI) C40H49FN3O9 (MH−): Calcd, 734.34528. Found, 734.34313. |
| 24 | (tricyclic oxazine quinolone with F, Me, fluoromethyl) | (ESI) 752.3 (MH−) | (ESI) C40H48F2N3O9 (MH−): Calcd, 752.33586. Found, 752.33520. |
| 25 | (tricyclic oxazine quinolone with Me, methyl) | (ESI) 716.4 (MH−) | (ESI) C40H50N3O9 (MH−): Calcd, 716.35470. Found, 716.35447. |
| 26 | (tricyclic oxazine quinolone with Me, fluoromethyl) | (ESI) 734.4 (MH−) | (ESI) C40H49FN3O9 (MH−): Calcd, 734.34528. Found, 734.34640. |

TABLE 2-continued

| 27 | [structure: quinolone with HO2C, F, Me, OMe, N-cyclopropyl] | (ESI) 748.4 (MH−) | (ESI): C41H51FN3O9 (MH−):<br>Calcd, 748.36093.<br>Found, 748.36024. |

Example 6

The inventive compound 28 was prepared using the same procedure as in Example 2.

TABLE 3

[structure shown above table: R—N bicyclic amine linked via S-CH2-C(O)-O to pleuromutilin-like core with vinyl, OH, and ketone]

| No. | R | MS (m/z) | HRMS (m/z) |
|---|---|---|---|
| 28 | [structure: quinolone with HO2C, F, Me, N-cyclopropyl] | (ESI) 747.3 (MH−) | (ESI): C42H52FN2O7S (MH−):<br>Calcd, 747.34792.<br>Found, 747.34868. |

Example 7

The inventive compounds 29 to 52 were prepared using the same procedure as in Example 2.

TABLE 4

[structure shown above table: R—N-piperidine-C(O)-NH-C(O)-O-pleuromutilin core with MeS, OH, and ketone]

| No. | R | MS (m/z) | HRMS (m/z) |
|---|---|---|---|
| 29 | [structure: quinolone with HO2C, F, Me, N-ethyl] | (ESI) 726.3 (MH−) | (ESI): C36H49FN3O8S (MH−):<br>Calcd, 726.32244.<br>Found, 726.32206. |

TABLE 4-continued

| No. | R | MS (m/z) | HRMS (m/z) |
|---|---|---|---|
| 30 | (1-ethyl-6-fluoro-7-methyl-8-fluoro-4-oxoquinoline-3-carboxylic acid) | (FAB) 746.2 (MH+) | (FAB): C38H50F2N3O8S (MH+): Calcd, 746.3287. Found, 746.3270. |
| 31 | (1-(2-fluoroethyl)-6-fluoro-7-methyl-8-fluoro-4-oxoquinoline-3-carboxylic acid) | (ESI) 762.3 (MH−) | (ESI): C38H47F3N3O8S (MH−): Calcd, 762.30359. Found, 762.30355. |
| 32 | (1-(2-fluoroethyl)-6-fluoro-7-methyl-4-oxoquinoline-3-carboxylic acid) | (FAB) 746.5 (MH+) | (FAB): C38H50F2N3O8S (MH+): Calcd, 746.3287. Found, 746.3314. |
| 33 | (1-(2-fluoroethyl)-6-fluoro-7-methyl-8-methoxy-4-oxoquinoline-3-carboxylic acid) | (ESI) 774.3 (MH−) | (ESI): C39H50F2N3O9S (MH−): Calcd, 774.32358. Found, 774.32658. |
| 34 | (fluoro-methyl oxazino-quinoline carboxylic acid) | (ESI) 740.3 (MH−) | (ESI): C38H47FN3O9S (MH−): Calcd, 740.30170. Found, 740.30047. |

TABLE 4-continued

| No. | R | MS (m/z) | HRMS (m/z) |
|---|---|---|---|
| 35 | [2,4-difluorophenyl-substituted 6-fluoro-7-methyl-4-oxoquinoline-3-carboxylic acid] | (ESI) 810.3 (MH−) | (ESI): C42H47F3N3O8S (MH−): Calcd, 810.30359. Found, 810.30392. |
| 36 | [1-cyclopropyl-6,8-difluoro-7-methyl-4-oxoquinoline-3-carboxylic acid] | (FAB) 758 (MH+) | (FAB): C39H50F2N3O8S (MH+): Calcd, 758.3287. Found, 758.3304. |
| 37 | [1-cyclopropyl-8-chloro-6-fluoro-7-methyl-4-oxoquinoline-3-carboxylic acid] | (ESI) 774.3 (MH−) | (ESI): C39H50ClFN3O8S (MH+): Calcd, 774.29912. Found, 774.29944. |
| 38 | [1-cyclopropyl-6-fluoro-7-methyl-4-oxo-1,8-naphthyridine-3-carboxylic acid] | (FAB) 741.5 (MH+) | (FAB): C38H50FN4O8S (MH+): Calcd, 741.3333. Found, 741.3361. |
| 39 | [1-(2-fluorocyclopropyl)-6-fluoro-7-methyl-4-oxoquinoline-3-carboxylic acid] | (ESI) 756.3 (MH−) | (ESI): C39H48F2N3O8S (MH−): Calcd, 756.31302. Found, 756.31319. |

TABLE 5

| # | Structure | MS | HRMS |
|---|---|---|---|
| 40 | quinolone structure | (ESI) 757.3 (MH−) | (ESI): C38H47F2N4O8S (MH−): Calcd, 751.30826. Found, 757.30725. |
| 41 | quinolone structure | (ESI) 776.4 (MH+) | (ESI): C39H49F3N3O8S (MH+): Calcd, 776.31924. Found, 776.31841. |
| 42 | quinolone structure | (ESI) 790.3 (MH−) | (ESI): C39H47ClF2N3O8S (MH−): Calcd, 790.27404. Found, 790.27404. |
| 43 | quinolone structure | (ESI) 786.3 (MH−) | (ESI): C40H50F2N3O9S (MH−): Calcd, 786.32358. Found, 786.32393. |
| 44 | quinolone structure | (ESI) 822.3 (MH−) | (ESI): C40H48F4N3O9S (MH−): Calcd, 822.30474. Found, 822.30510. |
| 45 | quinolone structure | (ESI) 768.3 (MH−) | (ESI): C40H51FN3O9S (MH−): Calcd, 768.33300. Found, 768.33386. |

TABLE 5-continued

| 46 | [structure: 7-fluoro-8-methyl-1-tert-butyl-1,8-naphthyridin-4-one-3-carboxylic acid derivative] | (ESI) 755.4 (MH−) | (ESI): C39H52N4O8S (MH−):<br>Calcd, 755.34899.<br>Found, 755.34970. |
| --- | --- | --- | --- |
| 47 | [structure: 1-cyclopropyl-8-fluoro-7-methylquinolone carboxylic acid derivative] | (FAB) 741 (MH+) | (FAB): C39H51FN3O8S (MH+):<br>Calcd, 740.3381.<br>Found, 740.3428. |
| 48 | [structure: fluoromethyl-pyrido-benzoxazine carboxylic acid derivative] | (FAB) 756.5 (MH+) | (FAB): C39H51FN3O9S (MH+):<br>Calcd, 756.3330.<br>Found, 756.3372. |
| 49 | [structure: fluoromethyl-substituted pyrido-benzoxazine carboxylic acid derivative] | (ESI) 772.3 (MH−) | (ESI): C39H48F2N3O9S (MH−):<br>Calcd, 772.30793.<br>Found, 772.30613. |
| 50 | [structure: methyl-pyrido-benzoxazine carboxylic acid derivative] | (ESI) 736.3 (MH−) | (ESI): C39H50N3O9S (MH−):<br>Calcd, 736.32677.<br>Found, 736.32651. |
| 51 | [structure: fluoromethyl-methyl-pyrido-benzoxazine carboxylic acid derivative] | (ESI) 754.4 (MH−) | (ESI): C39H49FN3O9S (MH−):<br>Calcd, 754.31735.<br>Found, 754.31426. |

TABLE 6

| 52 | 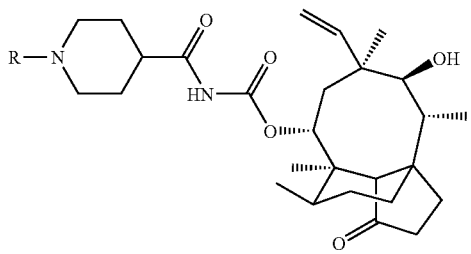 | (ESI) 770.3 (MH+) | (ESI): C40H53FN3O9S (MH+):<br>Calcd, 770.34865.<br>Found, 770.34778. |
|---|---|---|---|

Example 8

The inventive compounds 53 to 70 were prepared using the same procedure as in Example 1.

TABLE 7

| No. | R | MS (m/z) | HRMS (m/z) | ¹H NMR |
|---|---|---|---|---|
| 53 | ![structure with HOOC, F, cyclopropyl, Me, OCHF2] | (ESI) 786.4 (MH⁺) | (ESI) C41H51F3N3O9 Calcd., 786.35774 Found, 786.35712 | (in CDCl₃) δ 0.76 (d, J = 7.3 Hz, 3H), 0.91 (d, J = 6.7 Hz, 3H), 0.95-1.01 (m, 2H), 1.11-1.33 (m, 6H), 1.40-2.36 (m, 20H), 3.29-3.60 (m, 6H), 4.11-4.18 (m, 1H), 5.25 (dd, J = 17.1, 1.2 Hz, 1H), 5.38 (dd, J = 11.0, 1.2 Hz, 1H), 5.72 (d, J = 8.6 Hz, 1H), 6.49 (t, J = 74.5 Hz, 1H), 6.50 (dd, J = 17.1, 11.0 Hz, 1H), 7.34 (s, 1H), 8.04 (d, J = 11.6 Hz, 1H), 8.86 (s, 1H), 14.5 (s, 1H). |
| 54 | ![structure with HOOC, cyclopropyl, Me, OCHF2] | (ESI) 768.4 (MH⁺) | (ESI) C41H52F2N3O9 Calcd., 768.36716 Found, 768.36735 | (in CDCl₃) δ 0.77 (d, J = 6.7 Hz, 3H), 0.91 (d, J = 7.3 Hz, 3H), 0.96-1.02 (m, 2H), 1.11-2.38 (m, 25H), 2.98-3.08 (m, 2H), 3.34-3.45 (m, 2H), 3.66-3.76 (m, 4H), 4.18-4.25 (m, 1H), 5.25 (dd, J = 17.1, 1.2 Hz, 1H), 5.38 (dd, J = 11.0, 1.2 Hz, 1H), 5.72 (d, J = 8.6 Hz, 1H), 6.50 (dd, J = 17.7, 11.0 Hz, 1H), 6.52 (t, J = 75.8 Hz, 1H), 7.23 (d, J = 9.2 Hz, 1H), 7.37 (s, 1H), 8.33 (d, J = 9.2 Hz, 1H), 8.87 (s, 1H), 14.7 (s, 1H). |

TABLE 8

| 55 | ![structure with HOOC, cyclopropyl, Me, OMe] | (ESI) 732.4 (MH⁺) | (ESI) C41H54N3O9 Cacld., 732.38600 Found, 732.38545 | (in CDCl₃): δ 0.77 (d, J = 7.3 Hz, 3H), 0.91 (d, J = 6.7 Hz, 3H), 0.98-2.36 (m, 26H), 2.92-3.03 (m, 2H), 3.31-3.42 (m, 2H), 3.78-3.87 (m, 5H), 4.04-4.12 (m, 1H), 5.25 (dd, J = 17.7, 1.2 Hz, 1H), (dd, J = 11.0, 1.2 Hz, 1H), 5.73 (d, J = 8.6 Hz, 1H), 6.51 (dd, J = 17.1, 11.0 Hz, 1H), 7.17 (d, J = 9.2 Hz, 1H), 7.38 (s, 1H), 8.17 (d, J = 9.2 Hz, 1H), 8.83 (s, 1H), 15.0 (s, 1H). |

TABLE 8-continued

| # | Structure | MS | Formula | NMR |
|---|---|---|---|---|
| 56 | [quinolone with 6-F, 7-Me, 8-OMe, N-Me, HOOC at 3] | (ESI) 724.4 (MH+) | (ESI) C39H51FN3O9 Calcd., 724.36093 Found, 724.36125 | (in CDCl3): δ 0.76 (d, J = 6.7 Hz, 3H), 0.91 (d, J = 6.7 Hz, 3H), 1.11-2.40 (m, 24H), 3.25-3.62 (m, 6H), 3.86 (s, 3H), 4.20 (s, 3H), 5.25 (dd, J = 17.1, 1.2 Hz, 1H), 5.38 (dd, J = 11.0, 1.2 Hz, 1H), 5.73 (d, J = 8.6 Hz, 1H), 6.50 (dd, J = 17.1, 11.0 Hz, 1H), 7.32 (s, 1H), 7.94 (d, J = 12.2 Hz, 1H), 8.85 (s, 1H), 14.8 (s, 1H). |
| 57 | [quinolone with 6-F, 7-Me, 8-OMe, N-Et, HOOC at 3] | (ESI) 738.4 (MH+) | (ESI) C40H53FN3O9 Calcd., 738.37658 Found, 738.37641 | (in CDCl3): δ 0.77 (d, J = 6.7 Hz, 3H), 0.91 (d, J = 6.7 Hz, 3H), 0.95-1.05 (m, 5H), 1.12-2.40 (m, 29H), 3.29-3.58 (m, 6H), 3.86 (s, 3H), 4.57 (q, J = 6.7 Hz, 2H), 5.25 (dd, J = 17.7, 1.2 Hz,1H), 5.38 (dd, J = 11.0, 1.2 Hz, 1H), 5.73 (d, J = 7.9 Hz, 1H), 6.51 (dd, J = 17.7, 11.0 Hz, 1H), 7.33 (s, 1H), 7.96 (d, J = 12.2 Hz, 1H), 8.61 (s, 1H), 14.9 (s, 1H). |

TABLE 9

| # | Structure | MS | Formula | NMR |
|---|---|---|---|---|
| 58 | [quinolone with 6-F, 7-Me, 8-OMe, N-propyl, HOOC at 3] | (ESI) 752.4 (MH+) | (ESI) C41H55FN3O9 Calcd., 752.39223 Found, 752.39280 | (in CDCl3): δ 0.77 (d, J = 7.3 Hz, 3H), 0.87-0.93 (m, 6H), 1.11-1.30 (m, 1H), 1.37-2.40 (m, 25H), 3.26-3.60 (m, 6H), 3.84 (s, 3H), 4.46 (t, J = 7.3 Hz, 2H), 5.25 (dd, J = 17.7, 1.2 Hz, 1H), 5.38 (dd, J = 11.0, 1.2 Hz, 1H), 5.73 (d, J = 8.6 Hz, 1H), 6.51 (dd, J = 17.7, 11.0 Hz, 1H), 7.29 (s, 1H), 7.96 (d, J = 12.2 Hz, 1H), 8.59 (s, 1H). |
| 59 | [quinolone with 6-F, 7-Me, 8-OMe, N-butyl, HOOC at 3] | (ESI) 766.4 (MH+) | (ESI) C42H57FN3O9 Calcd., 766.40788 Found, 766.40735 | (in CDCl3): δ 0.77 (d, J = 7.3 Hz, 3H), 0.87-0.97 (m, 6H), 1.11-2.41 (m, 28H), 3.24-3.46 (m, 4H), 3.55 (d, J = 11.6 Hz, 2H), 3.84 (s, 3H), 4.50 (t, J = 7.3 Hz, 2H), 5.25 (dd, J = 17.7, 1.2 Hz, 1H), 5.38 (dd, J = 11.0, 1.2 Hz, 1H), 5.73 (d, J = 8.6 Hz, 1H), 6.51 (dd, J = 17.1, 11.0 Hz, 1H), 7.29 (s, 1H), 7.96 (d, J = 11.6 Hz, 1H), 8.58 (s, 1H), 14.9 (s, 1H). |
| 60 | [quinolone with 6-F, 7-Me, 8-OMe, N-pentyl, HOOC at 3] | (ESI) 780.4 (MH+) | (ESI) C43H59FN3O9 Calcd., 780.42353 Found, 780.42307 | (in CDCl3): δ 0.77 (d, J = 7.3 Hz, 3H), 0.86-0.94 (m, 6H), 1.12-2.37 (m, 30H), 3.25-3.45 (m, 4H), 3.55 (d, J = 11.0 Hz, 2H), 3.84 (s, 3H), 4.48 (t, J = 7.3 Hz, 2H), 5.25 (dd, J = 17.1, 1.2 Hz, 1H), 5.38 (dd, J = 11.0, 1.2 Hz, 1H), 5.73 (d, J = 8.6 Hz, 1H), 6.51 (dd, J = 17.1, 11.0 Hz, 1H), 7.31 (s, 1H), 7.96 (d, J = 12.2 Hz, 1H), 8.58 (s, 1H), 14.9 (s, 1H). |

TABLE 10

| No. | Structure | MS | HRMS | ¹H NMR |
|---|---|---|---|---|
| 61 | quinolone with N-pentyl, 6-F, 7-Me, 8-OMe, 3-COOH | (ESI) 794.4 (MH⁺) | (ESI) $C_{44}H_{61}FN_3O_9$ Calcd., 794.43918 Found, 794.43979 | (in CDCl$_3$): δ 0.77 (d, J = 7.3 Hz, 3H), 0.87 (t, J = 7.3 Hz, 3H), 0.91 (d, J = 6.7 Hz, 3H), 1.11-2.40 (m, 32H), 3.25-3.44 (m, 4H), 3.55 (d, J = 11.6 Hz, 2H), 3.84 (s, 3H), 4.48 (t, J = 7.3 Hz, 2H), 5.25 (dd, J = 17.7, 1.2 Hz, 1H),), 5.38 (dd, J = 11.0, 1.2 Hz, 1H), 5.73 (d, J = 8.6 Hz, 1H), 6.51 (dd, J = 17.7, 11.0 Hz, 1H), 7.30 (s, 1H), 7.96 (d, J = 12.2, 1H), 8.58 (s, 1H), 14.9 (s, 1H). |
| 62 | quinolone with N-hexyl, 6-F, 7-Me, 8-OMe, 3-COOH | (ESI) 808.5 (MH⁺) | (ESI) $C_{45}H_{63}FN_3O_9$ Calcd., 808.45483 Found, 808.45486 | (in CDCl$_3$): δ 0.77 (d, J = 7.3 Hz, 3H), 0.86 (t, J = 7.3 Hz, 3H), 0.91 (d, J = 7.3 Hz, 3H), 1.11-2.41 (m, 34H), 3.25-3.44 (m, 4H), 3.55 (d, J = 11.6 Hz, 2H), 3.84 (s, 3H), 4.48 (t, J = 7.3 Hz, 2H), 5.25 (dd, J = 17.1, 1.2 Hz, 1H), 5.38 (dd, J = 11.0, 1.2 Hz, 1H), 5.73 (d, J = 8.6 Hz, 1H), 6.51 (dd, J = 17.7, 11.0 Hz, 1H), 7.29 (s, 1H), 7.96 (d, J = 12.2, 1H), 8.58 (s, 1H), 14.9 (s, 1H). |
| 63 | quinolone with N-heptyl, 6-F, 7-Me, 8-OMe, 3-COOH | (ESI) 822.5 (MH⁺) | (ESI) $C_{46}H_{65}FN_3O_9$ Calcd., 822.47048 Found, 822.46979 | (in CDCl$_3$): δ 0.77 (d, J = 7.3 Hz, 3H), 0.87 (t, J = 6.7 Hz, 3H), 0.91 (d, J = 6.7 Hz, 3H), 1.11-2.41 (m, 36H), 3.24-3.45 (m, 4H), 3.49-3.59 (m, 2H), 3.84 (s, 3H), 4.48 (t, J = 7.3 Hz, 2H), 5.25 (dd, J = 17.1, 1.2 Hz, 1H),), 5.38 (dd, J = 11.0, 1.2 Hz, 1H), 5.73 (d, J = 8.6 Hz, 1H), 6.51 (dd, J = 17.7 11.0 Hz, 1H), 7.30 (s, 1H), 7.96 (d, J = 12.2, 1H), 8.58 (s, 1H), 14.9 (s, 1H). |

TABLE 11

| No. | Structure | MS | HRMS | ¹H NMR |
|---|---|---|---|---|
| 64 | quinolone with N-(2-methoxyethyl), 6-F, 7-Me, 8-OMe, 3-COOH | (ESI) 768.4 (MH⁺) | (ESI) $C_{41}H_{55}FN_3O_{10}$ Calcd., 768.38715 Found, 768.38688 | (in CDCl$_3$): δ 0.76 (d, J = 6.7 Hz, 3H), 0.91 (d, J = 7.3 Hz, 3H), 1.12-2.40 (m, 24H), 3.24-3.39 (m, 7H), 3.54 (d, J = 10.4 Hz, 2H), 3.63 (m, 2H), 3.84 (s, 3H), 4.71 (s, 2H), 5.25 (d, J = 17.1 Hz, 1H), 5.38 (d, J = 12.2 Hz, 1H), 5.73 (d, J = 8.6 Hz, 1H), 6.50 (dd, J = 17.1, 11.0 Hz, 1H), 7.30 (s, 1H), 7.97 (d, J = 12.2 Hz, 1H), 8.60 (s, 1H), 14.8 (m, 1H). |
| 65 | quinolone with N-(3-methoxypropyl), 6-F, 7-Me, 8-OMe, 3-COOH | (ESI) 782.4(MH⁺) | (ESI) $C_{42}H_{57}FN_3O_{10}$ Calcd., 782.40280 Found, 782.40303 | (in CDCl$_3$): δ 0.76 (d, J = 6.7 Hz, 3H), 0.91 (d, J = 7.3 Hz, 3H), 1.12-2.36 (m, 26H), 3.20-3.45 (m, 9H), 3.55 (d, J = 9.8 Hz, 2H), 3.85 (m, 3H), 4.64 (s, 2H), 5.25 (d, J = 17.7 Hz, 1H), 5.38 (d, J = 11.0 Hz, 1H), 5.73 (d, J = 7.9 Hz, 1H), 6.50 (dd, J = 17.7, 11.0 Hz, 1H), 7.30 (s, 1H), 7.97 (d, J = 11.6 Hz, 1H), 8.63 (s, 1H), 14.8 (s, 1H). |

TABLE 11-continued

| 66 | 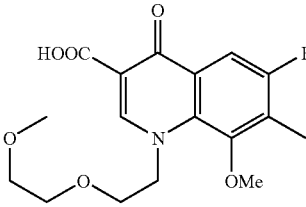 | (ESI) 812.4 (MH+) | (ESI) C$_{43}$H$_{59}$FN$_3$O$_{11}$ Calcd., 812.41336 Found, 812.41357 | (in CDCl$_3$): δ 0.76 (d, J = 6.7 Hz, 3H), 0.91 (d, J = 7.3 Hz, 3H), 1.13-2.36 (m, 24H), 3.25-3.55 (m, 13H), 3.77 (t, J = 4.3 Hz, 2H), 3.83 (s, 3H), 4.73 (t, J = 4.3 Hz, 2H), 5.25 (d, J = 17.7 Hz, 1H), 5.38 (d, J = 11.6 Hz, 1H), 5.73 (d, J = 8.6 Hz, 1H), 6.50 (dd, J = 17.1, 11.0 Hz, 1H), 7.33 (s, 1H), 7.97 (d, J = 11.6 Hz, 1H), 8.64 (s, 1H), 14.8 (s, 1H). |

TABLE 12

| 67 | 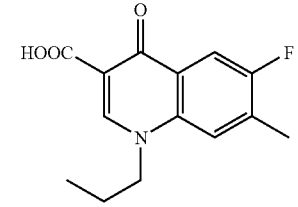 | (ESI) 722.4 (MH+) | (ESI) C$_{40}$H$_{53}$FN$_3$O$_8$ Calcd., 722.38167 Found, 722.38120 | (in CDCl$_3$): δ 0.76 (d, J = 6.7 Hz, 3H), 0.92 (d, J = 6.7 Hz, 3H), 1.06 (t, J = 7.3 Hz, 3H), 1.16-2.35 (m, 22H), 3.16 (br, 2H), 3.39 (d, J = 6.1 Hz, 1H), 3.48 (br, 1H), 3.80 (br, 2H), 4.24 (t, J = 7.3 Hz, 2H), 5.25 (d, J = 17.1 Hz, 1H), 5.36 (d, J = 11.6 Hz, 1H), 5.71 (d, J = 7.9 Hz, 1H), 6.48 (dd, J = 17.7, 11.0 Hz, 1H), 7.36 (s, 1H), 8.13 (d, J = 12.8 Hz, 1H), 8.67 (s, 1H). |
| 68 | 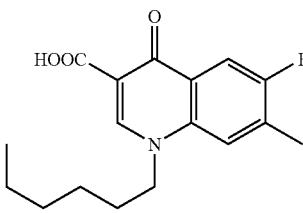 | (ESI) 764.4 (MH+) | (ESI) C$_{43}$H$_{59}$FN$_3$O$_8$ Calcd., 764.42862 Found, 764.42809 | (in CDCl$_3$): δ 0.76 (d, J = 6.7 Hz, 3H), 0.91 (d, J = 6.1 Hz, 6H), 1.13-2.35 (m, 32H), 2.95-3.10 (m, 2H), 3.37-3.41 (m 2H), 3.74 (br, 2H), 4.23 (t, J = 7.3 Hz, 2H), 5.25 (d, J = 17.1 Hz, 1H), 5.36 (d, J = 12.2 Hz, 1H), 5.71 (d, J = 8.6 Hz, 1H), 6.49 (dd, J = 17.7, 11.0 Hz, 1H), 7.36 (s, 1H), 8.07 (d, J = 12.8 Hz, 1H), 8.64 (s, 1H), 15.1 (s, 1H). |
| 69 | 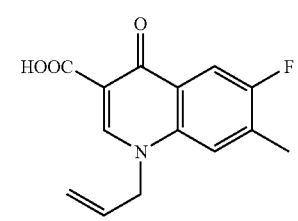 | (ESI) 720.4 (MH+) | (ESI) C$_{40}$H$_{51}$FN$_3$O$_8$ Calcd., 720.36602 Found, 720.36660 | (in CDCl$_3$): δ 0.76 (d, J = 6.7 Hz, 3H), 0.91 (d, J = 6.7 Hz, 3H), 1.13-1.25 (m, 4H), 1.40-1.81 (m, 11H), 1.95-2.35 (m, 9H), 3.00-3.05 (m, 2H), 3.36-3.41 (m, 2H), 3.72-3.75 (m, 2H), 4.86 (d, J = 4.9 Hz, 2H), 5.23-5.28 (m, 2H), 5.37 (d, J = 12.8 Hz, 1H), 5.46 (d, J = 10.4 Hz, 1H), 5.71 (d, J = 8.6 Hz, 1H), 5.98-6.00 (m, 1H), 6.49 (dd, J = 17.1 Hz, 11.0 Hz), 6.83 (d, J = 7.3 Hz, 1H), 7.33 (s, 1H), 8.06 (d, J = 12.8 Hz, 1H), 8.67 (s, 1H), 15.0 (s, 1H). |

TABLE 13

| 70 | (ESI) 734.4 (MH+) | (ESI) $C_{41}H_{53}FN_3O_8$ Calcd., 734.38167 Found, 734.38170 | (in CDCl$_3$): δ 0.52(q, J = 5.5 Hz, 2H), 0.76(d, J = 6.7 Hz, 3H), 0.84(q, J = 7.3 Hz, 2H), 0.91(d, J = 6.7 Hz, 3H), 1.14-1.25(m, 4H), 1.38-1.81(m, 12H), 1.97-2.35(m, 9H), 3.04-3.06(m, 2H), 3.37-3.41(m, 2H), 3.74-3.79(m, 2H), 4.08(d, J = 6.7 Hz, 2H), 5.25(d, J = 17.7 Hz, 1H), 5.37(d, J = 11.0 Hz, 1H), 5.72(d, J = 8.6 Hz, 1H), 6.49(dd, J = 17.1, 11.0 Hz, 2H), 6.95(d, J = 6.7 Hz, 1H), 7.34(s, 1H), 8.08 (d, J = 12.8 Hz, 1H), 8.74(s, 1H), 1.51(s, 1H). |
|---|---|---|---|

Example 9

14-[1-(3-Carboxy-1-cyclopropyl-1,4-dihydro-4-oxo-quinolin-7-yl)piperidine-4-carbonyl]carbamoyl-12-desethenyl-12-(1-propen-1-yl)mutilin

[Chem. 29]

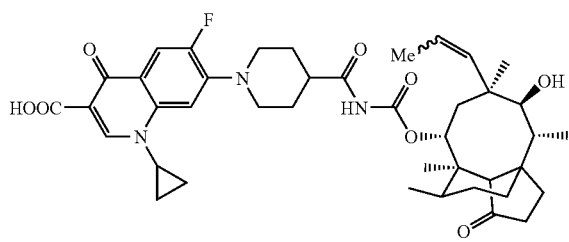

First Step (3R)-3-Deoxo-11-deoxy-12-desethenyl-3-methoxy-14-methoxymethoxy-11-oxo-12-(2-propyn-1-yl)-4-epimutilin

[Chem. 30]

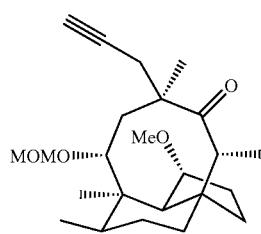

The reaction was carried out using 2.00 g (5.67 mmol) of (3R)-3-deoxo-11-deoxy-12-desethenyl-3-methoxy-14-methoxymethoxy-11-oxo-4-epimutilin, 0.51 mL (6.81 mmol) of propargyl bromide, and 13.6 mL (6.81 mmol) of potassium bis(trimethylsilyl)amide (0.5 mol/L toluene solution) in accordance with First Step of Example 2, and the obtained residue was purified by silica gel column chromatography (hexane:ethyl acetate=4:1) to obtain 2.32 g of the yellow oily heading compound (yield 100%).

MS (FAB+) m/z: 329 (MH+—HOCH$_2$OCH$_3$).

HRMS (FAB+) for $C_{22}H_{33}O_2$ (MH+—HOCH$_2$OCH$_3$): calcd, 329.2481. found, 329.2467.

Second Step (3R)-3-Deoxo-11-deoxy-12-desethenyl-3-methoxy-14-methoxymethoxy-11-oxo-12-(1-propyn-1-yl)-4-epimutilin

[Chem. 31]

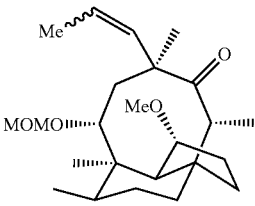

To a solution (150 mL) of the compound of First Step (13.3 g, 34.0 mmol) in tetrahydrofuran was added 3.82 g (34.0 mmol) of potassium t-butoxide under ice-cooling, followed by stirring for 12 hours while naturally warming. The reaction mixture was poured into a diluted aqueous citric acid solution, and the solvent was evaporated under reduced pressure. The residue was extracted with ethyl acetate (100 mL×3), the combined organic layer was washed with saturated brine (50 mL), dried over anhydrous magnesium sulfate, and filtered, and the solvent was evaporated. The obtained residue was purified by silica gel column chromatography (hexane:ethyl acetate=8:1) to obtain 13.2 g of the yellow oily heading compound (yield 99%).

MS (FAB+) m/z: 391 (MH+).

HRMS (FAB+) for $C_{24}H_{39}O_4$ (MH+): calcd, 391.2848. found, 391.2871.

Third Step (3R)-3-Deoxo-11-deoxy-12-desethenyl-3-methoxy-14-methoxymethoxy-11-oxo-12-(1-propen-1-yl)-4-epimutilin

[Chem. 32]

To a solution (250 mL) of the compound of Second Step (13.2 g, 33.8 mmol) in toluene was added 1.30 g (10% by weight) of a Lindlar catalyst, followed by catalytic reduction at normal temperature at 98.1 KPa for 5 hours. The reaction mixture was filtered over Celite, and the residue was washed with ethyl acetate. The combined filtrate was evaporated under reduced pressure to obtain 13.3 g of the heading compound as a colorless oily substance (yield 100%).

MS (FAB$^+$) m/z: 393 (MH$^+$).

HRMS (FAB$^+$) for $C_{24}H_{41}O_4$ (MH$^+$): calcd, 393.3005. found, 393.3010.

Fourth Step (3R)-3-Deoxo-11-deoxy-12-desethenyl-3-methoxy-11-oxo-12-(1-propen-1-yl)-4-epimutilin

[Chem. 33]

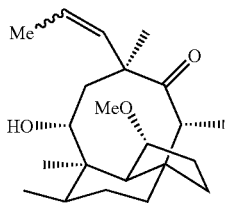

The reaction was carried out using the compound of Third Step (13.3 g, 33.9 mmol) and p-toluenesulfonic acid monohydrate (6.44 g, 33.9 mmol) in accordance with the Second Step of Example 2, and the obtained residue was purified by silica gel column chromatography (hexane:ethyl acetate=4:1) to obtain 10.1 g of the heading compound as a colorless powdery substance (yield 86%).

MS (FAB$^+$) (m/z): 331 (MH$^+$—H$_2$O).

HRMS (FAB$^+$) for $C_{22}H_{35}O_2$ (MH$^+$—H$_2$O): calcd, 331.2637. found, 331.2645.

Fifth Step (3R)-3-Deoxo-11-deoxy-12-desethenyl-3-methoxy-11-oxo-12-(1-propen-1-yl)-14-[1-(2,2,2-trichloroethoxycarbonyl)piperidine-4-carbonyl]carbamoyl-4-epimutilin

[Chem. 34]

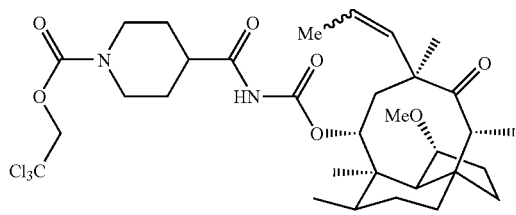

To a solution (13 mL) of 450 mg (1.29 mmol) of the compound of Fourth Step in methylene chloride was added 484 mg (3.23 mmol) of silver cyanate under stirring at room temperature, and an acid chloride prepared from 591 mg (1.94 mmol) of the carboxylic acid of Reference Example 1 and oxalyl chloride, and 0.27 mL (1.94 mmol) of triethylamine were added thereto under stirring at −40° C. under an argon atmosphere, followed by stirring for 15 hours while naturally warming under light shielding (with an aluminum foil). The light shielding was discontinued, and to the reaction mixture were added ethyl acetate (13 mL) and Celite (4.84 g), followed by stirring for 15 minutes. The reaction mixture was filtered over Celite, and the residue was washed with ethyl acetate. The combined organic layer was evaporated under reduced pressure, and to the residue was added water, followed by extraction with ethyl acetate (40 mL×3). The combined organic layer was washed with saturated brine (40 mL), dried over anhydrous magnesium sulfate, and filtered, and the solvent was evaporated. The obtained residue was purified by silica gel column chromatography (hexane:ethyl acetate=2:1) to obtain 449 mg of the colorless powdery heading compound (yield 51%).

MS (ESI$^-$) m/z: 675.2 (MH$^-$).

HRMS (ESI$^-$) for $C_{32}H_{46}Cl_3N_2O_7$ (MH$^-$): calcd, 675.23706. Found, 675.23651.

Sixth Step (3R)-3-Deoxo-11-deoxy-12-desethenyl-3-methoxy-11-oxo-14-(piperidine-4-carbonyl)carbamoyl-12-(1-propen-1-yl)-4-epimutilin

[Chem. 35]

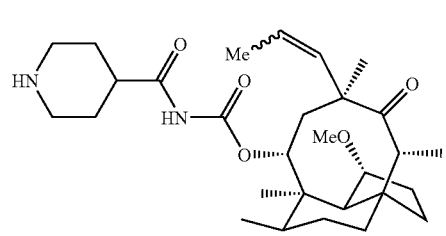

To 430 mg (0.63 mmol) of the compound of Fifth Step was added acetic acid (4.30 mL), and 206 mg (3.15 mmol) of zinc was added thereto, followed by stirring for 25 hours. Further, zinc was added thereto in the same amount, followed by stirring at room temperature for 26 hours at room temperature. The reaction mixture was filtered over Celite, and the residue was washed with ethyl acetate and water. The aqueous layer was extracted with ethyl acetate (10 mL×3), and the combined organic layer was extracted with a diluted aqueous citric acid solution (10 mL×3). The aqueous layer was alkalified with the addition of a saturated aqueous sodium hydrogen carbonate solution, and extracted with ethyl acetate (10 mL×3). The combined organic layer was washed with saturated brine (10 mL), dried over anhydrous magnesium sulfate and filtered, and the solvent was evaporated to obtain 282 mg of the heading compound as a colorless powdery crystal (yield 89%).

MS (ESI$^+$) m/z: 503.31 (MH$^+$).

HRMS (ESI$^+$) for $C_{29}H_{47}N_2O_5$ (MH+): calcd, 503.34850. found, 503.34896.

Seventh Step

12-Desethenyl-14-(piperidine-4-carbonyl)carbamoyl-12-(1-propen-1-yl)mutilin

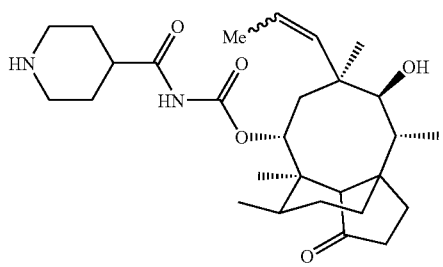

[Chem. 36]

To a solution (400 mL) of the compound of Sixth Step (40.0 g, 79.6 mmol) in dioxane was added concentrated hydrochloric acid (400 mL) while stirring under ice-cooling, followed by stirring for about 3 hours while naturally warming. Under stirring under ice-cooling, the mixed reaction liquid was alkalified with the addition of a saturated aqueous sodium hydrogen carbonate solution (pH was about 8), and the aqueous layer was then extracted with ethyl acetate (500 mL×3). The combined organic layer was washed with saturated brine (500 mL), dried over anhydrous sodium sulfate, and filtered, and the solvent was evaporated. The obtained residue was purified by silica gel column chromatography (NH, ethyl acetate, and then ethyl acetate:methanol=20:1) to obtain 29.7 g of the heading compound as a colorless powdery crystal (yield 77%).

MS (ESI$^+$) m/z: 489.3 (MH$^+$).

HRMS (ESI$^+$) for $C_{28}H_{45}N_2O_5$: calcd, 489.33285 (MH$^+$); found, 489.33244.

Eighth Step

14-[1-(3-Carboxy-1-cyclopropyl-6-fluoro-1,4-dihydro-4-oxoquinolin-7-yl)piperidine-4-carbonyl]carbamoyl-12-desethenyl-12-(1-propen-1-yl)mutilin

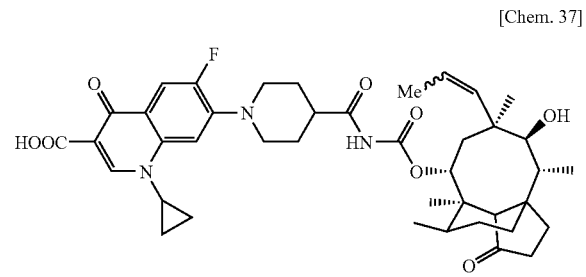

[Chem. 37]

The reaction was carried out using a solution of the compound of Seventh Step (300 mg, 0.614 mmol) and 1-cyclopropyl-6,7-difluoro-1,4-dihydro-4-oxo-3-quinolinecarboxylic acid (148 mg, 0.558 mmol) in acetonitrile (6.1 mL) in accordance with the method of Example 1, and the purification was carried out by silica gel column chromatography (chloroform/methanol=50:1→20:1) to obtain the heading compound (324 mg) (yield 79%).

MS (ESI$^+$) m/z: 734.4 (MH$^+$).

HRMS (ESI$^+$) for $C_{41}H_{53}FN_3O_8$ (MH$^+$): calcd, 734.38167. found, 734.38163.

1H NMR (400 MHz, CDCl$_3$) δ 0.75 (d, J=6.7 Hz, 3H), 0.98 (d, J=6.7 Hz, 3H), 1.12-2.43 (m, 22H), 1.39 (s, 3H), 1.42 (s, 3H), 1.75 (d, J=6.1 Hz, 3H), 3.00-3.10 (m, 2H), 3.35 (t, J=6.7 Hz, 1H), 3.40-3.50 (m, 2H), 3.73-3.84 (m, 2H), 5.60 (d, J=8.0 Hz, 1H), 5.68-5.79 (m, 2H), 7.33 (brs, 1H), 7.37 (d, J=7.3 Hz, 1H), 8.04 (d, J=12.8 Hz, 1H), 8.78 (s, 1H), 15.04 (s, 1H).

Example 10

The inventive compounds 72 to 112 were synthesized using the same procedure as in Example 9.

TABLE 14

| No. | R | MS (m/z) | HRMS (m/z) | $^1$H NMR |
|---|---|---|---|---|
| 72 | HOOC-quinolone-F, N-ethyl, 7-methyl substituent | (ESI) 722.4 (MH$^+$) | (ESI) $C_{40}H_{53}FN_3O_8$ Calcd., 722.38167 Found, 722.38093 | (in CDCl$_3$): δ 0.75(d, J = 6.7 Hz, 3H), 0.98(d, J = 7.3 Hz, 3H), 1.10-1.29 (m, 2H), 1.33-1.89(m, 18H), 1.89-2.47(m, 10H), 3.01-3.07(m, 2H), 3.35(t, J = 6.7 Hz, 1H), 3.40-3.55(m, 1H), 3.65-3.84(m, 2H), 4.32(q, J = 7.3 Hz, 2H), 5.60(d, J = 7.9 Hz, 1H), 5.69-5.84 (m, 2H), 6.85(d, J = 6.7 Hz, 1H), 7.31(s, 1H), 8.08(d, J = 12.8 Hz, 1H), 8.68(s, 1H), 15.1 (br s, 1H). |

TABLE 14-continued

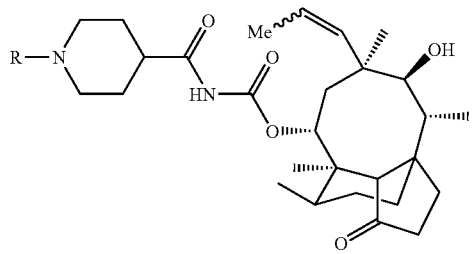

| No. | R | MS (m/z) | HRMS (m/z) | $^1$H NMR |
|---|---|---|---|---|
| 73 | ![HOOC-quinolone with 6-F, 7-Me, 8-F, N-ethyl] | (ESI) 740.4 (MH$^+$) | (ESI) $C_{40}H_{52}F_2N_3O_8$ Calcd., 740.37225 Found, 740.37204 | (in CDCl$_3$): δ 0.75(d, J = 6.7 Hz, 3H), 0.99(d, J = 6.7 Hz, 3H), 1.12-2.44 (m, 25H), 3.28-3.60(m, 6H), 4.41-4.54(m, 2H), 5.61(d, J = 7.3 Hz, 1H), 5.68-5.83(m, 2H), 7.36 (s, 1H), 7.97(dd, J = 12.2, 1.8 Hz, 1H), 8.61 (s, 1H), 14.7(s, 1H). |

TABLE 15

| 74 | ![HOOC-quinolone with 6-F, 7-Me, 8-F, N-fluoroethyl] | (ESI) 758.4 (MH$^+$) | (ESI) $C_{40}H_{51}F_3N_3O_8$ Calcd., 758.36282 Found, 758.36316 | (in CDCl$_3$): δ 0.74(d, J = 7.3 Hz, 3H), 0.99(d, J = 7.3 Hz, 3H), 1.10-2.45 (m, 27H), 3.27-3.58(m, 6H), 4.67-4.91(m, 4H), 5.60(d, J = 7.3 Hz, 1H), 5.71-5.81(m, 2H), 7.25 (s, 1H), 8.00(dd, J = 11.6, 1.8 Hz, 1H), 8.59 (s, 1H), 14.5(s, 1H). |
| 75 | ![HOOC-quinolone with 6-F, 7-Me, N-fluoroethyl] | (ESI) 740.4 (MH$^+$) | (ESI) $C_{40}H_{52}F_2N_3O_8$ Calcd., 740.37225 Found, 740.37208 | (in CDCl$_3$): δ 0.64(d, J = 6.1 Hz, 3H), 0.87(d, J = 6.7 Hz, 3H), 0.95-2.99 (m, 30H), 3.72(d, J = 12.2 Hz, 2H), 4.61(d, J = 6.1 Hz, 1H), 4.73-5.03 (m, 4H), 5.33-5.63(m, 3H), 7.21(d, J = 6.7 Hz, 1H), 7.91(d, J = 13.4 Hz, 1H), 8.87(s, 1H), 10.4(s, 1H), 15.3(s, 1H). |
| 76 | ![HOOC-quinolone with 6-F, 7-Me, 8-F, N-cyclopropyl] | (ESI) 752.4 (MH$^+$) | (ESI) $C_{41}H_{52}F_2N_3O_8$ Calcd., 752.37225 Found, 752.37201 | (in CDCl$_3$): δ 0.75(d, J = 7.3 Hz, 3H), 0.99(d, J = 6.7 Hz, 3H), 1.16-2.43 (m, 33H), 3.28-3.66(m, 6H), 3.93-4.07(m, 1H), 5.61(d, J = 8.0 Hz, 1H), 5.71-5.80(m, 2H), 7.92 (dd, J = 11.6, 1.8 Hz, 1H), 14.6(s, 1H). |
| 77 | ![HOOC-quinolone with 6-F, 7-Me, 8-Cl, N-cyclopropyl] | (ESI) 768.3 (MH$^+$) | (ESI) $C_{41}H_{52}ClFN_3O_8$ Calcd., 768.34269 Found, 768.34321 | (in CDCl$_3$): δ 0.75(d, J = 6.7 Hz, 3H), 0.93-1.04 (m, 5H), 1.16-2.43(m, 27H), 3.31-3.51(m, 6H), 4.32-4.38(m, 1H), 5.62 (d, J = 7.3 Hz, 1H), 5.72-5.81(m, 2H), 7.30 (s, 1H), 8.04(d, J = 11.6 Hz, 1H), 8.91(s, 1H), 14.4(s, 1H). |

TABLE 16

| | Structure | MS | HRMS | NMR |
|---|---|---|---|---|
| 78 | (naphthyridine core with 6-F, 7-methyl, N-cyclopropyl, 3-COOH) | (ESI) 735.4 (MH+) | (ESI) C$_{40}$H$_{52}$FN$_4$O$_8$ Calcd., 735.37692 Found, 735.37683 | (in CDCl$_3$): δ 0.74(d, J = 6.7 Hz, 3H), 0.99(d, J = 6.7 Hz, 3H), 1.08-2.44 (m, 31H), 3.28-3.37(m, 3H), 3.60-3.65(m, 2H), 4.63-4.66(m, 2H), 5.60 (d, J = 7.9 Hz, 1H), 5.70-5.80(m, 2H), 7.35(s, 1H), 8.08(d, J = 13.4 Hz, 1H), 8.74(s, 1H), 15.0 (s, 1H). |
| 79 | (naphthyridine core with 6-F, 7-methyl, N-(fluorocyclopropyl), 3-COOH) | (ESI) 753.4 (MH+) | (ESI) C$_{40}$H$_{51}$F$_2$N$_4$O$_8$ Calcd., 753.36749 Found, 753.36720 | (in CDCl$_3$): δ 0.74(d, J = 6.7 Hz, 3H), 0.99(d, J = 6.7 Hz, 3H), 1.23-2.41 (m, 28H), 3.28-3.37(m, 3H), 3.55-3.60(m, 2H), 3.69-3.76(m, 1H), 4.61 (d, J = 12.8 Hz, 2H), 4.84-5.03(m, 1H), 5.60 (d, J = 7.9 Hz, 1H), 5.70-5.80(m, 2H), 7.37(s, 1H), 8.09(d, J = 13.4 Hz, 1H), 8.77(s, 1H), 14.9 (s, 1H). |
| 80 | (quinolone core with 6-F, 7-methyl, N-(fluorocyclopropyl), 3-COOH) | (ESI) 752.4 (MH+) | (ESI) C$_{41}$H$_{52}$F$_2$N$_3$O$_8$ Calcd., 752.37225 Found, 752.37165 | (in CDCl$_3$): δ 0.75(d, J = 6.7 Hz, 3H), 0.99(d, J = 6.7 Hz, 3H), 1.09-2.47 (m, 29H), 3.00-3.12(m, 2H), 3.35(t, J = 6.7 Hz, 1H), 3.40-3.56(m, 2H), 3.70-3.84(m, 2H), 4.98-5.21(m, 1H), 5.60(d, J = 7.9 Hz, 1H), 5.68-5.81 (m, 2H), 7.20-7.33(m, 2H), 8.05(d, J = 12.8 Hz, 1H), 8.79(s, 1H), 14.9(s, 1H). |
| 81 | (quinolone core with 6,8-diF, 7-methyl, N-(fluorocyclopropyl), 3-COOH) | (ESI) 770.4 (MH+) | (ESI) C$_{41}$H$_{51}$F$_3$N$_3$O$_8$ Calcd., 770.36282 Found, 770.36302 | (in CDCl$_3$): δ 0.75(d, J = 6.7 Hz, 3H), 0.99(d, J = 7.3 Hz, 3H), 1.09-2.48 (m, 29H), 3.26-3.62(m, 6H), 3.84-3.95(m, 1H), 4.81-5.04(m, 1H), 5.61 (d, J = 7.9 Hz, 1H), 5.68-5.83(m, 2H), 7.28 (s, 1H), 7.92(dd, J = 11.6, 1.2 Hz, 1H), 8.78 (s, 1H), 14.5(s, 1H). |

TABLE 17

| | Structure | MS | HRMS | NMR |
|---|---|---|---|---|
| 82 | (quinolone core with 6-F, 8-Cl, 7-methyl, N-(fluorocyclopropyl), 3-COOH) | (ESI) 786.3 (MH+) | (ESI) C$_{41}$H$_{51}$ClF$_2$N$_3$O$_8$ Calcd., 786.33327 Found, 786.33312 | (in CDCl$_3$): δ 0.75(d, J = 6.7 Hz, 3H), 0.99(d, J = 6.7 Hz, 3H), 1.13-2.46 (m, 29H), 3.31-3.51(m, 6H), 4.19-4.26(m, 1H), 4.79-5.00(m, 1H), 5.62 (d, J = 7.9 Hz, 1H), 5.71-5.82(m, 2H), 7.30(s, 1H), 8.06(d, J = 11.0 Hz, 1H), 8.80(d, J = 2.4 Hz, 1H), 14.3(s, 1H). |
| 83 | (naphthyridine core with 6-F, 7-methyl, N-tert-butyl, 3-COOH) | (ESI) 751.4 (MH+) | (ESI) C$_{41}$H$_{56}$FN$_4$O$_8$ Calcd., 751.40822 Found, 751.40845 | (in CDCl$_3$): δ 0.75(d, J = 7.3 Hz, 3H), 0.99(d, J = 6.7 Hz, 3H), 1.13-2.42 (m, 33H), 3.27-3.37(m, 3H), 3.59(br, 1H), 4.52-4.55(m, 1H), 5.61(d, J = 7.9 Hz, 1H), 5.72-5.80 (m, 2H), 7.30(s, 1H), 8.16(d, J = 13.4 Hz, 1H), 9.00(s, 1H), 15.0(s, 1H). |

TABLE 17-continued

| | | | | |
|---|---|---|---|---|
| 84 | 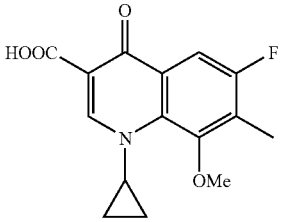 | (ESI) 764.4 (MH+) | (ESI) C₄₂H₅₅FN₃O₉ Calcd., 764.39223 Found, 764.39174 | (in CDCl₃): 0.75(d, J = 6.7 Hz, 3H), 0.99(d, J = 6.7 Hz, 3H), 0.94-2.45 (m, 22H), 1.39(s, 3H), 1.42(s, 3H), 1.75(d, = 5.5 Hz, 3H), 3.24-3.48 (m, 4H), 3.55-3.64(m, 2H), 3.80(s, 3H), 3.96-4.08(m, 1H), 5.61(d = 8.0 Hz, 1H), 5.70-5.80 (m, 2H), 7.32(brs, 1H), 7.88(d, J = 12.2 Hz, 1H), 8.82(s, 1H), 14.8(brs, 1H). |
| 85 | 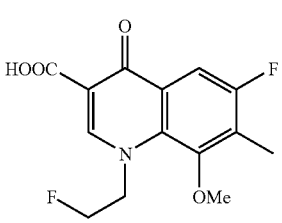 | (ESI) 770.4 (MH+) | (ESI) C₄₁H₅₄F₂N₃O₉ Calcd., 770.38281 Found, 770.38229 | (in CDCl₃): δ 0.75(d, J = 6.7 Hz, 3H), 0.99(d, J = 7.3 Hz, 3H), 1.10-2.45 (m, 27H), 3.22-3.59(m, 6H), 3.84(s, 3H), 4.65(t, J = 4.3 Hz, 1H), 4.76-4.81(m, 2H), 4.86(t, J = 4.3 Hz, 1H), 5.61(d, J = 7.9 Hz, 1H), 5.70-5.80 (m, 2H), 7.30(s, 1H), 7.98(d, J = 11.6 Hz, 1H), 8.59(s, 1H), 14.7(s, 1H). |

TABLE 18

| | | | | |
|---|---|---|---|---|
| 86 | 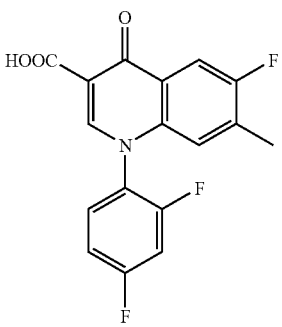 | (ESI) 806.3 (MH+) | (ESI) C₄₄H₅₁F₃N₃O₈ Calcd., 806.36282 Found, 806.36285 | (in CDCl₃): δ 0.72(d, J = 6.7 Hz, 3H), 0.98(d, J = 6.7 Hz, 3H), 1.09-2.45 (m, 27H), 2.75-2.90(m, 2H), 3.34(t, J = 6.7 Hz, 2H), 3.44-3.63(m, 2H), 5.57(d, J = 7.9 Hz, 1H), 5.68-5.80(m, 2H), 6.24 (d, J = 6.7 Hz, 1H), 7.16-7.33(m, 3H), 7.45-7.54(m, 1H), 8.08(d, J = 12.8 Hz, 1H), 8.60(s, 1H), 14.8(s, 1H). |
| 87 | 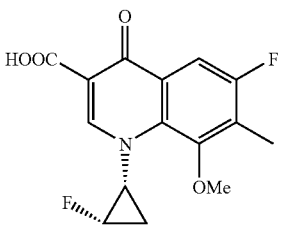 | (ESI) 782.4 (MH+) | (ESI) C₄₂H₅₄F₂N₃O₉ Calcd., 782.38281 Found, 782.38333 | (in CDCl₃): δ 0.75(d, J = 6.7 Hz, 3H), 0.99(d, J = 7.3 Hz, 3H), 1.13-2.45 (m, 29H), 3.22-3.65(m, 6H), 3.82(s, 3H), 3.88-3.95(m, 1H), 4.73-4.94 (m, 1H), 5.61(d, J = 7.9 Hz, 1H), 5.71-5.81(m, 2H), 7.29(s, 1H), 7.89 (d, J = 11.6 Hz, 1H), 8.78(s, 1H), 14.7(s, 1H). |
| 88 | 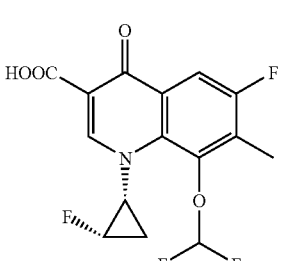 | (ESI) 818.4 (MH+) | (ESI) C₄₂H₅₂F₄N₃O₉ Calcd., 818.36397 Found, 818.36316 | (in CDCl₃): δ 0.73(d, J = 6.7 Hz, 3H), 0.97(d, J = 6.7 Hz, 3H), 1.10-2.42 (m, 28H), 3.19-3.36(m, 6H), 4.00-4.06(m, 1H), 4.77-5.00(m, 1H), 5.59 (d, J = 7.9 Hz, 1H), 5.71-5.75(m, 2H), 6.53(dd, J = 77.6, 72.7 Hz, 1H), 7.28(s, 1H), 8.03(d, J = 11.6 Hz, 1H), 8.79(s, 1H), 14.3(s, 1H). |

TABLE 19

| | | | | |
|---|---|---|---|---|
| 89 | [structure] | (ESI) 764.4 (MH+) | (ESI) $C_{42}H_{55}FN_3O_9$ Calcd., 764.39223 Found, 764.39181 | (in CDCl$_3$): δ 0.75(d, J = 6.7 Hz, 3H), 0.99(d, J = 6.7 Hz, 3H), 1.13-2.42 (m, 29H), 2.89-3.02(m, 2H), 3.35-3.42(m, 2H), 3.75(d, J = 11.6 Hz, 1H), 3.84(s, 3H), 3.88-3.98 (m, 2H), 4.74-4.93(m, 1H), 5.62(d, J = 7.9 Hz, 1H), 5.72-5.80(m, 2H), 7.18(d, J = 9.2 Hz, 1H), 7.29(s, 1H), 8.18(d, J = 8.6 Hz, 1H), 8.79(s, 1H), 14.9(s, 1H). |
| 90 | [structure] | (ESI) 734.4 (MH+) | (ESI) $C_{41}H_{53}FN_3O_8$ Calcd., 734.38167 Found, 734.38206 | (in CDCl$_3$): δ 0.75(d, J = 6.7 Hz, 3H), 0.99(d, J = 6.7 Hz, 3H), 1.08-2.48 (m, 31H), 3.01-3.11(m, 2H), 3.32-3.48(m, 2H), 3.64-3.73(m, 2H), 3.98-4.08(m, 1H), 5.61(d, J = 7.9 Hz, 1H), 5.69-5.82 (m, 2H), 7.17(dd, J = 8.6, 7.3 Hz, 1H), 7.28(s, 1H), 8.19(dd, J = 9.2, 1.2 Hz, 1H), 8.81(s, 1H), 14.8(s, 1H). |
| 91 | [structure] | (ESI) 750.4 (MH+) | (ESI) $C_{41}H_{53}FN_3O_9$ Calcd., 750.37658 Found, 750.37643 | (in CDCl$_3$): δ 0.75(d, J = 6.7 Hz, 3H), 0.99(d, J = 6.7 Hz, 3H), 1.10-2.45 (m, 30H), 3.23-3.56(m, 6H), 4.31-4.37(m, 1H), 4.41-4.50(m, 2H), 5.61 (d, J = 7.3 Hz, 1H), 5.70-5.81(m, 2H), 7.29 (s, 1H), 7.74(d, J = 12.2 Hz, 1H), 8.60(s, 1H), 15.0(s, 1H). |

TABLE 20

| | | | | |
|---|---|---|---|---|
| 92 | [structure] | (ESI) 732.4 (MH+) | (ESI) $C_{41}H_{54}N_3O_9$ Calcd., 732.38600 Found, 732.38601 | (in CDCl$_3$): δ 0.75(d, J = 6.7 Hz, 3H), 0.98(d, J = 6.7 Hz, 3H), 1.10-2.45 (m, 30H), 2.95-3.13(m, 2H), 3.32-3.46(m, 2H), 3.67-3.86(m, 2H), 4.34-4.53(m, 3H), 5.61(d, J = 7.9 Hz, 1H), 5.69-5.81 (m, 2H), 7.30(d, J = 8.6 Hz, 1H), 7.34(s, 1H), 8.06(d, J = 9.2 Hz, 1H), 8.63(s, 1H), 15.1(s, 1H). |
| 93 | [structure] | (ESI) 768.4 (MH+) | (ESI) $C_{41}H_{52}F_2N_3O_9$ Calcd., 768.36716 Found, 768.36744 | (in CDCl$_3$): δ 0.75(d, J = 6.7 Hz, 3H), 0.99(d, J = 6.7 Hz, 3H), 1.09-2.46 (m, 29H), 3.20-3.56(m, 6H), 4.31-4.91(m, 5H), 5.61(d, J = 7.9 Hz, 1H), 5.69-5.81(m, 2H), 7.77 (d, J = 11.6 Hz, 1H), 8.60(s, 1H), 14.8(s, 1H). |

TABLE 20-continued

| # | Structure | MS | Formula / HRMS | ¹H NMR |
|---|---|---|---|---|
| 94 | (quinolone with HOOC, fused oxazine ring bearing CH₂F, methyl substituent) | (ESI) 750.4 (MH⁺) | (ESI) C$_{41}$H$_{53}$FN$_3$O$_9$ Calcd., 750.37658 Found, 750.37741 | (in CDCl$_3$): δ 0.74(d, J = 6.7 Hz, 3H), 0.98(d, J = 7.3 Hz, 3H), 1.10-2.44 (m, 31H), 2.96-3.17(m, 2H), 3.35(d, J = 6.1 Hz, 1H), 3.38-3.49(m, 1H), 3.69(d, J = 11.6 Hz, 1H), 3.80(d, J = 11.6 Hz, 1H), 4.59-4.91(m, 1H), 5.60(d, J = 7.9 Hz, 1H), 5.68-5.80(m, 2H), 7.29(s, 1H), 7.33(d, J = 9.2 Hz, 1H), 8.09(d, J = 9.2 Hz, 1H), 8.62(s, 1H), 14.8(s, 1H). |

TABLE 21

| # | Structure | MS | Formula / HRMS | ¹H NMR |
|---|---|---|---|---|
| 95 | (quinolone with HOOC, F, Me, OCHF₂, N-cyclopropyl) | (ESI) 800.4 (MH⁺) | (ESI) C$_{42}$H$_{53}$F$_3$N$_3$O$_9$ Calcd., 800.37339 Found, 800.37338 | (in CDCl$_3$): δ 0.75(d, J = 6.7 Hz, 3H), 0.99(d, J = 7.3 Hz, 5H), 1.10-2.46 (m, 29H), 3.29-3.59(m, 6H), 4.10-4.18(m, 1H), 5.61(d, J = 7.9 Hz, 1H), 5.69-5.81(m, 2H), 6.49 (t, J = 75.2 Hz, 1H), 7.30 (s, 1H), 8.04(d, J = 11.6 Hz, 1H), 8.86(s, 1H). |
| 96 | (quinolone with HOOC, Me, OCHF₂, N-cyclopropyl) | (ESI) 782.4 (MH⁺) | (ESI) C$_{42}$H$_{54}$F$_2$N$_3$O$_9$ Calcd., 782.38281 Found, 782.38294 | (in CDCl$_3$): δ 0.75(d, J = 6.7 Hz, 3H), 0.96-1.02 (m, 5H), 1.10-2.45(m, 29H), 2.97-3.09(m, 2H), 3.31-3.48(m, 2H), 3.65-3.74(m, 2H), 4.18-4.25 (m, 1H), 5.61(d, J = 7.9 Hz, 1H), 5.69-5.82(m, 2H), 6.52(t, J = 75.8 Hz, 1H), 7.23(d, J = 9.2 Hz, 2H), 7.32(s, 1H), 8.33 (d, J = 9.2 Hz, 1H), 8.87 (s, 1H), 14.7(s, 1H). |
| 97 | (quinolone with HOOC, Me, OMe, N-cyclopropyl) | (ESI) 746.4 (MH⁺) | (ESI) C$_{42}$H$_{56}$N$_3$O$_9$ Calcd., 746.40165 Found, 746.40084 | (in CDCl$_3$): δ 0.75(d, J = 6.7 Hz, 3H), 0.95-1.05 (m, 5H), 1.11-2.45(m, 28H), 2.91-3.03(m, 2H), 3.30-3.52(m, 2H), 3.78-3.87(br, 2H), 3.82(s, 3H), 4.04-4.12(m, 1H), 5.61(d, J = 7.9 Hz, 1H), 5.70-5.83(m, 2H), 7.36 (s, 1H), 8.17(d, J = 8.6 Hz, 1H), 8.30(s, 1H), 15.0(s, 1H). |

TABLE 22

| # | Structure | MS | Formula / HRMS | ¹H NMR |
|---|---|---|---|---|
| 98 | (quinolone with HOOC, F, Me, OMe, N-Me) | (ESI) 738.4 (MH⁺) | (ESI) C$_{40}$H$_{53}$FN$_3$O$_9$ Calcd., 738.37658 Found, 738.37637 | (in CDCl$_3$): δ 0.75(d, J = 6.7 Hz, 3H), 0.99(d, J = 6.7 Hz, 3H), 1.09-2.45 (m, 26H), 3.25-3.61(m, 6H), 3.86(s, 3H), 4.20 (s, 3H), 5.61(d, J = 7.9 Hz, 1H), 5.69-5.80(m, 2H), 7.29(s, 1H), 7.94 (d, J = 12.2 Hz, 1H), 8.55(s, 1H), 14.8(s, 1H). |

TABLE 22-continued

| | | | | |
|---|---|---|---|---|
| 99 | *(structure: quinolone with HOOC, F, Me, OMe, N-ethyl)* | (ESI) 752.4 (MH⁺) | (ESI) $C_{41}H_{55}FN_3O_9$ Calcd., 752.39223 Found, 752.39136 | (in CDCl$_3$): δ 0.75(d, J = 6.7 Hz, 3H), 0.99(d, J = 6.7 Hz, 3H), 1.11-2.47 (m, 30H), 3.26-3.60(m, 6H), 3.85(s, 3H), 4.58 (q, J = 6.7 Hz, 2H), 5.61 (d, J = 7.9 Hz, 1H), 5.70-5.82(m, 2H), 7.33 (s, 1H), 7.96(d, J = 12.2 Hz, 1H), 8.61(s, 1H), 14.9(s, 1H). |
| 100 | *(structure: quinolone with HOOC, F, Me, OMe, N-propyl)* | (ESI) 766.4 (MH⁺) | (ESI) $C_{42}H_{57}FN_3O_9$ Calcd., 766.40788 Found, 766.40780 | (in CDCl$_3$): δ 0.75(d, J = 6.7 Hz, 3H), 0.89(d, J = 7.3 Hz, 3H), 0.99(d, J = 6.7 Hz, 3H), 1.12-2.46 (m, 29H), 3.25-3.60(m, 6H), 3.84(s, 3H), 4.46(t, J = 7.3 Hz, 2H), 5.61(d, J = 7.9 Hz, 1H), 5.70-5.81(m, 2H), 7.30(s, 1H), 7.96(d, J = 11.6 Hz, 1H), 8.59(s, 1H), 14.9(s, 1H). |
| 101 | *(structure: quinolone with HOOC, F, Me, OMe, N-butyl)* | (ESI) 780.4 (MH⁺) | (ESI) $C_{43}H_{59}FN_3O_9$ Calcd., 780.42353 Found, 780.42283 | (in CDCl$_3$): δ 0.75(d, J = 6.7 Hz, 3H), 0.93(t, J = 7.3Hz, 3H), 0.99(d, J = 6.7 Hz, 3H), 1.10-2.47 (m, 39H), 3.25-3.62(m, 6H), 3.83(s, 3H), 4.50(t, J = 7.3 Hz, 2H), 5.61(d, J = 7.9 Hz, 1H), 5.69-5.82(m, 2H), 7.96(d, J = 12.2 Hz, 1H), 8.58(s, 1H), 14.9(s, 1H). |

TABLE 23

| | | | | |
|---|---|---|---|---|
| 102 | *(structure: quinolone with HOOC, F, Me, OMe, N-pentyl)* | (ESI) 794.4 (MH⁺) | (ESI) $C_{44}H_{61}FN_3O_9$ Calcd., 794.43918 Found, 794.43906 | (in CDCl$_3$): δ 0.75(d, J = 6.7 Hz, 3H), 0.88(t, J = 6.7 Hz, 3H), 0.99(d, J = 6.7 Hz, 3H), 1.10-2.46 (m, 31H), 3.23-3.63(m, 8H), 3.83(s, 3H), 4.48(t, J = 7.3 Hz, 2H), 5.61(d, J = 7.9 Hz, 1H), 5.69-5.82(m, 2H), 7.28(s, 1H), 7.96(d, J = 11.6 Hz, 1H), 8.58(s, 1H), 14.9(s, 1H). |
| 103 | *(structure: quinolone with HOOC, F, Me, OMe, N-hexyl)* | (ESI) 808.5 (MH⁺) | (ESI) $C_{45}H_{63}FN_3O_9$ Calcd., 808.45483 Found, 808.45467 | (in CDCl$_3$): δ 0.75(d, J = 6.7 Hz, 3H), 0.87(t, J = 6.7 Hz, 3H), 0.99(d, J = 6.7 Hz, 3H), 1.10-2.46 (m, 35H), 3.25-3.60(m, 6H), 3.83(s, 3H), 4.48(t, J = 7.3 Hz, 2H), 5.61(d, J = 7.9 Hz, 1H), 5.69-5.81(m, 2H), 7.27(s, 1H), 7.96(d, J = 12.2 Hz, 1H), 8.58(s, 1H), 14.9(s, 1H). |
| 104 | *(structure: quinolone with HOOC, F, Me, OMe, N-heptyl)* | (ESI) 822.5 (MH⁺) | (ESI) $C_{46}H_{65}FN_3O_9$ Calcd., 822.47048 Found, 822.47090 | (in CDCl$_3$): δ 0.75(d, J = 6.7 Hz, 3H), 0.86(t, J = 6.7 Hz, 3H), 0.99(d, J = 6.7 Hz, 3H), 1.13-2.43 (m, 37H), 3.23-3.78(m, 6H), 3.83(s, 3H), 4.48(t, J = 7.3 Hz, 2H), 5.61(d, J = 7.3 Hz, 1H), 5.69-5.82(m, 2H), 7.28(s, 1H), 7.96(d, J = 12.2 Hz, 1H), 8.58(s, 1H), 14.9(s, 1H). |

TABLE 23-continued

| | | | | |
|---|---|---|---|---|
| 105 | [structure: quinolone with HOOC, F, Me, OMe, N-heptyl] | (ESI) 836.5 (MH+) | (ESI) $C_{47}H_{67}FN_3O_9$ Calcd., 836.48613 Found, 836.48643 | (in CDCl$_3$): δ 0.75(d, J = 6.7 Hz, 3H), 0.87(t, J = 6.7 Hz, 3H), 0.99(t, J = 6.7 Hz, 3H), 1.10-2.47 (m, 39H), 3.23-3.61(m, 6H), 3.83(s, 3H), 4.48(t, J = 7.3 Hz, 2H), 5.61(d, J = 7.9 Hz, 1H), 5.69-5.81(m, 2H), 7.28(s, 1H), 7.96(d, J = 12.2 Hz, 1H), 8.58(s, 1H), 14.9(s, 1H). |

TABLE 24

| | | | | |
|---|---|---|---|---|
| 106 | [structure: quinolone with HOOC, F, Me, OMe, N-CH₂CH₂OMe] | (ESI) 782.4 (MH+) | (ESI) $C_{42}H_{57}FN_3O_{10}$ Calcd., 782.40280 Found, 782.40308 | (in CDCl$_3$): δ 0.75(d, J = 7.3 Hz, 3H), 0.99(d, J = 6.7 Hz, 3H), 1.13-2.50 (m, 27H), 3.24(s, 3H), 3.28-3.55(m, 4H), 3.63 (t, J = 4.9 Hz, 1H), 3.83 (s, 3H), 4.71(t, J = 4.9 Hz, 2H), 5.61(d, J = 7.3 Hz, 1H), 5.72-5.80(m, 2H), 7.32(s, 1H), 7.97 (d, J = 12.2 Hz, 1H), 8.60(s, 1H), 14.8(s, 1H). |
| 107 | [structure: quinolone with HOOC, F, Me, OMe, N-(CH₂)₃OMe] | (ESI) 796.4 (MH+) | (ESI) $C_{43}H_{59}FN_3O_{10}$ Calcd., 796.41845 Found, 796.41833 | (in CDCl$_3$): δ 0.75(d, J = 6.7 Hz, 3H), 0.99(d, J = 6.7 Hz, 3H), 1.13-2.43 (m, 29H), 3.20(t, J = 6.1 Hz, 2H), 3.27-3.43(m, 7H), 3.53(br, 2H), 3.84 (s, 3H), 4.64(t, J = 6.7 Hz, 2H), 5.61(d, J = 7.9 Hz, 1H), 5.72-5.80(m, 2H), 7.31(s, 1H), 7.96 (d, J = 12.2 Hz, 1H), 8.63(s, 1H), 14.8(s, 1H). |
| 108 | [structure: quinolone with HOOC, F, Me, OMe, N-CH₂CH₂OCH₂CH₂OMe] | (ESI) 826.4 (MH+) | (ESI) $C_{44}H_{61}FN_3O_{11}$ Calcd., 826.42901 Found, 826.42872 | (in CDCl$_3$): δ 0.75(d, J = 6.7 Hz, 3H), 0.99(d, J = 6.7 Hz, 3H), 1.13-2.43 (m, 27H), 3.25-3.52(m, 13H), 3.77(t, J = 4.9 Hz, 2H), 3.82(s, 3H), 4.73(t, J = 4.9 Hz, 2H), 5.61(d, J = 7.9 Hz, 1H), 5.72-5.82(m, 2H), 7.30(s, 1H), 7.96(d, J = 11.6 Hz, 1H), 8.64(s, 1H), 14.8(s, 1H). |

TABLE 25

| | | | | |
|---|---|---|---|---|
| 109 | [structure: quinolone with HOOC, F, Me, N-propyl] | (ESI) 736.4 (MH+) | (ESI) $C_{41}H_{55}FN_3O_8$ Calcd., 736.39732 Found, 736.39676 | (in CDCl$_3$): δ 0.75(d, J = 6.7 Hz, 3H), 1.00(d, J = 6.7 Hz, 3H), 1.06(t, J = 7.3 Hz, 3H), 1.15-2.41 (m, 30H), 3.13(br, 2H), 3.35(d, J = 6.1 Hz, 1H), 3.49(br, 1H), 3.75-3.81 (m, 2H), 4.23(t, J = 7.3 Hz, 2H), 5.60(d, J = 7.9 Hz, 1H), 5.68-5.79(m, 2H), 7.33(s, 1H), 8.12 (d, J = 12.8 Hz, 1H), 8.67(s, 1H), 14.9(m, 1H). |

TABLE 25-continued

| | | | | |
|---|---|---|---|---|
| 110 | ![structure 110] | (ESI) 778.4(MH+) | (ESI) $C_{44}H_{61}FN_3O_8$ Calcd., 778.44427 Found, 778.44419 | (in CDCl$_3$): δ 0.75(d, J = 7.3 Hz, 3H), 0.91(t, J = 6.7 Hz, 3H), 0.99(d, J = 6.7 Hz, 3H), 1.13-2.42 (m, 35H), 3.03(br, 2H), 3.35(t, J = 6.7 Hz, 1H), 3.46(br, 1H), 3.71-3.78 (m, 2H), 4.23(t, J = 7.3 Hz, 2H), 5.60(d, J = 7.3 Hz, 1H), 5.68-5.79(m, 2H), 6.83(d, J = 6.7 Hz, 1H), 7.35(s, 1H), 8.07 (d, J = 12.8 Hz, 1H), 8.64(s, 1H), 15.1(m, 1H). |
| 111 | ![structure 111] | (ESI) 734.4 (MH+) | (ESI) $C_{41}H_{53}FN_3O_8$ Calcd., 734.38167 Found, 734.38126 | (in CDCl$_3$): δ 0.75(d, J = 6.7 Hz, 3H), 0.98(d, J = 7.3 Hz, 3H), 1.13-2.41 (m, 27H), 2.98-3.03(m, 2H), 3.35(t, J = 7.3 Hz, 1H), 3.44(br, 1H), 3.69-3.76(m, 2H), 4.86(d, J = 4.9 Hz, 2H), 5.26(d, J = 17.1 Hz, 1H), 5.46(d, J = 10.4 Hz, 1H), 5.60(d, J = 7.9 Hz, 1H), 5.69-5.79 (m, 2H), 5.98-6.07(m, 1H), 6.83(d, J = 6.7 Hz, 1H), 7.33(s, 1H), 8.06 (d, J = 13.4 Hz, 1H), 8.67 (s, 1H), 15.1(s, 1H). |

TABLE 26

| | | | | |
|---|---|---|---|---|
| 112 | ![structure 112] | (ESI) 748.4 (MH+) | (ESI) $C_{42}H_{55}FN_3O_8$ Calcd., 748.39732 Found, 748.39761 | (in CDCl$_3$): δ 0.52(q, J = 5.5 Hz, 2H), 0.75(d, J = 6.7 Hz, 3H), 0.81-0.86 (m, 2H), 0.98(d, J = 7.3 Hz, 3H), 1.13-2.42(m, 28H), 3.02-3.07(m, 2H), 3.35(t, J = 7.3 Hz, 1H), 3.45(br, 1H), 3.72-3.79 (m, 2H), 4.08(d, J = 6.7 Hz, 2H), 5.60(d, J = 7.9 Hz, 1H), 5.71-5.79(m, 2H), 6.95(d, J = 6.7 Hz, 1H), 7.31(s, 1H), 8.08 (d, J = 12.8 Hz, 1H), 8.74 (s, 1H), 15.1(s, 1H). |

Reference Example 3

S-Methyl p-toluenethiosulfonate

[Chem. 38]

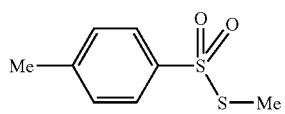

In accordance with the method described in the literature (Synthesis 2002, 343), into a solution (12 mL) of 400 mg (4.25 mmoL) of dimethyl disulfide in methylene chloride were added 2.42 g (13.6 mmoL) of sodium p-toluenesulfinate and 2.16 g (8.50 mmoL) of iodine, followed by stirring at room temperature for 1 hour. The reaction solution was diluted with methylene chloride (12 mL), and a 1 M aqueous sodium thiosulfate solution was added thereto until the iodine color disappeared. The organic layer was washed with water (10 mL), dried over anhydrous magnesium sulfate, and filtered, and the solvent was evaporated. The obtained residue was purified by silica gel column chromatography (hexane:ethyl acetate=10:1) to obtain 1.97 g of the heading compound as a colorless powdery substance (yield 100%).

MS (FAB) (m/z): 203 (MH+).

HRMS (FAB) (m/z): Calcd. for $C_8H_{11}O_2S_2$ (MH+): 203.0200. Found, 203.0177.

Reference Example 4

S-ethyl p-toluenethiosulfonate

[Chem. 39]

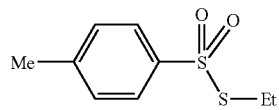

The reaction was carried out using 0.60 mL (4.87 mmoL) of diethyl disulfide, 2.78 g (15.6 mmoL) of sodium p-toluenesulfinate, 2.47 g (9.74 mmoL) of iodine in accordance with the method of Reference Example 3, and the obtained residue was purified by silica gel column chromatography (hexane:ethyl acetate=8:1) to obtain 2.11 g of the heading compound as a colorless oily substance (yield 100%).

MS (EI) (m/z): 216 (M$^+$).

HRMS (EI) (m/z): Calcd. for $C_9H_{12}O_2S_2$ (M$^+$): 216.0279. Found, 216.0238.

Reference Example 5

S-propyl p-toluenethiosulfonate

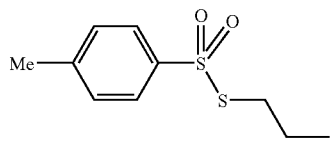

[Chem. 40]

The reaction was carried out using 3.00 g (20.0 mmoL) of dipropyl disulfide, 11.4 g (64.0 mmoL) of sodium p-toluenesulfinate, and 10.2 g (40.0 mmoL) of iodine in accordance with the method of Reference Example 3, and the obtained residue was purified by silica gel column chromatography (hexane:ethyl acetate=20:1) to obtain 9.20 g of the heading compound as a yellow oily substance (yield 100%).

MS (EI) (m/z): 230 (M$^+$).

HRMS (EI) (m/z): Calcd. for $C_{10}H_{14}O_2S_2$ (M$^+$): 230.0435. Found, 230.0449.

Reference Example 6

S-butyl p-toluenethiosulfonate

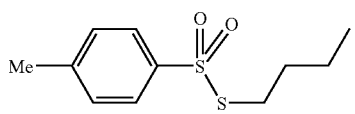

[Chem. 41]

The reaction was carried out using 3.00 g (16.8 mmoL) of dibutyl disulfide, 9.59 g (53.8 mmoL) of sodium p-toluenesulfinate, and 8.53 g (33.6 mmoL) of iodine in accordance with the method of Reference Example 3, the obtained residue was purified by silica gel column chromatography (hexane:ethyl acetate=20:1) to obtain 8.21 g of the heading compound as a yellow oily substance (yield 100%).

MS (EI) (m/z): 244 (M$^+$).

HRMS (EI) (m/z): Calcd. for $C_{11}H_{16}O_2S_2$ (M$^+$): 244.0592. Found, 244.0595.

Reference Example 7

S-Pentane p-toluenethiosulfonate

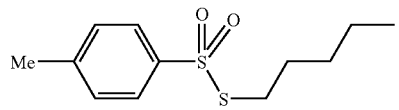

[Chem. 42]

The reaction was carried out using 3.00 g (14.5 mmoL) of dipentyl disulfide, 8.27 g (46.4 mmoL) of sodium p-toluenesulfinate, and 7.36 g (29.0 mmoL) of iodine in accordance with the method of Reference Example 3, and the obtained residue was purified by silica gel column chromatography (hexane:ethyl acetate=20:1) to obtain 7.36 g of the heading compound as a pale yellow oily substance (yield 98%).

MS (EI) (m/z): 258 (M$^+$).

HRMS (EI) (m/z): Calcd. for $C_{12}H_{18}O_2S_2$ (M$^+$): 258.0748. Found, 258.0755.

Reference Example 8

S-(2-Fluoro)ethane p-toluenethiosulfonate

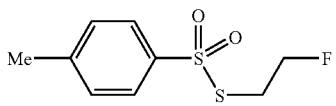

[Chem. 43]

To a solution of 3.00 g (19.4 mmoL) of 2,2-dithioethanol in toluene was added 17.3 mL (116 mmoL) of 1,8-diazabicyclo[5.4.0]unde-7-cene with ice-cooling under an argon atmosphere, and then 16.0 mL (58.2 mmoL) of perfluorooctane sulfonylfluoride was added dropwise, followed by stirring for 40 hours while naturally warming. To the reaction mixture was added a diluted aqueous citric acid solution, followed by extraction with ethyl acetate (50 mL×3). The combined organic layer was washed with saturated brine (50 mL), filtered, then dried over anhydrous magnesium sulfate, and the solvent was evaporated. The obtained residue was reacted using 11.1 g (62.1 mmoL) of sodium p-toluenesulfinate and 9.85 g (38.8 mmoL) of iodine in accordance with the method of Reference Example 6, and the obtained residue was purified by silica gel column chromatography (hexane:ethyl acetate=20:1) to obtain 877 mg of the heading compound as a yellow oily substance (yield 10%).

$^1$H NMR (400 MHz, CDCl$_3$) δ 2.47 (s, 3H), 3.26 (t, J=6.1 Hz, 1H), 3.31 (t, J=6.1 Hz, 1H), 4.51 (t, J=6.4 Hz, 1H), 4.62 (t, J=6.4 Hz, 1H), 7.36 (d, J=7.9 Hz, 2H), 7.82 (d, J=7.9 Hz, 2H).

IR (neat): 1330, 1140 (cm$^{-1}$).

MS (EI) (m/z): 234 (M$^+$).

HRMS (EI) (m/z): Calcd. for $C_9H_{11}FO_2S_2$ (M$^+$): 234.0185. Found, 234.0186.

Reference Example 9

S-(2-t-Butyldimethylsilyloxy)ethane p-toluenethiosulfonate

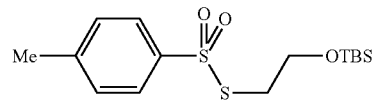

[Chem. 44]

To a solution of 3.00 g (19.4 mmoL) of 2,2-dithioethanol in methylene chloride were added 7.02 g (46.6 mmoL) of t-butyldimethylsilyl chloride and 13.5 mL (116 mmoL) of 2,6-lutidine with ice-cooling under an argon atmosphere. After stirring for 40 hours while naturally warming, 4.68 g (31.0 mmoL) of t-butyldimethylsilyl chloride and 9.04 mL (77.6 mmoL) of 2,6-lutidine were added thereto, followed by stirring for 6 hours. To the reaction mixture was added 4.88 mL (38.8 mmoL) of 3-(dimethylamino)propylamine, followed by stirring for 0.5 hour, and a diluted aqueous citric acid solution was added thereto, followed by concentration. The residue was extracted with ethyl acetate (100 mL×3), the combined organic layer was washed with saturated brine (100 mL), dried over anhydrous magnesium sulfate, and filtered, and the solvent was evaporated. The obtained residue was reacted using 11.1 g (62.1 mmoL) of sodium p-toluenesulfinate and 9.85 g (38.8 mmoL) of iodine in accordance with the method of Reference Example 6, and the obtained residue was purified by silica gel column chromatography (hexane:ethyl acetate=20:1) to obtain 12.9 g of the heading compound as a colorless oily substance (yield 96%).

$^1$H NMR (400 MHz, CDCl$_3$) δ 0.01 (s, 6H), 0.85 (s, 9H), 2.45 (s, 3H), 3.12 (t, J=6.1 Hz, 2H), 3.77 (t, J=6.1 Hz, 2H), 7.34 (d, J=7.9 Hz, 2H), 7.82 (d, J=7.9 Hz, 2H).

IR (neat): 1330, 1140 (cm$^{-1}$).

MS (CI) (m/z): 347 (MH$^+$).

HRMS (CI) (m/z): Calcd. for C$_{15}$H$_{27}$O$_3$S$_2$Si (MH$^+$): 347.1171. Found, 347.1148.

Reference Example 10

S-(2-propene) p-toluenethiosulfonate

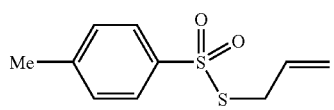

[Chem. 45]

The reaction was carried out using 3.00 g (20.5 mmoL) of allyl disulfide, 11.7 g (65.6 mmoL) of sodium p-toluenesulfinate, and 10.4 g (41.0 mmoL) of iodine in accordance with the method of Reference Example 3, and the obtained residue was purified by silica gel column chromatography (hexane:ethyl acetate=20:1) to obtain 7.03 g of the heading compound as a black oily substance (yield 75%).

MS (CI) (m/z): 229 (MH$^+$).

HRMS (CI) (m/z): Calcd. for C$_{10}$H$_{13}$O$_2$S$_2$ (MH$^+$): 229.0357. Found, 229.0359.

Reference Example 11

S-(1-Methyl)ethane p-toluenethiosulfonate

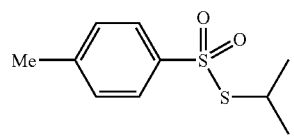

[Chem. 46]

The reaction was carried out using 3.00 g (20.0 mmoL) of diisopropyl disulfide, 11.4 g (64.0 mmoL) of sodium p-toluenesulfinate, and 10.2 g (40.0 mmoL) of iodine in accordance with the method of Reference Example 3, and the obtained residue was purified by silica gel column chromatography (hexane:ethyl acetate=20:1 and then 10:1) to obtain 4.29 g of the heading compound as a yellow oily substance (yield 47%).

MS (EI) (m/z): 230 (M$^+$).

HRMS (EI) (m/z): Calcd. for C$_{10}$H$_{14}$O$_2$S$_2$ (M$^+$): 230.0435. Found, 230.0458.

Reference Example 12

S-benzene p-toluenethiosulfonate

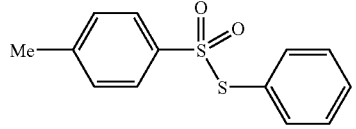

[Chem. 47]

The reaction was carried out using 3.00 g (13.7 mmoL) of diphenyl disulfide, 7.80 g (43.8 mmoL) of sodium p-toluenesulfinate, and 6.95 g (27.4 mmoL) of iodine in accordance with the method of Reference Example 3, and the obtained residue was purified by silica gel column chromatography (hexane:ethyl acetate=10:1) to obtain 6.20 g of the heading compound as a colorless powdery substance (yield 86%).

MS (EI) (m/z): 264 (M$^+$).

HRMS (EI) (m/z): Calcd. for C$_{13}$H$_{12}$O$_2$S$_2$ (M$^+$): 264.0279. Found, 264.0245.

Reference Example 13

S-(4-Chloro)benzene p-toluenethiosulfonate

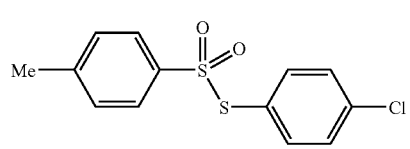

[Chem. 48]

The reaction was carried out using 4.00 g (13.9 mmoL) of 4-chlorophenyl disulfide, 7.93 g (44.5 mmoL) of sodium p-toluenesulfinate, and 7.06 g (27.8 mmoL) of iodine in accordance with the method of Reference Example 3, and the obtained residue was purified by silica gel column chromatography (hexane:ethyl acetate=30:1 and then 10:1) to obtain 3.86 g of the heading compound as a colorless powdery substance (yield 45%).

MS (EI) (m/z): 298 (M$^+$).

HRMS (EI) (m/z): Calcd. for C$_{13}$H$_{11}$ClO$_2$S$_2$ (M$^+$): 297.9889. Found, 297.9909.

Reference Example 14

S-(2-pyridine) p-toluenethiosulfonate

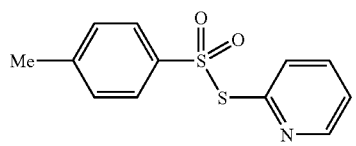

[Chem. 49]

The reaction was carried out using 4.00 g (18.2 mmoL) of 2,2-dipyridyldisulfide, 10.4 g (58.2 mmoL) of sodium p-toluenesulfinate, and 9.24 g (36.4 mmoL) of iodine in accordance with the method of Reference Example 3, and the obtained residue was purified by silica gel column chromatography (hexane:ethyl acetate=10:1 and then 4:1) to obtain 2.12 g of the heading compound as a yellow oily substance (yield 44%).

MS (CI) (m/z): 266 (MH$^+$).

HRMS (CI) (m/z): Calcd. for $C_{12}H_{12}NO_2S_2$ (MH$^+$): 266.0309. Found, 266.0279.

Reference Example 15

First Step (3R)-3-Deoxo-11-deoxy-12-desethenyl-12-hydroxyl-3-methoxy-14-methoxymethoxy-11-oxo-4-epimutilin

[Chem. 50]

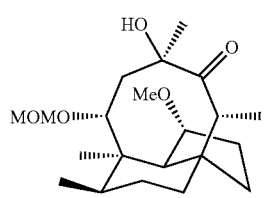

To a solution (60 mL) of 1.00 g (2.84 mmoL) of (3R)-3-deoxo-11-deoxy-12-desethenyl-3-methoxy-14-methoxymethoxy-11-oxo-4-epimutilin described in Patent Document 19 in anhydrous tetrahydrofuran was added 6.81 mL (3.40 mmoL) of potassium bis(trimethylsilyl)amide (0.5 mol/L toluene solution) at −70° C. under an argon atmosphere, followed by stirring for 0.5 hour. Under the same condition, 0.78 g (3.40 mmoL) of (1R)-(−)-(10-camphorsulfonyl) oxaziridine was added thereto, followed by stirring for 2.5 hours while warming to −50° C. To the mixed reaction liquid was added a diluted aqueous citric acid solution, followed by evaporation under reduced pressure, and the obtained residue was extracted with ethyl acetate (30 mL×3). The combined organic layer was washed with saturated brine (30 mL), dried over anhydrous magnesium sulfate, and filtered, and the solvent was evaporated. The obtained residue was purified by silica gel column chromatography (hexane:ethyl acetate=4:1) to obtain 777 mg of the heading compound as a colorless crystal (yield 74%).

MS (FAB) (m/z): 307 (MH$^+$—HOCH$_2$CH$_3$).

HRMS (FAB) (m/z): Calcd. for $C_{19}H_{31}O_3$ (MH$^+$—HOCH$_2$CH$_3$): 307.2273. Found, 307.2270.

Second Step (3R)-3-Deoxo-11-deoxy-12-desethenyl-3-methoxy-14-methoxymethoxy-11-oxo-12-(2-propynyloxy)-4-epimutilin

[Chem. 51]

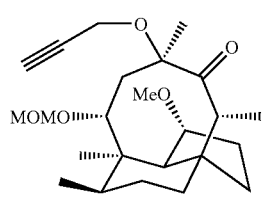

To a solution (10 mL) of 500 mg (1.36 mmoL) of the compound of First Step in N,N-dimethylformamide was added 109 mg (2.71 mmoL) of sodium hydride (60% oily substance) at room temperature, followed by stirring at room temperature for 0.5 hour. Under the same condition under an argon atmosphere, 204 µL (2.71 mmoL) of propargyl bromide was added thereto, followed by stirring for 2 hours. To the reaction mixture was added a diluted aqueous citric acid solution, followed by extraction with ethyl acetate (10 mL×3), the combined organic layer was washed with saturated brine (10 mL), dried over anhydrous magnesium sulfate, and filtered, and the solvent was evaporated. The obtained residue was purified by silica gel column chromatography (hexane:ethyl acetate=4:1) to obtain 527 mg of the heading compound as a yellow oily substance (yield 96%).

MS (FAB) (m/z): 345 (MH$^+$—HOCH$_2$OCH$_3$).

HRMS (FAB) (m/z): Calcd. for $C_{22}H_{33}O_3$ (MH$^+$—HOCH$_2$OCH$_3$): 345.2430. Found, 345.2387.

Third Step (3R)-3-Deoxo-11-deoxy-12-desethenyl-3-methoxy-11-oxo-12-(2-propynyloxy)-4-epimutilin

[Chem. 52]

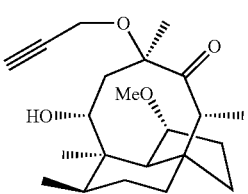

To a solution (10 mL) of 527 mg (1.30 mmoL) of the compound of Second Step in methanol was added 247 mg (1.30 mmoL) of p-toluene sulfonic acid, followed by stirring at room temperature for 48 hours. The reaction mixture was evaporated under reduced pressure, and to the residue was added water, followed by extraction with ethyl acetate (10 mL×3). The combined organic layer was washed with saturated brine (10 mL), dried over anhydrous magnesium sulfate, and filtered, and the solvent was evaporated. The obtained residue was purified by silica gel column chromatography (hexane:ethyl acetate=2:1) to obtain 331 mg of the heading compound as a yellow powder (yield 70%).

MS (CI) (m/z): 363 (MH$^+$).

HRMS (CI) (m/z): Calcd. for $C_{22}H_{35}O_4$ (MH$^+$): 363.2535. Found, 363.2511.

Reference Example 16

First Step (3R)-3-Deoxo-11-deoxy-12-desethenyl-3,12-dimethoxy-14-methoxymethoxy-11-oxo-4-epimutilin

[Chem. 53]

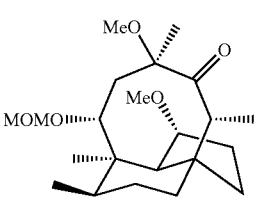

The reaction was carried out using 518 mg (1.41 mmoL) of the compound of First Step of Reference Example 15, 112 mg (2.81 mmoL) of sodium hydride (60% oily substance), and 175 µL (2.81 mmoL) of methyl iodide in accordance with the method of Second Step of Reference Example 15, and the obtained residue was purified by silica gel column chromatography (hexane:ethyl acetate=4:1) to obtain 537 mg of the heading compound as a colorless oily substance (yield 100%).

MS (FAB) (m/z): 321 (MH⁺–HOCH$_2$OCH$_3$).

HRMS (FAB) (m/z): Calcd. for C$_{20}$H$_{33}$O$_3$ (MH⁺—HOCH$_2$OCH$_3$): 321.2430. Found, 321.2394.

Second Step (3R)-3-Deoxo-11-deoxy-12-desethenyl-3,12-dimethoxy-11-oxo-4-epimutilin

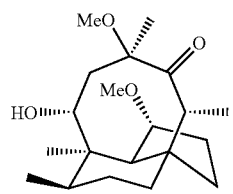

[Chem. 54]

The reaction was carried out using 239 mg (0.62 mmoL) of the compound of First Step and 119 mg (0.62 mmoL) of p-toluene sulfonic acid in accordance with the method of Third Step of Reference Example 15, and the obtained residue was purified by silica gel column chromatography (hexane:ethyl acetate=2:1) to obtain 174 mg of the heading compound as a colorless powdery substance (yield 82%).

MS (FAB) (m/z): 339 (MH⁺).

HRMS (FAB) (m/z): Calcd. for C$_{20}$H$_{35}$O$_4$ (MH⁺): 339.2535. Found, 339.2508.

Reference Example 16

First Step (3R)-3-Deoxo-11-deoxy-12-desethenyl-3-methoxy-14-methoxymethoxy-11-oxo-12-(2-propenyl) oxy-4-epimutilin

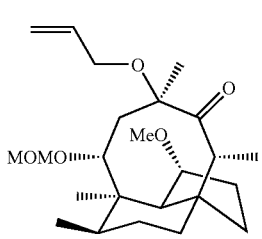

[Chem. 55]

The reaction was carried out using 500 mg (1.36 mmoL) of the compound of First Step of Reference Example 15, 109 mg (2.71 mmoL) of sodium hydride (60% oily substance), and 235 μl, (2.71 mmoL) of aryl bromide in accordance with the method of Second Step of Reference Example 15, and the obtained residue was purified by silica gel column chromatography (hexane:ethyl acetate=4:1) to obtain 554 mg of the yellow oily heading compound (yield 100%).

MS (FAB) (m/z): 347 (MH⁺—HOCH$_2$OCH$_3$).

HRMS (FAB) (m/z): Calcd. for C$_{22}$H$_{35}$O$_3$ (MH⁺—HOCH$_2$OCH$_3$): 347.2586. Found, 347.2623.

Second Step (3R)-3-Deoxo-11-deoxy-12-desethenyl-3-methoxy-11-oxo-12-(2-propenyl) oxy-4-epimutilin

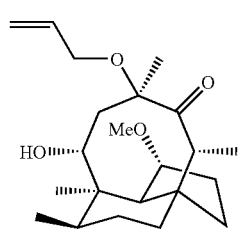

[Chem. 56]

The reaction was carried out using 554 mg (1.36 mmoL) of the compound of First Step and 258 mg (1.36 mmoL) of p-toluene sulfonic acid in accordance with the method of Third Step of Reference Example 15, and the obtained residue was purified by silica gel column chromatography (hexane:ethyl acetate=2:1) to obtain 338 mg of the heading compound as a colorless powdery substance (yield 68%).

MS (FAB) (m/z): 365 (MH⁺).

HRMS (FAB) (m/z): Calcd. for C$_{22}$H$_{37}$O$_4$ (MH⁺): 365.2692. Found, 365.2670.

Reference Example 17

First Step (3R)-3-Deoxo-1-deoxy-12-desethenyl-12-ethoxy-3-methoxy-14-methoxymethoxy-11-oxo-4-epimutilin

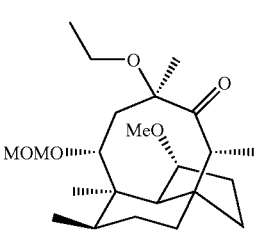

[Chem. 57]

The reaction was carried out using 500 mg (1.36 mmoL) of the compound of First Step of Reference Example 15, 109 mg (2.71 mmoL) of sodium hydride (60% oily substance), and 217 μL (2.71 mmoL) of iodoethane in accordance with the method of Second Step of Reference Example 15, and the obtained residue was purified by silica gel column chromatography (hexane:ethyl acetate=4:1) to obtain 537 mg of the colorless oily heading compound (yield 100%).

MS (FAB) (m/z): 335 (MH⁺—HOCH$_2$OCH$_3$).

HRMS (FAB) (m/z): Calcd. for C$_{21}$H$_{35}$O$_3$ (MH⁺—HOCH$_2$OCH$_3$): 335.2586. Found, 335.2552.

Second Step (3R)-3-Deoxo-11-deoxy-12-desethenyl-12-ethoxy-3-methoxy-11-oxo-4-epimutilin

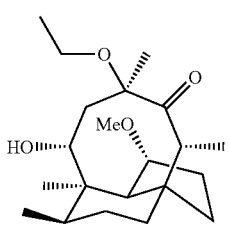

[Chem. 58]

The reaction was carried out using 537 mg (1.36 mmoL) of the compound of First Step and 258 mg (1.36 mmoL) of p-toluene sulfonic acid in accordance with the method of Third Step of Reference Example 15, and the obtained residue was purified by silica gel column chromatography (hexane:ethyl acetate=2:1) to obtain 118 mg of the heading compound as a colorless oily substance (yield 25%).

MS (FAB) (m/z): 353 (MH$^+$).

HRMS (FAB) (m/z): Calcd. for $C_{21}H_{37}O_4$ (MH$^+$): 353.2692. Found, 353.2667.

Reference Example 18

First Step (3R)-3-Deoxo-11-deoxy-12-desethenyl-12-(2-fluoroethoxy)-3-methoxy-14-methoxymethoxy-11-oxo-4-epimutilin

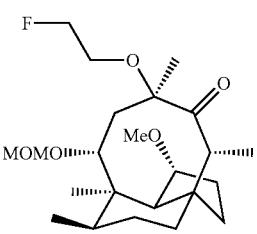

[Chem 59]

The reaction was carried out using 500 mg (1.36 mmoL) of the compound of First Step of Reference Example 15, 109 mg (2.71 mmoL) of sodium hydride (60% oily substance), and 345 mg (2.71 mmoL) of 1-bromo-2-fluoroethane in accordance with the method of Second Step of Reference Example 15, and the obtained residue was purified by silica gel column chromatography (hexane:ethyl acetate=8:1 and then hexane:ethyl acetate=1:1) to obtain 86.4 mg of the colorless oily heading compound (yield 15%).

MS (FAB) (m/z): 353 (MH$^+$—HOCH$_2$OCH$_3$).

HRMS (FAB) (m/z): Calcd. for $C_{21}H_{34}FO_3$ (MH$^+$—HOCH$_2$OCH$_3$): 353.2492. Found, 353.2494.

Second Step (3R)-3-Deoxo-11-deoxy-12-desethenyl-12-(2-fluoroethoxy)-3-methoxy-11-oxo-4-epimutilin

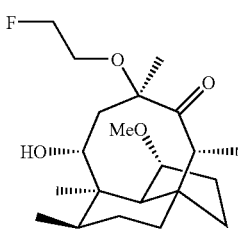

[Chem. 60]

The reaction was carried out using 86.4 mg (0.21 mmoL) of the compound of First Step and 39.6 mg (0.21 mmoL) of p-toluene sulfonic acid in accordance with the method of Third Step of Reference Example 15, and the obtained residue was purified by silica gel column chromatography (hexane:ethyl acetate=2:1) to obtain 52.8 mg of the heading compound as a colorless powdery substance (yield 68%).

MS (FAB) (m/z): 353 (MH$^+$—H$_2$O).

HRMS (FAB) (m/z): Calcd. for $C_{21}H_{34}FO_3$ (MH$^+$—H$_2$O): 353.2492. Found, 353.2517.

Reference Example 19

First Step (3R)-3-Deoxo-11-deoxy-12-desethenyl-12-(2,2-difluoroethoxy)-3-methoxy-14-methoxymethoxy-11-oxo-4-epimutilin

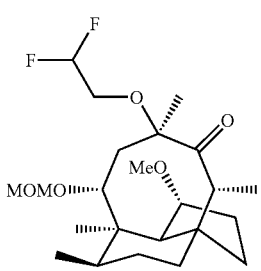

[Chem. 61]

The reaction was carried out using 500 mg (1.36 mmoL) of the compound of First Step of Reference Example 15, 163 mg (4.07 mmoL) of sodium hydride (60% oily substance), and 481 mg (2.04 mmoL) of difluoroethanol p-toluenesulfonate prepared from difluoroethanol and p-toluene sulfonyl chloride in accordance with the method of Second Step of Reference Example 15, and the obtained residue was purified by silica gel column chromatography (hexane:ethyl acetate=4:1) to obtain 557 mg of the colorless oily heading compound (yield 95%).

MS (FAB) (m/z): 371 (MH$^+$—HOCH$_2$OCH$_3$).

HRMS (FAB) (m/z): Calcd. for $C_{21}H_{33}F_2O_3$ (MH$^+$—HOCH$_2$OCH$_3$): 371.2398. Found, 371.2364.

Second Step (3R)-3-Deoxo-11-deoxy-12-desethenyl-12-(2,2-difluoroethoxy)-3-methoxy-11-oxo-4-epimutilin

[Chem 62]

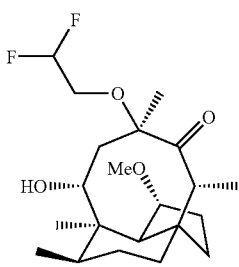

The reaction was carried out using 557 mg (1.29 mmoL) of the compound of First Step and 245 mg (1.29 mmoL) of p-toluene sulfonic acid in accordance with the method of Third Step of Reference Example 15, and the obtained residue was purified by silica gel column chromatography (hexane:ethyl acetate=2:1) to obtain 246 mg of the heading compound as a colorless powdery substance (yield 49%).

MS (FAB) (m/z): 389 (MH$^+$).

HRMS (FAB) (m/z): Calcd. for $C_{21}H_{35}F_2O_4$ (MH$^+$): 389.2503. Found, 389.2466.

Reference Example 20

First Step (3R)-3-Deoxo-11-deoxy-12-desethenyl-12-ethylthio-3-methoxy-14-methoxymethoxy-11-oxo-4-epimutilin

[Chem. 63]

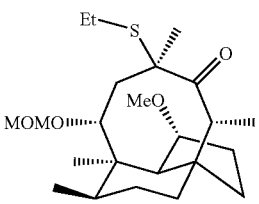

The reaction was carried out using 1.00 g (2.84 mmoL) of (3R)-3-deoxo-11-deoxy-12-desethenyl-3-methoxy-14-methoxymethoxy-11-oxo-4-epimutilin described in Patent Document 19, 738 mg (3.41 mmoL) of the compound of Reference Example 4, and 6.82 mL (3.41 mmoL) of potassium bis(trimethylsilyl)amide (0.5 mol/L toluene solution) in accordance with the method of Second Step of Example 2, and the obtained residue was purified by silica gel column chromatography (hexane:ethyl acetate=6:1) to obtain 772 mg of the heading compound as a colorless oily substance (yield 60%).

MS (FAB) (m/z): 413 (MH$^+$).

HRMS (FAB) (m/z): Calcd. for $C_{23}H_{41}O_4S$ (MH$^+$): 413.2726. Found, 413.2753.

Second Step (3R)-3-Deoxo-11-deoxy-12-desethenyl-12-ethylthio-3-methoxy-11-oxo-4-epimutilin

[Chem. 64]

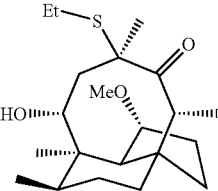

The reaction was carried out using 691 mg (1.67 mmoL) of the compound of First Step and 318 mg (1.67 mmoL) of p-toluene sulfonic acid in accordance with the method of Second Step of Example 2, and the obtained residue was purified by silica gel column chromatography (hexane:ethyl acetate=6:1) to obtain 510 mg of the heading compound as a yellow oily substance (yield 83%).

MS (FAB) (m/z): 369 (MH$^+$).

HRMS (FAB) (m/z): Calcd. for $C_{21}H_{37}O_3S$ (MH$^+$): 369.2463. Found, 369.2438.

Reference Example 21

First Step (3R)-3-Deoxo-11-deoxy-12-desethenyl-3-methoxy-14-methoxymethoxy-12-methyl sulfonyl-11-oxo-4-epimutilin

[Chem. 65]

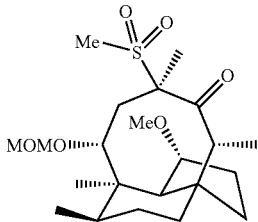

To a solution (15 mL) of 500 mg (1.25 mmoL) of the compound of First Step of Example 2 in methylene chloride was added 996 mg (3.75 mmoL) of m-chloroperbenzoic acid under ice-cooling, followed by stirring for 0.5 hour while warming to room temperature. The reaction mixture was filtered over Celite, and the residue was washed with methylene chloride. The combined organic layer was evaporated under reduced pressure, and to the residue was added ethyl acetate (15 mL), followed by washing with a 10% aqueous sodium hydrogen sulfite solution (15 mL) and a saturated aqueous sodium hydrogen carbonate solution (15 mL×3). The organic layer was washed with saturated brine (15 mL), dried over anhydrous magnesium sulfate, and filtered, and the solvent was evaporated. The obtained residue was purified by silica gel column chromatography (hexane:ethyl acetate=2:1) to obtain 478 mg of the heading compound as a colorless powdery substance (yield 89%).

MS (FAB) (m/z): 431 (MH$^+$).

HRMS (FAB) (m/z): Calcd. for $C_{22}H_{39}O_6S$ (MH$^+$): 431.2467. Found, 431.2450.

Second Step (3R)-3-Deoxo-11-deoxy-12-desethenyl-3-methoxy-12-methyl sulfonyl-11-oxo-4-epimutilin

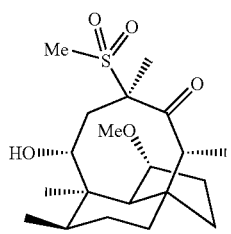

[Chem. 66]

The reaction was carried out using 400 mg (0.93 mmoL) of the compound of First Step and 177 mg (0.93 mmoL) of p-toluene sulfonic acid in accordance with the method of Second Step of Example 2, and the obtained residue was purified by silica gel column chromatography (hexane:ethyl acetate=2:1) to obtain 349 mg of the heading compound as a colorless powdery substance (yield 97%).

MS (FAB) (m/z): 369 (MH$^+$—H$_2$O).

HRMS (FAB) (m/z): Calcd. for C$_{20}$H$_{33}$O$_4$S (MH$^+$—H$_2$O): 369.2160. Found, 369.2136.

Reference Example 22

First Step (3R)-3-Deoxo-11-deoxy-12-desethenyl-3-methoxy-14-methoxymethoxy-11-oxo-12-propylthio-4-epimutilin

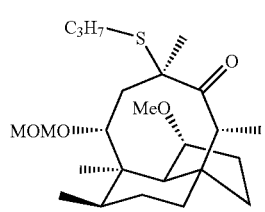

[Chem. 67]

The reaction was carried out using 3.00 g (8.51 mmoL) of (3R)-3-deoxo-11-deoxy-12-desethenyl-3-methoxy-14-methoxymethoxy-11-oxo-4-epimutilin described in Patent Document 19, 2.35 g (10.2 mmoL) of the compound of Reference Example 5, and 20.4 mL (10.2 mmoL) of potassium bis(trimethylsilyl)amide (0.5 mol/L toluene solution) in accordance with the method of First Step of Example 2, and the obtained residue was purified by silica gel column chromatography (hexane:ethyl acetate=10:1) to obtain 3.59 g of the yellow oily heading compound (yield 99%).

MS (CI) (m/z): 427 (MH$^+$).

HRMS (CI) (m/z): Calcd. for C$_{24}$H$_{43}$O$_4$S (MH$^+$): 427.2882. Found, 427.2903.

Second Step (3R)-3-Deoxo-11-deoxy-12-desethenyl-3-methoxy-11-oxo-12-propylthio-4-epimutilin

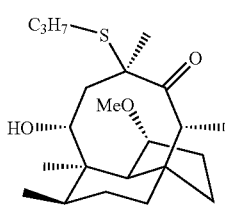

[Chem. 68]

The reaction was carried out using 3.00 g (7.03 mmoL) of the compound of First Step and 1.34 g (7.03 mmoL) of p-toluene sulfonic acid in accordance with the method of Second Step of Example 2, and the obtained residue was purified by silica gel column chromatography (hexane:ethyl acetate=10:1) to obtain 2.38 g of the heading compound as a colorless oily substance (yield 88%).

MS (FAB) (m/z): 383 (MH$^+$).

HRMS (FAB) (m/z): Calcd. for C$_{22}$H$_{39}$O$_3$S (MH$^+$): 383.2620. Found, 383.2655.

Reference Example 23

First Step (3R)-3-Butylthio-3-deoxo-11-deoxy-12-desethenyl-3-methoxy-14-methoxymethoxy-11-oxo-4-epimutilin

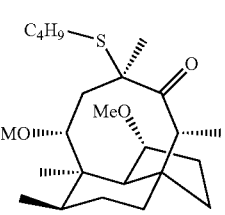

[Chem. 69]

The reaction was carried out using 3.00 g (8.51 mmoL) of (3R)-3-deoxo-11-deoxy-12-desethenyl-3-methoxy-14-methoxymethoxy-11-oxo-4-epimutilin described in Patent Document 19, 2.49 g (10.2 mmoL) of the compound of Reference Example 6, and 20.4 mL (10.2 mmoL) of potassium bis(trimethylsilyl)amide (0.5 mol/L toluene solution) in accordance with the method of First Step of Example 2, and the obtained residue was purified by silica gel column chromatography (hexane:ethyl acetate=50:1) to obtain 3.14 g of the heading compound as a colorless powdery substance (yield 84%).

MS (FAB) (m/z): 441 (MH$^+$).

HRMS (FAB) (m/z): Calcd. for C$_{25}$H$_{45}$O$_4$S (MH$^+$): 441.3039. Found, 441.3022.

Second Step (3R)-12-Butylthio-3-deoxo-11-deoxy-12-desethenyl-3-methoxy-11-oxo-4-epimutilin

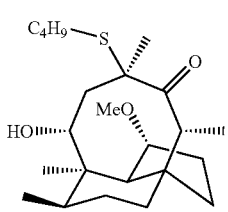

[Chem. 70]

The reaction was carried out using 3.00 g (6.81 mmoL) of the compound of First Step and 1.30 g (6.81 mmoL) of p-toluene sulfonic acid in accordance with the method of Second Step of Example 2, and the obtained residue was purified by silica gel column chromatography (hexane:ethyl acetate=10:1) to obtain 2.71 g of the heading compound as a colorless oily substance (yield 100%).

MS (FAB) (m/z): 397 (MH$^+$).

HRMS (FAB) (m/z): Calcd. for $C_{23}H_{41}O_3S$ (MH$^+$): 397.2776. Found, 397.2791.

Reference Example 24

First Step (3R)-3-Deoxo-11-deoxy-12-desethenyl-3-methoxy-14-methoxymethoxy-11-oxo-12-pentylthio-4-epimutilin

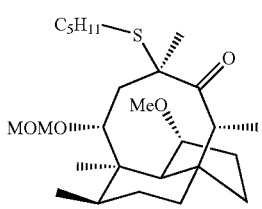

[Chem. 71]

The reaction was carried out using 3.00 g (8.51 mmoL) of (3R)-3-deoxo-11-deoxy-12-desethenyl-3-methoxy-14-methoxymethoxy-11-oxo-4-epimutilin described in Patent Document 19, 2.64 g (10.2 mmoL) of the compound of Reference Example 7, and 20.4 mL (10.2 mmoL) of potassium bis(trimethylsilyl)amide (0.5 mol/L toluene solution) in accordance with the method of First Step of Example 2, and the obtained residue was purified by silica gel column chromatography (hexane:ethyl acetate=50:1) to obtain 3.14 g of the colorless oily heading compound (yield 81%).

MS (FAB) (m/z): 455 (MH$^+$).

HRMS (FAB) (m/z): Calcd. for $C_{26}H_{47}O_4S$ (MH$^+$): 455.3195. Found, 455.3224.

Second Step (3R)-3-Deoxo-11-deoxy-12-desethenyl-3-methoxy-11-oxo-12-pentylthio-4-epimutilin

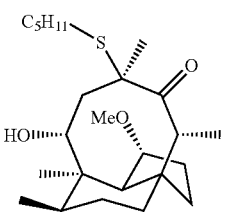

[Chem 72]

The reaction was carried out using 3.00 g (6.60 mmoL) of the compound of First Step and 1.26 g (6.60 mmoL) of p-toluene sulfonic acid in accordance with the method of Second Step of Example 2, and the obtained residue was purified by silica gel column chromatography (hexane:ethyl acetate=10:1) to obtain 2.61 g of the heading compound as a colorless oily substance (yield 96%).

MS (FAB) (m/z): 411 (MH$^+$).

HRMS (FAB) (m/z): Calcd. for $C_{24}H_{43}O_3S$ (MH$^+$): 411.2933 Found, 411.2927.

Reference Example 25

First Step (3R)-3-Deoxo-11-deoxy-12-desethenyl-12-(2-fluoroethyl)thio-3-methoxy-14-methoxymethoxy-11-oxo-4-epimutilin

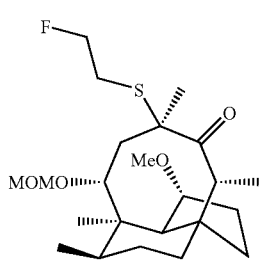

[Chem. 73]

The reaction was carried out using 1.00 g (2.84 mmoL) of (3R)-3-deoxo-11-deoxy-12-desethenyl-3-methoxy-14-methoxymethoxy-11-oxo-4-epimutilin described in Patent Document 19, 800 mg (3.41 mmoL) of the compound of Reference Example 8, and 6.82 mL (3.41 mmoL) of potassium bis(trimethylsilyl)amide (0.5 mol/L toluene solution) in accordance with the method of First Step of Example 2, and the obtained residue was purified by silica gel column chromatography (hexane:ethyl acetate=10:1) to obtain 1.14 g of the heading compound as a yellow oily substance (yield 93%).

MS (FAB) (m/z): 431 (MH$^+$).

HRMS (FAB) (m/z): Calcd. for $C_{23}H_{40}FO_4S$ (MH$^+$): 431.2631. Found, 431.2666.

Second Step (3R)-3-Deoxo-11-deoxy 2-desethenyl-12-(2-fluoro-ethyl)thio-3-methoxy-11-oxo-4-epimutilin

[Chem. 74]

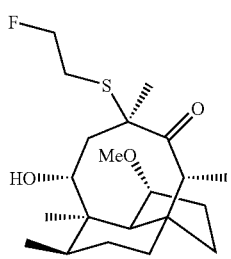

The reaction was carried out using 1.00 g (2.32 mmoL) of the compound of First Step and 662 mg (3.48 mmoL) of p-toluene sulfonic acid in accordance with the method of Third Step of Example 2, and the obtained residue was purified by silica gel column chromatography (hexane:ethyl acetate=10:1) to obtain 652 mg of the heading compound as a colorless powdery substance (yield 73%).

MS (FAB) (m/z): 387 (MH$^+$).

HRMS (FAB) (m/z): Calcd. for $C_{21}H_{36}FO_3S$ (MH$^+$): 387.2369. Found, 387.2367.

Reference Example 26

First Step (3R)-12-(2-t-Butyldimethylsilyloxyethyl)thio-3-deoxo-11-deoxy-12-desethenyl-3-methoxy-14-methoxymethoxy-11-oxo-4-epimutilin

[Chem. 75]

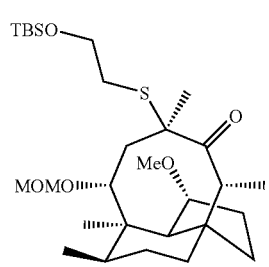

The reaction was carried out using 1.00 g (2.84 mmoL) of (3R)-3-deoxo-11-deoxy-12-desethenyl-3-methoxy-14-methoxymethoxy-11-oxo-4-epimutilin described in Patent Document 19, 1.18 g (3.41 mmoL) of the compound of Reference Example 9, and 6.82 mL (3.41 mmoL) of potassium bis(trimethylsilyl)amide (0.5 mol/L toluene solution) in accordance with the method of First Step of Example 2, and the obtained residue was purified by silica gel column chromatography (hexane:ethyl acetate=10:1) to obtain 1.33 g of the heading compound as a colorless oily substance (yield 79%).

MS (FAB) (m/z): 481.5 (MH$^+$—HOCH$_2$OCH$_3$).

HRMS (FAB) (m/z): Calcd. for $C_{27}H_{49}O_3SSi$ (MH$^+$—HOCH$_2$OCH$_3$): 481.3172. Found, 481.3191.

Second Step (3R)-12-(2-t-Butyldimethylsilyloxyethyl)thio-3-deoxo-11-deoxy-12-desethenyl-3-methoxy-11-oxo-4-epimutilin

[Chem. 76]

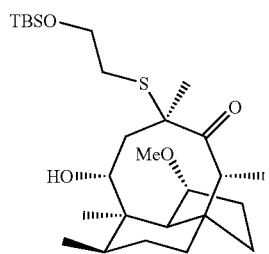

The reaction was carried out using 1.10 g (2.03 mmoL) of the compound of First Step and 580 mg (3.05 mmoL) of p-toluene sulfonic acid in accordance with the method of Second Step of Example 2. The obtained residue was dissolved in methylene chloride, and 247 mg (1.82 mmoL) of t-butyldimethylsilyl chloride and 0.21 mL (1.82 mmoL) of 2,6-lutidine were added thereto with ice-cooling under an argon atmosphere, followed by stirring for 144 hours while naturally warming. To the reaction mixture was added a diluted aqueous citric acid solution, followed by evaporation under reduced pressure and extraction with ethyl acetate (15 mL×3). The combined organic layer was washed with saturated brine (15 mL), dried over anhydrous magnesium sulfate, and filtered, and the solvent was evaporated. The obtained residue was purified by silica gel column chromatography (hexane:ethyl acetate=4:1 and then 1:1) to obtain 680 mg of the heading compound as a colorless oily substance (yield 67%).

MS (FAB) (m/z): 499 (MH$^+$).

HRMS (FAB) (m/z): Calcd. for $C_{27}H_{51}O_4SSi$ (MH$^+$): 499.3277. Found, 499.3267.

Reference Example 27

First Step (3R)-3-Deoxo-11-deoxy-12-desethenyl-3-methoxy-14-methoxymethoxy-11-oxo-12-(2-propenyl)thio-4-epimutilin

[Chem. 77]

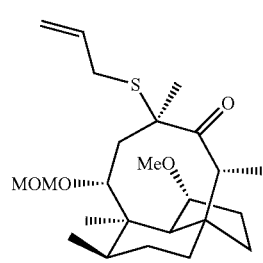

The reaction was carried out using 3.00 g (8.51 mmoL) of (3R)-3-deoxo-11-deoxy-12-desethenyl-3-methoxy-14-methoxymethoxy-11-oxo-4-epimutilin described in Patent Document 19, 3.88 g (17.0 mmoL) of the compound of Reference Example 10, and 20.4 mL (10.2 mmoL) of potassium bis(trimethylsilyl)amide (0.5 mol/L toluene solution) in accordance with the method of First Step of Example 2, and the obtained residue was purified by silica gel column chromatography (hexane:ethyl acetate=20:1 and then 4:1) to obtain 376 mg of the heading compound as a yellow oily substance (yield 10%).

MS (FAB) (m/z): 425.5 (MH$^+$).

HRMS (FAB) (m/z): Calcd. for $C_{24}H_{41}O_4S$ (MH$^+$): 425.2726. Found, 425.2749.

Second Step (3R)-3-Deoxo-11-deoxy-12-desethenyl-3-methoxy-11-oxo-12-(2-propenyl)thio-4-epimutilin

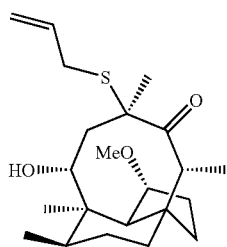

[Chem 78]

The reaction was carried out using 350 mg (0.82 mmoL) of the compound of First Step and 234 mg (1.23 mmoL) of p-toluene sulfonic acid in accordance with the method of Second Step of Example 2, and the obtained residue was purified by silica gel column chromatography (hexane:ethyl acetate=20:1) to obtain 175 mg of the heading compound as a colorless powdery substance (yield 56%).

MS (FAB) (m/z): 381 (MH$^+$).

HRMS (FAB) (m/z): Calcd. for $C_{22}H_{37}O_3S$ (MH$^+$): 381.2463. Found, 381.2470.

Reference Example 28

First Step (3R)-3-Deoxo-11-deoxy-12-desethenyl-3-methoxy-14-methoxymethoxy-12-(1-methylethyl)thio-11-oxo-4-epimutilin

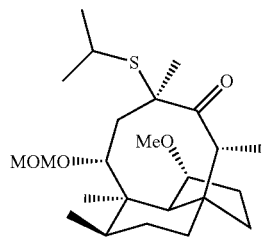

[Chem. 79]

The reaction was carried out using 3.00 g (8.51 mmoL) of (3R)-3-deoxo-11-deoxy-12-desethenyl-3-methoxy-14-methoxymethoxy-11-oxo-4-epimutilin described in Patent Document 19, 2.35 g (10.2 mmoL) of the compound of Reference Example 11, and 20.4 mL (10.2 mmoL) of potassium bis(trimethylsilyl)amide (0.5 mol/L toluene solution) in accordance with the method of First Step of Example 2, and the obtained residue was purified by silica gel column chromatography (hexane:ethyl acetate=10:1) to obtain 2.43 g of the heading compound as a yellow oily substance (yield 67%).

MS (FAB) (m/z): 427.5 (MH$^+$).

HRMS (FAB) (m/z): Calcd. for $C_{24}H_{43}O_4S$ (MH$^+$): 427.2882. Found, 427.2932.

Second Step (3R)-3-Deoxo-11-deoxy-12-desethenyl-3-methoxy-12-(1-methylethyl)thio-11-oxo-4-epimutilin

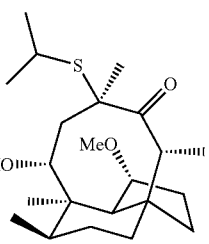

[Chem. 80]

The reaction was carried out using 2.00 g (4.69 mmoL) of the compound of First Step and 1.34 g (7.04 mmoL) of p-toluene sulfonic acid in accordance with the method of Second Step of Example 2, and the obtained residue was purified by silica gel column chromatography (hexane:ethyl acetate=20:1) to obtain 1.43 g of the heading compound as a colorless powdery substance (yield 80%).

MS (FAB) (m/z): 383 (MH$^+$).

HRMS (FAB) (m/z): Calcd. for $C_{22}H_{39}O_3S$ (MH$^+$): 383.2620. Found, 383.2609.

Reference Example 29

First Step (3R)-3-Deoxo-11-deoxy-12-desethenyl-3-methoxy-14-methoxymethoxy-11-oxo-12-phenylthio-4-epimutilin

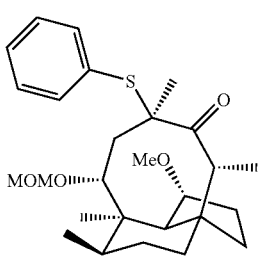

[Chem. 81]

The reaction was carried out using 3.00 g (8.51 mmoL) of (3R)-3-deoxo-11-deoxy-12-desethenyl-3-methoxy-14-methoxymethoxy-11-oxo-4-epimutilin described in Patent Document 19, 2.70 g (10.2 mmoL) of the compound of Reference Example 12, and 20.4 mL (10.2 mmoL) of potassium bis(trimethylsilyl)amide (0.5 mol/L toluene solution) in accordance with the method of First Step of Example 2, and the obtained residue was purified by silica gel column chromatography (hexane:ethyl acetate=10:1) to obtain 3.39 g of the heading compound as a colorless powdery substance (yield 86%).

MS (FAB) (m/z): 429.5 (MH$^+$—CH$_3$O).

HRMS (FAB) (m/z): Calcd. for C$_{26}$H$_{37}$O$_3$S (MH$^+$—CH$_3$O): 429.2463. Found, 429.2442.

Second Step (3R)-3-Deoxo-11-deoxy-12-desethenyl-3-methoxy-11-oxo-12-phenylthio-4-epimutilin

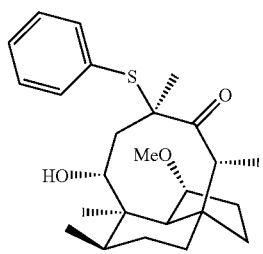

[Chem. 82]

The reaction was carried out using 3.00 g (6.51 mmoL) of the compound of First Step and 1.86 g (9.77 mmoL) of p-toluene sulfonic acid in accordance with the method of Second Step of Example 2, and the obtained residue was purified by silica gel column chromatography (hexane:ethyl acetate=10:1) to obtain 2.23 g of the heading compound as a colorless powdery substance (yield 82%).

MS (FAB) (m/z): 417.6 (MH$^+$).

HRMS (FAB) (m/z): Calcd. for C$_{25}$H$_{37}$O$_3$S (MH$^+$): 417.2463. Found, 417.2433.

Reference Example 30

First Step (3R)-12-(4-Chlorophenyl)thio-3-deoxo-11-deoxy-12-desethenyl-3-methoxy-14-methoxymethoxy-11-oxo-4-epimutilin

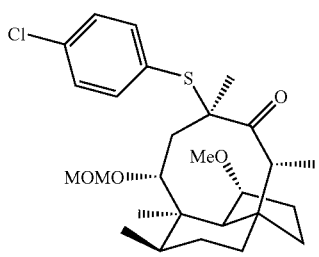

[Chem. 83]

The reaction was carried out using 2.00 g (5.67 mmoL) of (3R)-3-deoxo-11-deoxy-12-desethenyl-3-methoxy-14-methoxymethoxy-11-oxo-4-epimutilin described in Patent Document 19, 2.03 g (6.80 mmoL) of the compound of Reference Example 13, and 13.6 mL (6.80 mmoL) of potassium bis(trimethylsilyl)amide (0.5 mol/L toluene solution) in accordance with the method of First Step of Example 2, and the obtained residue was purified by silica gel column chromatography (hexane:ethyl acetate=30:1 and then 20:1) to obtain 1.57 g of the heading compound as a colorless powdery substance (yield 56%).

MS (FAB) (m/z): 495 (MH$^+$).

HRMS (FAB) (m/z): Calcd. for C$_{27}$H$_{40}$ClO$_4$S (MH$^+$): 495.2336. Found, 495.2334.

Second Step (3R)-12-(4-Chlorophenyl)thio-3-deoxo-11-deoxy-12-desethenyl-3-methoxy-11-oxo-4-epimutilin

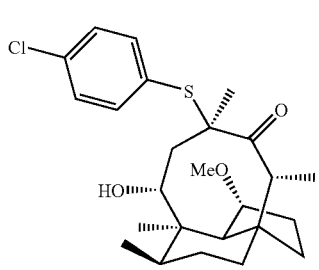

[Chem. 84]

The reaction was carried out using 1.40 g (2.83 mmoL) of the compound of First Step and 808 mg (4.25 mmoL) of p-toluene sulfonic acid in accordance with the method of Second Step of Example 2, and the obtained residue was purified by silica gel column chromatography (hexane:ethyl acetate=10:1) to obtain 1.02 g of the heading compound as a colorless powdery substance (yield 80%).

MS (FAB) (m/z): 433 (MH$^+$—H$_2$O).

HRMS (FAB) (m/z): Calcd. for C$_{25}$H$_{34}$ClO$_2$S (MH$^+$—H$_2$O): 433.1968. Found, 433.1995.

Reference Example 31

First Step (3R)-3-Deoxo-11-deoxy-12-desethenyl-3-methoxy-14-methoxymethoxy-11-oxo-12-(2-pyridyl)thio-4-epimutilin

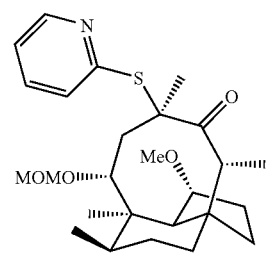

[Chem. 85]

The reaction was carried out using 2.00 g (5.67 mmoL) of (3R)-3-deoxo-11-deoxy-12-desethenyl-3-methoxy-14-methoxymethoxy-11-oxo-4-epimutilin described in Patent Document 19, 1.80 g (6.80 mmoL) of the compound of Reference Example 14, and 13.6 mL (6.80 mmoL) of potassium bis(trimethylsilyl)amide (0.5 mol/L toluene solution) in accordance with the method of First Step of Example 2, and the obtained residue was purified by silica gel column chromatography (hexane:ethyl acetate=10:1) to obtain 2.10 g of the heading compound as a colorless oily substance (yield 80%).

MS (FAB) (m/z): 462 (MH+).
HRMS (FAB) (m/z): Calcd. for $C_{26}H_{40}NO_4S$ (MH+): 462.2678. Found, 462.2673.

Second Step (3R)-3-Deoxo-11-deoxy-12-desethenyl-3-methoxy-11-oxo-12-(2-pyridyl)thio-4-epimutilin

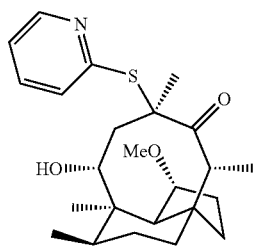

[Chem 86]

The reaction was carried out using 2.00 g (4.33 mmoL) of the compound of First Step and 1.24 g (6.50 mmoL) of p-toluene sulfonic acid in accordance with the method of Second Step of Example 2, and the obtained residue was purified by silica gel column chromatography (hexane:ethyl acetate=6:1) to obtain 1.17 g of the heading compound as a colorless oily substance (yield 65%).

MS (FAB) (m/z): 418 (MH+).
HRMS (FAB) (m/z): Calcd. for $C_{24}H_{36}NO_3S$ (MH+): 418.2416. Found, 418.2439.

Reference Example 32

First Step (3R)-3-Deoxo-11-deoxy-12-desethenyl-3-methoxy-14-methoxymethoxy-12-methylsulfinyl-11-oxo-4-epimutilin

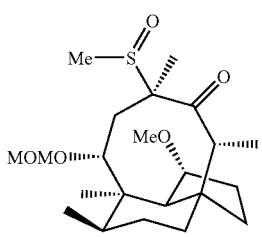

[Chem. 87]

To a solution (15 mL) of 500 mg (1.25 mmoL) of the compound of First Step of Example 2 in methylene chloride was added 366 mg (1.38 mmoL) of m-chloroperbenzoic acid, followed by stirring for at –70° C. for 0.67 hour. The reaction mixture was filtered over Celite, and the residue was washed with methylene chloride. The combined organic layer was evaporated under reduced pressure, and to the residue was added ethyl acetate (15 mL), followed by washing with a 10% aqueous sodium hydrogen sulfite solution (15 mL) and a saturated aqueous sodium hydrogen carbonate solution (15 mL×3). The organic layer was washed with saturated brine (15 mL), dried over anhydrous magnesium sulfate, and filtered, and the solvent was evaporated. The obtained residue was purified by silica gel column chromatography (hexane:ethyl acetate=2:1) to obtain 314 mg of the colorless powdery heading compound (yield 61%).

MS (FAB) (m/z): 415 (MH+).
HRMS (FAB) (m/z): Calcd. for $C_{22}H_{39}O_5S$ (MH+): 415.2518. Found, 415.2534.

Second Step (3R)-3-Deoxo-11-deoxy-12-desethenyl-3-methoxy-14-methoxymethoxy-12-mercapto-11-oxo-4-epimutilin

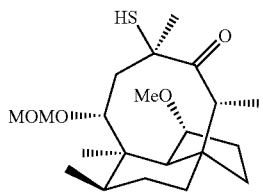

[Chem. 88]

In accordance with the method in the literature (Tetrahedron Lett. 1984, 25, 1753), a solution of 100 mg (0.24 mmoL) of the compound of First Step in trifluoroacetic acid (3 mL) was heated under stirring at 40° C. for 1.5 hours. After cooling, the reaction mixture was evaporated under reduced pressure, and to the residue were added methanol (2.5 mL) and triethylamine (2.5 mL), followed by stirring at room temperature for 4 hours. The reaction mixture was evaporated under reduced pressure, and to the obtained residue was added ethyl acetate (3 mL). Then, the resultant was washed with a saturated aqueous ammonium chloride solution (3 mL) and then with saturated brine (3 mL), dried over anhydrous magnesium sulfate, and filtered, and the solvent was evaporated. The obtained residue was purified by silica gel column chromatography (hexane:ethyl acetate=2:1) to obtain 88.1 mg of the heading compound as a colorless powdery substance (yield 95%).

MS (EI) (m/z): 384 (M+).
HRMS (EI) (m/z): Calcd. for $C_{21}H_{36}O_4S$ (M+): 384.2334. Found, 384.2340.

Third Step (3R)-12-(2-Chloroethyl)thio-3-deoxo-11-deoxy-12-desethenyl-3-methoxy-14-methoxymethoxy-11-oxo-4-epimutilin

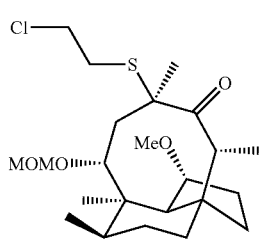

[Chem. 89]

The reaction was carried out using 1.00 g (2.60 mmoL) of the compound of Second Step, 156 mg (3.90 mmoL) of sodium hydride (60% oily substance), and 0.32 mL (3.90 mmoL) of 1-bromo-2-chloroethane in accordance with the method of Second Step of Reference Example 15, and the obtained residue was purified by silica gel column chromatography (hexane:acetone=100:1) to obtain 937 mg of the heading compound as a colorless oily substance (yield 81%).

MS (FAB) (m/z): 447.5 (MH$^+$).
HRMS (FAB) (m/z): Calcd. for $C_{23}H_{40}ClO_4S$ (MH$^+$): 447.2336. Found, 447.2344.

Fourth Step (3R)-12-(2-chloroethyl)thio-3-deoxo-11-deoxy-12-desethenyl-3-methoxy-11-oxo-4-epimutilin

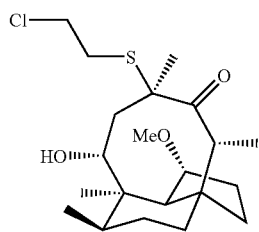

[Chem. 90]

The reaction was carried out using 900 mg (2.01 mmoL) of the compound of Third Step and 574 mg (3.02 mmoL) of p-toluene sulfonic acid in accordance with the method of Second Step of Example 2, and the obtained residue was purified by silica gel column chromatography (hexane:ethyl acetate=4:1) to obtain 585 mg of the heading compound as a colorless oily substance (yield 72%).

MS (FAB) (m/z): 385 (MH$^+$—H$_2$O).
HRMS (FAB) (m/z): Calcd. for $C_{21}H_{34}ClO_2S$ (MH$^+$—H$_2$O): 385.1968. Found, 385.1956.

Reference Example 33

First Step (3R)-3-Deoxo-11-deoxy-12-desethenyl-3-methoxy-14-methoxymethoxy-11-oxo-12-(2,2,2-trifluoroethyl)thio-4-epimutilin

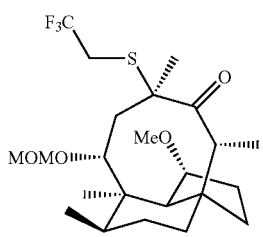

[Chem. 91]

The reaction was carried out using 1.00 g (2.60 mmoL) of the compound of Second Step of Reference Example 32, 156 mg (3.90 mmoL) of sodium hydride (60% oily substance), and 0.38 mL (3.90 mmoL) of 2,2,2-trifluoroethane iodide in accordance with the method of Third Step of Reference Example 32, and the obtained residue was purified by silica gel column chromatography (hexane:ethyl acetate=20:1) to obtain 1.00 g of the heading compound as a colorless powdery substance (yield 82%).

MS (FAB) (m/z): 467 (MH$^+$).
HRMS (FAB) (m/z): Calcd. for $C_{23}H_{38}F_3O_4S$ (MH$^+$): 467.2443. Found, 467.2441.

Second Step (3R)-3-Deoxo-11-deoxy-12-desethenyl-3-methoxy-11-oxo-12-(2,2,2-trifluoroethyl)thio-4-epimutilin

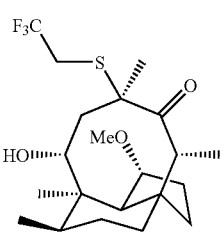

[Chem 92]

The reaction was carried out using 950 mg (2.04 mmoL) of the compound of First Step and 582 mg (3.06 mmoL) of p-toluene sulfonic acid in accordance with the method of Second Step of Example 2, and the obtained residue was purified by silica gel column chromatography (hexane:ethyl acetate=4:1 and then 1:4) to obtain 443 mg of the heading compound as a colorless powdery substance (yield 51%).

MS (FAB) (m/z): 423 (MH$^+$).
HRMS (FAB) (m/z): Calcd. for $C_{21}H_{34}F_3O_3S$ (MH$^+$): 423.2181. Found, 423.2218.

Reference Example 34

First Step (3R)-12-Benzoylthio-3-deoxo-11-deoxy-12-desethenyl-3-methoxy-14-methoxymethoxy-11-oxo-4-epimutilin

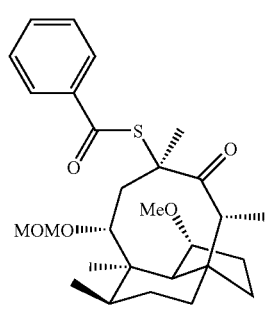

[Chem. 93]

The reaction was carried out using 1.00 g (2.60 mmoL) of the compound of Second Step of Reference Example 32, 156 mg (3.90 mmoL) of sodium hydride (60% oily substance), and 0.45 mL (3.90 mmoL) of benzoyl chloride in accordance with the method of Third Step of Reference Example 32, and the obtained residue was purified by silica gel column chromatography (hexane:ethyl acetate=30:1) to obtain 1.08 g of the heading compound as a colorless oily substance (yield 85%).

MS (FAB) (m/z): 489 (MH⁺).

HRMS (FAB) (m/z): Calcd. for $C_{28}H_{41}O_5S$ (MH⁺): 489.2675. Found, 489.2719.

Second Step (3R)-12-Benzoylthio-3-deoxo-11-deoxy-12-desethenyl-3-methoxy-11-oxo-4-epimutilin

[Chem. 94]

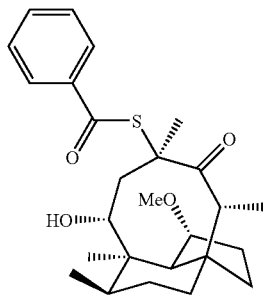

The reaction was carried out using 1.00 g (2.05 mmoL) of the compound of First Step and 586 mg (3.08 mmoL) of p-toluene sulfonic acid in accordance with the method of Second Step of Example 2, and the obtained residue was purified by silica gel column chromatography (hexane:ethyl acetate=6:1 and then 4:1) to obtain 780 mg of the heading compound as a colorless powdery substance (yield 86%).

MS (FAB) (m/z): 445 (MH⁺).

HRMS (FAB) (m/z): Calcd. for $C_{26}H_{37}O_4S$ (MH⁺): 445.2413. Found, 445.2441.

Reference Example 35

First Step (3R)-12-Benzylthio-3-deoxo-11-deoxy-12-desethenyl-3-methoxy-14-methoxymethoxy-11-oxo-4-epimutilin

[Chem. 95]

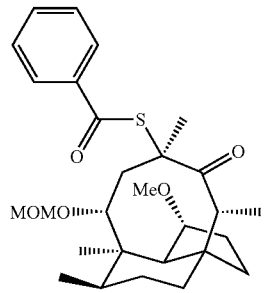

The reaction was carried out using 1.00 g (2.60 mmoL) of the compound of Second Step of Reference Example 32, 156 mg (3.90 mmoL) of sodium hydride (60% oily substance), and 0.46 mL (3.90 mmoL) of benzyl bromide in accordance with Third Step of Reference Example 32, and to the obtained residue was added diisopropyl ether. The resultant was washed and then suction-filtered to obtain 1.07 g of the heading compound as a colorless powdery substance (yield 87%).

MS (FAB) (m/z): 475 (MH⁺).

HRMS (FAB) (m/z): Calcd. for $C_{28}H_{43}O_4S$ (MH⁺): 475.2882. Found, 475.2899.

Second Step (3R)-12-Benzylthio-3-deoxo-11-deoxy-12-desethenyl-3-methoxy-11-oxo-4-epimutilin

[Chem. 96]

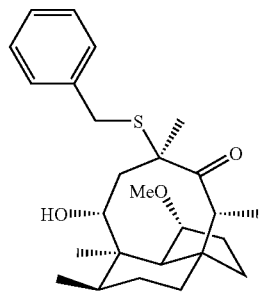

The reaction was carried out using 1.00 g (2.11 mmoL) of the compound of First Step and 603 mg (3.17 mmoL) of p-toluene sulfonic acid in accordance with the method of Second Step of Example 2, and the obtained residue was purified by silica gel column chromatography (hexane:ethyl acetate=10:1, 6:1, and then 4:1) to obtain 566 mg of the heading compound as a colorless powdery substance (yield 62%).

MS (FAB) (m/z): 413 (MH⁺—H₂O).

HRMS (FAB) (m/z): Calcd. for $C_{26}H_{37}O_2S$ (MH⁺—H₂O): 413.2514. Found, 413.2491.

Reference Example 36

First Step (3R)-12-(3-Benzoyloxy)propylthio-3-deoxo-11-deoxy-12-desethenyl-3-methoxy-14-methoxymethoxy-11-oxo-4-epimutilin

[Chem. 97]

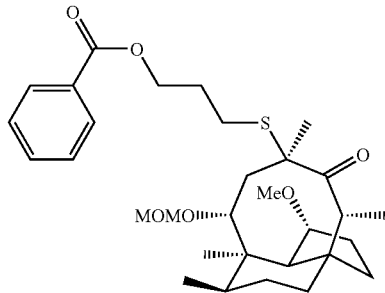

The reaction was carried out using 1.25 g (3.25 mmoL) of the compound of Second Step of Reference Example 32, 195 mg (4.88 mmoL) of sodium hydride (60% oily substance), and 2.27 g (9.75 mmoL) of 3-bromopropyl benzoate in accordance with the method of Third Step of Reference Example 32, and the obtained residue was purified by silica gel column chromatography (hexane:ethyl acetate=10:1) to obtain 1.54 g of the heading compound as a colorless oily substance (yield 87%).

MS (FAB) (m/z): 547 (MH⁺).

HRMS (FAB) (m/z): Calcd. for $C_{31}H_{47}O_6S$ (MH⁺): 547.3093. Found, 547.30.

Second Step (3R)-3-Deoxo-11-deoxy-12-desethenyl-12-(3-hydroxy)propylthio-3-methoxy-14-methoxymethoxy-11-oxo-4-epimutilin

[Chem. 98]

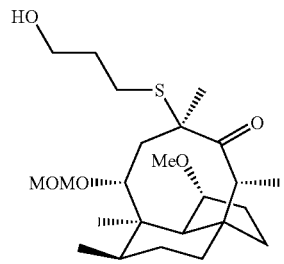

To a solution (28 mL) of 1.53 g (2.80 mmoL) of the compound of First Step in anhydrous methanol was added 774 mg (5.60 mmoL) of potassium carbonate with ice-cooling under an argon atmosphere, followed by stirring for 1.5 hours while naturally warming. The reaction mixture was filtered over Celite, and the residue was washed with ethyl acetate. The combined organic layer was evaporated under reduced pressure, and to the residue was added a diluted aqueous citric acid solution (10 mL), followed by extraction with ethyl acetate (10 mL×3). The combined organic layer was washed with saturated brine (10 mL), dried over anhydrous sodium sulfate, and filtered, and the solvent was evaporated. The obtained residue was purified by silica gel column chromatography (hexane:ethyl acetate=4:1 and then 1:1) to obtain 1.13 g of the heading compound as a colorless oily substance (yield 91%).

MS (FAB) (m/z): 442 ($M^+$).
HRMS (FAB) (m/z): Calcd. for $C_{24}H_{42}O_5S$ ($M^+$): 442.2753. Found, 442.2769.

Third Step (3R)-3-Deoxo-11-deoxy-12-desethenyl-12-(3-fluoro)propylthio-3-methoxy-14-methoxymethoxy-11-oxo-4-epimutilin

[Chem. 99]

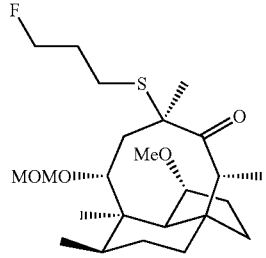

To a solution (25 mL) of 1.10 g (2.49 mmoL) of the compound of Second Step in toluene was added 1.12 mL (7.47 mmoL) of 1,8-diazabicyclo[5.4.0]unde-7-cene with ice-cooling under an argon atmosphere, and then 1.03 mL (3.74 mmoL) of perfluorooctanesulfonyl fluoride was added dropwise thereto, followed by stirring for 1.5 hours while naturally warming. To the reaction mixture was added a diluted aqueous citric acid solution (20 mL), followed by extraction with ethyl acetate (30 mL×3). The combined organic layer was washed with saturated brine (30 mL), dried over anhydrous sodium sulfate, and then filtered, and the solvent was evaporated. The obtained residue was purified by silica gel column chromatography (hexane:ethyl acetate=4:1) to obtain 197 mg of the heading compound as a yellow oily substance (yield 18%).

MS (FAB) (m/z): 445 ($MH^+$).
HRMS (FAB) (m/z): Calcd. for $C_{24}H_{42}FO_4S$ ($MH^+$): 445.2788. Found, 445.2768.

Fourth Step (3R)-3-Deoxo-11-deoxy-12-desethenyl-3-methoxy-12-(3-fluoro)propylthio-11-oxo-4-epimutilin

[Chem. 100]

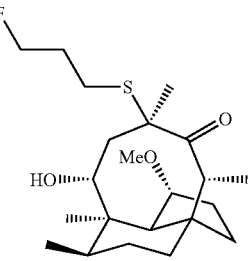

The reaction was carried out using 187 mg (0.42 mmoL) of the compound of Third Step and 120 mg (0.63 mmoL) of p-toluene sulfonic acid in accordance with the method of Second Step of Example 2, and the obtained residue was purified by silica gel column chromatography (hexane:ethyl acetate=4:1) to obtain 143 mg of the heading compound as a colorless powdery substance (yield 85%).

MS (FAB) (m/z): 383 ($MH^+$—$H_2O$).
HRMS (FAB) (m/z): Calcd. for $C_{22}H_{36}FO_2S$ ($MH^+$—$H_2O$): 383.2420. Found, 383.2424.

Reference Example 37

First Step (3R)-3-Deoxo-11-deoxy-12-desethenyl-3-methoxy-14-methoxymethoxy-12-{exo-8'-methyl-8'-azabicyclo[3.2.1]octane-3-carbonyl}thio-11-oxo-4-epimutilin

[Chem. 101]

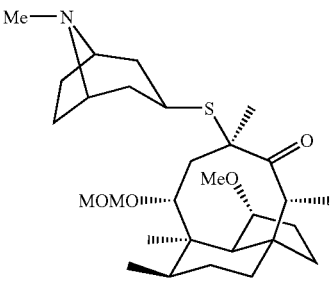

The reaction was carried out using 5.00 g (13.0 mmoL) of the compound of Second Step of Reference Example 32, 780 mg (19.5 mmoL) of sodium hydride (60% oily substance), and 3.14 g (14.3 mmoL) of tropine-3-mesylate synthesized by the method described in patent (WO 2005023257) in accordance with the method of Third Step of Reference Example 32, and the obtained residue was purified by silica gel column chromatography (NH, hexane:ethyl acetate=10:1 and then 4:1) to obtain 2.41 g of the heading compound as a colorless oily substance (yield 37%).

MS (FAB) (m/z): 508.5 ($MH^+$).

HRMS (FAB) (m/z): Calcd. for C$_{29}$H$_{50}$NO$_4$S (MH$^+$): 508.3461. Found, 508.3482.

Second Step (3R)-3-Deoxo-11-deoxy-12-desethenyl-3-methoxy-12-{exo-8'-methyl-8'-azabicyclo[3.2.1]octane-3-carbonyl}thio-11-oxo-4-epimutilin

[Chem. 102]

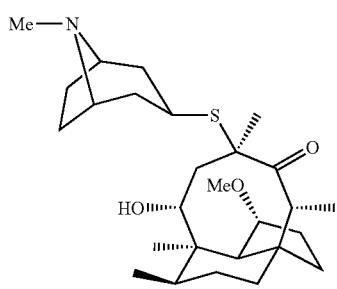

The reaction was carried out using 2.40 g (4.73 mmoL) of the compound of First Step and 2.24 g (11.8 mmoL) of p-toluene sulfonic acid in accordance with the method of Second Step of Example 2, and the obtained residue was purified by silica gel column chromatography (NH, ethyl acetate, and then ethyl acetate:methanol=20:1) to obtain 1.07 g of the heading compound as a colorless powdery substance (yield 49%).

MS (FAB) (m/z): 464 (MH$^+$).

HRMS (FAB) (m/z): Calcd. for C$_{27}$H$_{46}$NO$_3$S (MH$^+$): 464.3198. Found, 464.3242.

Test Example

The measurement of MIC [minimum inhibitory concentration (MIC)] was carried out in accordance with NCCLS (Methods for dilution antimicrobial susceptibility tests for bacteria that grow aerobically; approved standard-sixth edition. NCCLS. 2003, M7-A6, Vol. 23 (No. 2)). As a result, it was found that the compound of the present invention has an excellent antimicrobial activity.

The compound according to the present invention exhibits a strong antimicrobial activity, in particular, against drug-resistant Gram-positive bacteria, such as methicillin-resistant Staphylococci (for example, methicillin-resistant *Staphylococcus aureus* L39), quinolone-methicillin-resistant *Staphylococcus* (for example, *Staphylococcus aureus* OITI MR1-1002), penicillin-resistant *Streptococcus pneumoniae* (for example, penicillin-resistant *Streptococcus pneumoniae* PR44), quinoline-resistant *Streptococcus pneumoniae* (for example, *Streptococcus pneumoniae* No. 55), vancomycin-resistant enterococci (for example, *Enterococcus faecium* A2280), and the like.

INDUSTRIAL AVAILABILITY

The compound according to the present invention is effective against various infectious diseases involved in Gram-positive bacteria and Gram-negative bacteria including various drug-resistant bacteria.

The invention claimed is:

1. A mutilin compound represented by the following formula (1):

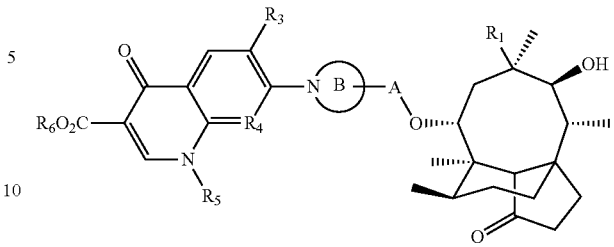

(1)

wherein R$_1$ represents a lower alkenyl group, a thiol group or a lower alkylthio group,
A represents the following chemical formula:

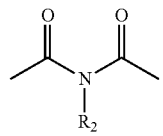

(wherein R$_2$ represents a hydrogen atom or a lower alkyl group which may be substituted),
the ring B containing a nitrogen atom represents the following chemical formula:

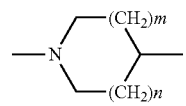

(wherein m and n represent 1),
R$_3$ represents a hydrogen atom or a fluorine atom,
R$_4$ represents CH, N, or the formula: C—X or COR$_7$
(wherein X represents a halogen atom, and R$_7$ represents a hydrogen atom or a lower alkyl group which may be substituted),
R$_5$ represents a lower alkyl group which may be substituted, a lower alkenyl group which may be substituted, a cyclopropyl group which may be substituted, an unsubstituted cyclopropylmethyl group, or a phenyl group which may be substituted, or
R$_5$ and R$_7$ may be combined to form a ring, and in this case, a lower alkyl group, which may be substituted, may be substituted at an arbitrary carbon atom of the ring, and
R$_6$ represents a hydrogen atom, a lower alkyl group which may be substituted, or a boric acid group which may be substituted, or
a pharmaceutically acceptable addition salt thereof.

2. The mutilin compound or pharmaceutically acceptable addition salt thereof according to claim 1, wherein in the formula (1), R$_1$ represents a lower alkenyl group.

3. The mutilin compound or pharmaceutically acceptable addition salt thereof according to claim 1, wherein in the formula (1), R$_1$ represents a thiol group or a lower alkylthio group.

4. A method of treating Gram-positive bacteria and/or Gram-negative bacteria, comprising administering a mutilin compound according to claim 1 or a pharmaceutically acceptable addition salt thereof to a patient in need thereof.

5. A pharmaceutical composition comprising a mutilin compound according to claim 1 or a pharmaceutically acceptable addition salt thereof, and a pharmaceutically acceptable adjuvant, carrier, excipient, lubricant, binder, agent and/or diluent.

* * * * *